US012129298B2

(12) United States Patent
Spreter Von Kreudenstein

(10) Patent No.: US 12,129,298 B2
(45) Date of Patent: Oct. 29, 2024

(54) COMPOSITIONS INCLUDING CD3 ANTIGEN BINDING FRAGMENTS AND USES THEREOF

(71) Applicant: Daiichi Sankyo Company, Limited, Tokyo (JP)

(72) Inventor: Thomas Spreter Von Kreudenstein, Wiesbaden (DE)

(73) Assignee: Daiichi Sankyo Company, Limited, Tokyo (JP)

( * ) Notice: Subject to any disclaimer, the term of this patent is extended or adjusted under 35 U.S.C. 154(b) by 788 days.

(21) Appl. No.: 17/254,105

(22) PCT Filed: Jun. 20, 2019

(86) PCT No.: PCT/IB2019/055228
§ 371 (c)(1),
(2) Date: Dec. 18, 2020

(87) PCT Pub. No.: WO2019/244107
PCT Pub. Date: Dec. 26, 2019

(65) Prior Publication Data
US 2021/0277118 A1    Sep. 9, 2021

Related U.S. Application Data

(60) Provisional application No. 62/687,967, filed on Jun. 21, 2018.

(51) Int. Cl.
*C07K 16/28* (2006.01)

(52) U.S. Cl.
CPC ...... *C07K 16/2809* (2013.01); *C07K 2317/24* (2013.01); *C07K 2317/31* (2013.01); *C07K 2317/622* (2013.01); *C07K 2317/94* (2013.01)

(58) Field of Classification Search
None
See application file for complete search history.

(56) References Cited

U.S. PATENT DOCUMENTS

| 4,281,061 | A  | * | 7/1981  | Zuk ........................ C12N 9/96 435/7.37 |
| 5,859,205 | A  | * | 1/1999  | Adair ................... C07K 16/465 530/387.3 |
| 5,977,322 | A  | * | 11/1999 | Marks ................... F16H 59/105 530/387.3 |
| 6,541,225 | B1 | * | 4/2003  | Li ....................... A61K 47/6843 435/7.1 |
| 7,968,685 | B2 | * | 6/2011  | Brack .................... A61P 35/00 424/130.1 |
| 2006/0099582 | A1 | * | 5/2006 | Papadopoulos ......... A61P 41/00 435/6.16 |
| 2014/0154253 | A1 | * | 6/2014 | Ng ......................... A61P 35/02 435/69.6 |
| 2015/0376296 | A1 | * | 12/2015 | Fedorov ................ A61P 43/00 536/23.4 |
| 2017/0355767 | A1 | * | 12/2017 | Engelberts ............. A61P 35/00 |

FOREIGN PATENT DOCUMENTS

| WO | WO-2014/012085 A2 | 1/2014 | |
| WO | WO-2014108483 A1 * | 7/2014 | ............. A61P 29/00 |
| WO | WO-2015/063339 A1 | 5/2015 | |
| WO | WO-2015/109131 A2 | 7/2015 | |
| WO | WO-2015/181098 A1 | 12/2015 | |
| WO | WO-2016/014974 A2 | 1/2016 | |
| WO | WO-2016/071004 A1 | 5/2016 | |
| WO | WO-2016/086196 A2 | 6/2016 | |
| WO | WO-2016/116626 A1 | 7/2016 | |
| WO | WO-2017/100372 A1 | 6/2017 | |
| WO | WO-2018/117237 A1 | 6/2018 | |
| WO | WO-2018/147245 A1 | 8/2018 | |

OTHER PUBLICATIONS

Eduardo Padlan, Mol Immunol. Feb. 1994;31(3):169-217. (Year: 1994).*
Portolano et al., J Immunol. Feb. 1, 1993;150(3):880-7. (Year: 1993).*
Huston et al. (Proc. Natl. Acad. Sci. USA vol. 85, pp. 5879-5883, 1988). (Year: 1988).*
International Search Report dated Oct. 14, 2019 in PCT/IB2019/055228.
Written Opinion dated Dec. 30, 2020 in PCT/IB2019/055228.

* cited by examiner

*Primary Examiner* — Zachary S Skelding
(74) *Attorney, Agent, or Firm* — Foley & Lardner LLP

(57) ABSTRACT

The present disclosure relates generally to immunoglobulin-related compositions (e.g., antibodies or antigen binding fragments thereof) that can bind to CD3 and uses thereof.

26 Claims, 14 Drawing Sheets
Specification includes a Sequence Listing.

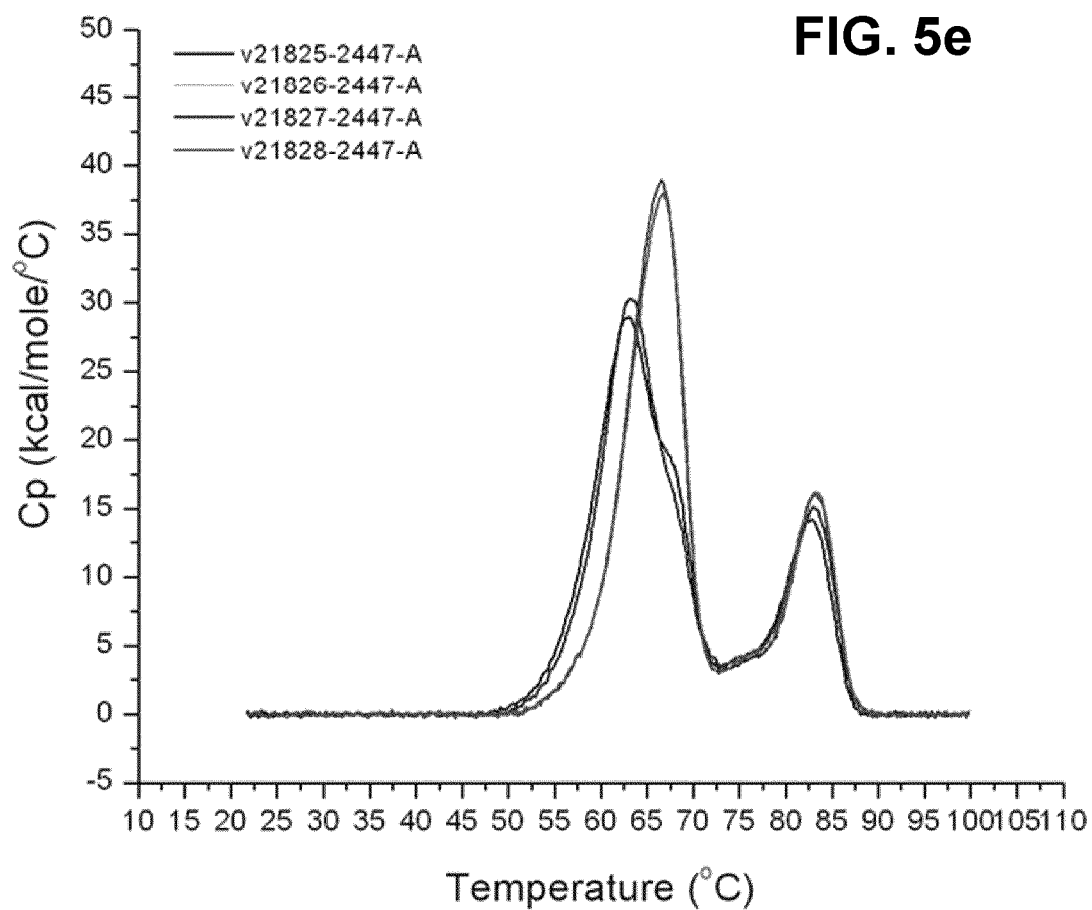

18346 (C3E-1)

19362

19363

21829

21831

SEQUENCE LISTING

<160> NUMBER OF SEQ ID NOS: 247

<210> SEQ ID NO 1
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Arg Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 2

<400> SEQUENCE: 2

000

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 3

Gly Val Thr Phe Asn Tyr Tyr Gly
1               5

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

Thr Leu Asp Gly Arg Asp Gly Trp Val Ala Tyr
1               5                   10

<210> SEQ ID NO 5
<211> LENGTH: 8
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ile Thr Arg Ser Gly Gly Arg Ile
1               5

<210> SEQ ID NO 6
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Phe Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95

Gly Phe Ile Phe Gly Gly Gly Thr Lys Leu Thr Val Leu
            100                 105

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Thr Gly Asn Ile Gly Ser Asn Tyr
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Ser Tyr Ser Ser Gly Phe Ile
1               5

<210> SEQ ID NO 9
<211> LENGTH: 3
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 9

Arg Asn Asp
1

<210> SEQ ID NO 10
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Ser Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 11

<400> SEQUENCE: 11

000

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Val Thr Phe Asn Tyr Tyr Gly
1               5

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

```
Thr Leu Asp Gly Arg Asp Gly Trp Val Ala Tyr
1               5                   10

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ile Thr Ser Ser Gly Gly Arg Ile
1               5

<210> SEQ ID NO 15
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Phe Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95

Gly Phe Ile Phe Gly Gly Gly Thr Lys Leu Thr Val Leu
            100                 105

<210> SEQ ID NO 16

<400> SEQUENCE: 16

000

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Thr Gly Asn Ile Gly Ser Asn Tyr
1               5

<210> SEQ ID NO 18
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 18

Gln Ser Tyr Ser Ser Gly Phe Ile
1               5

<210> SEQ ID NO 19
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Arg Asn Asp
1

<210> SEQ ID NO 20
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Arg Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 21

<400> SEQUENCE: 21

000

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22
```

```
Gly Val Thr Phe Asn Tyr Tyr Gly
1               5

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Thr Leu Asp Gly Arg Asp Gly Trp Val Ala Tyr
1               5                   10

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ile Thr Arg Ser Gly Gly Arg Ile
1               5

<210> SEQ ID NO 25
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95

Gly Phe Ile Phe Gly Gly Gly Thr Lys Leu Thr Val Leu
            100                 105

<210> SEQ ID NO 26

<400> SEQUENCE: 26

000

<210> SEQ ID NO 27
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 27

Thr Gly Asn Ile Gly Ser Asn Tyr
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln Ser Tyr Ser Ser Gly Phe Ile
1               5

<210> SEQ ID NO 29
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Asn Asp
1

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Ser Ser Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
            115

<210> SEQ ID NO 31
```

```
<400> SEQUENCE: 31

000

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Val Thr Phe Asn Tyr Tyr Gly
1               5

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Thr Leu Asp Gly Arg Asp Gly Trp Val Ala Tyr
1               5                   10

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Thr Ser Ser Gly Gly Arg Ile
1               5

<210> SEQ ID NO 35
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95
```

Gly Phe Ile Phe Gly Gly Gly Thr Lys Leu Thr Val Leu
            100                 105

<210> SEQ ID NO 36

<400> SEQUENCE: 36

000

<210> SEQ ID NO 37
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Gly Asn Ile Gly Ser Asn Tyr
1               5

<210> SEQ ID NO 38
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (37)..(37)
<223> OTHER INFORMATION: a, c, t, g, unknown or other

<400> SEQUENCE: 38
gctagcgcta ccggactcag atcccccccc cccccdn                            37

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gln Ser Tyr Ser Ser Gly Phe Ile
1               5

<210> SEQ ID NO 40
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
tcactgagct ggtgagagtg tagagccc                                      28

<210> SEQ ID NO 41
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Asn Asp
1

<210> SEQ ID NO 42
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
tcaccgagct gctgagggtg tagagccc                                        28

<210> SEQ ID NO 43
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 44
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
gaggtgcagc tggtggagtc cggcggcggc ctggtgcagc caggaggctc tctgcggctg     60
agctgcgcag cctccggcgt gaccttcaac tactatggca tgagctggat cagacaggcc    120
cccggcaagg gcctggagtg ggtggcctct atcaccaata gcggcggcag gatctactat    180
cctgactccg tgaagggcag gtttacaatc agcggggaga cacccagaa gacactgtac    240 ctgcagatga acagcctgcg ggccgaggat accgccgtgt actattgcac actggacggc    300
agagacggat gggtggcata ttggggacag ggcaccctgg tgacagtgag ctcc    354

<210> SEQ ID NO 45
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Val Thr Phe Asn Tyr Tyr Gly
1               5

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Thr Leu Asp Gly Arg Asp Gly Trp Val Ala Tyr
1               5                   10

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ile Thr Asn Ser Gly Gly Arg Ile
1               5

<210> SEQ ID NO 48
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45

Ile Tyr Arg Asp Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu

<210> SEQ ID NO 49
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49

```
aactttatgc tgacccagcc acactccgtg tctgagagcc ccggcaagac cgtgacaatc    60
agctgtaaga gaaacacagg caatatcggc tccaactacg tgaattggta tcagcagcac   120
gagggctcta gccctaccac aatcatctac cgggacgata agcggcccga cggcgtgagc   180
gatcggttct ccggctctat cgacagatcg cctccctgac catctctaat             240
ctgaagacag aggacgaggc cgattacttt tgtcagagct atagctccgg cttcatcttt   300
ggaggaggaa ccaagctgac agtgctg                                       327
```

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Thr Gly Asn Ile Gly Ser Asn Tyr
1               5

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

Gln Ser Tyr Ser Ser Gly Phe Ile
1               5

<210> SEQ ID NO 52
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Arg Asp Asp
1

<210> SEQ ID NO 53
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 54
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gaggtgcagc tggtggagtc cggcggcggc ctggtgcagc ctggcggcag cctgcggctg      60
tcctgcgccg cctctggcgt gacattcaac tactatggca tgtcttggat cagacaggcc     120
ccaggcaagg gcctggagtg ggtggccagc atcaccaatt ccggcggcag gatctactat     180
cccgacagcg tgaagggcag gtttacaatc tcccgcgaga cacccagaa  gacactgtac     240 ctgcagatga atagcctgag ggccgaggat accgccgtgt actattgcac actggacggc     300
agagacggat gggtggcata ttggggacag ggcaccctgg tgacagtgag ctcc            354

<210> SEQ ID NO 55
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Val Thr Phe Asn Tyr Tyr Gly
1               5

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

```
Thr Leu Asp Gly Arg Asp Gly Trp Val Ala Tyr
1               5                   10
```

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

```
Ile Thr Asn Ser Gly Gly Arg Ile
1               5
```

<210> SEQ ID NO 58
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Gln Ser Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105
```

<210> SEQ ID NO 59
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59

```
cagtccgtgc tgacccagcc accttctgcc agcggaaccc ctggccagcg ggtgacaatc    60
tcttgtaaga gaaacaccgg caatatcggc agcaactacg tgaattggta tcagcagctg   120
cctggcacag ccccaaagct gctgatctac cgggacgata gcggcccga cggagtgcct    180 gatagatttt ccggctctaa gagcggcacc tccgcctctc tggccatctc tggcctgcag   240
agcgaggacg aggccgatta ctattgtcag tcctattcta cggcttcat ctttggagga    300 ggaaccaagc tgacagtgct g                                              321
```

<210> SEQ ID NO 60
<211> LENGTH: 8
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Thr Gly Asn Ile Gly Ser Asn Tyr
1               5

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Ser Tyr Ser Ser Gly Phe Ile
1               5

<210> SEQ ID NO 62
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Arg Asp Asp
1

<210> SEQ ID NO 63
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Ser Ser Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 64

```
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
gaggtgcagc tggtggagtc tggcggcggc ctggtgcagc ctggcggcag cctgcggctg      60
tcctgcgccg cctctggcgt gacattcaac tactatggca tgagctggat cagacaggcc     120
ccaggcaagg gactggagtg ggtggcctcc atcaccagct ccggcggcag gatctactat     180
cccgactctg tgaagggcag gtttacaatc agccgcgaga cacccagaa gacactgtac     240 ctgcagatga atagcctgag ggccgaggat accgccgtgt actattgcac actggacggc     300
agagacggat gggtggcata ttggggacag ggcaccctgg tgacagtgtc ttcc           354

<210> SEQ ID NO 65
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Val Thr Phe Asn Tyr Tyr Gly
1               5

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Thr Leu Asp Gly Arg Asp Gly Trp Val Ala Tyr
1               5                   10

<210> SEQ ID NO 67
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ile Thr Ser Ser Gly Gly Arg Ile
1               5

<210> SEQ ID NO 68
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68
```

```
Gln Val Val Leu Thr Gln Pro Pro Ser Ala Ser Gly Thr Pro Gly Gln
1               5                   10                  15
Arg Val Thr Ile Ser Cys Lys Arg Asn Thr Gly Asn Ile Gly Ser Asn
            20                  25                  30
Tyr Val Asn Trp Tyr Gln Gln Leu Pro Gly Thr Ala Pro Lys Leu Leu
        35                  40                  45
Ile Tyr Arg Asp Asp Lys Arg Pro Asp Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Gln Ser Tyr Ser Ser Gly Phe
                85                  90                  95
Ile Phe Gly Gly Gly Thr Lys Leu Thr Val Leu
            100                 105
```

\<210\> SEQ ID NO 69
\<211\> LENGTH: 321
\<212\> TYPE: DNA
\<213\> ORGANISM: Artificial Sequence
\<220\> FEATURE:
\<221\> NAME/KEY: source
\<223\> OTHER INFORMATION: /note="Description of Artificial Sequence:
      Synthetic polynucleotide"

\<400\> SEQUENCE: 69

```
caggtggtgc tgacccagcc accttctgcc agcggaaccc ctggccagcg ggtgacaatc    60
tcctgtaaga gaaacaccgg caatatcggc tctaactacg tgaattggta tcagcagctg   120
cctggcacag ccccaaagct gctgatctac cgggacgata agagacccga cggcgtgcct   180
gatagatttt ccggctctaa gagcggcacc tccgcctctc tggccatcag cggactgcag   240
tccgaggacg aggcagatta ctattgtcag tcctattcct ctggcttcat ctttggagga   300
ggaaccaagc tgacagtgct g                                             321
```

\<210\> SEQ ID NO 70
\<211\> LENGTH: 8
\<212\> TYPE: PRT
\<213\> ORGANISM: Artificial Sequence
\<220\> FEATURE:
\<221\> NAME/KEY: source
\<223\> OTHER INFORMATION: /note="Description of Artificial Sequence:
      Synthetic peptide"

\<400\> SEQUENCE: 70

```
Thr Gly Asn Ile Gly Ser Asn Tyr
1               5
```

\<210\> SEQ ID NO 71
\<211\> LENGTH: 8
\<212\> TYPE: PRT
\<213\> ORGANISM: Artificial Sequence
\<220\> FEATURE:
\<221\> NAME/KEY: source
\<223\> OTHER INFORMATION: /note="Description of Artificial Sequence:
      Synthetic peptide"

\<400\> SEQUENCE: 71

```
Gln Ser Tyr Ser Ser Gly Phe Ile
1               5
```

\<210\> SEQ ID NO 72
\<211\> LENGTH: 3
\<212\> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 72

Arg Asp Asp
1

<210> SEQ ID NO 73
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 74
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74
gaggtgcagc tggtggagag cggcggcggc ctggtgcagc ctggaggctc cctgcggctg      60
tcttgcgcag ccagcggcgt gacattcaac tactatggca tgagctggat cagacaggcc    120
ccaggcaagg gactggagtg ggtggcctcc atcaccaatt ctggcggcag gatctactat    180
cccgactctg tgaagggcag gtttacaatc agccgcgaga cacccagaa gacactgtac    240 ctgcagatga acagcctgcg ggccgaggat accgccgtgt actattgcac actggacggc    300
agagacggat gggtggcata ttggggacag ggcaccctgg tgacagtgag ctcc    354

<210> SEQ ID NO 75
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 75

Gly Val Thr Phe Asn Tyr Tyr Gly
1               5

<210> SEQ ID NO 76
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Thr Leu Asp Gly Arg Asp Gly Trp Val Ala Tyr
1               5                   10

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ile Thr Asn Ser Gly Gly Arg Ile
1               5

<210> SEQ ID NO 78
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Phe Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105

<210> SEQ ID NO 79
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

```
cagttcgtgc tgacccagcc acctagcgcc tccggaaccc ctggccagcg ggtgacaatc    60
tcctgtaaga gaaacaccgg caatatcggc tctaactacg tgaattggta tcagcagctg   120
cctggcacag ccccaaagct gctgatctac cgggacgata agagacccga cggcgtgcct   180
gatagatttt ctggcagcaa gtccggcacc tctgccagcc tggccatcag cggactgcag   240
tccgaggacg aggcagatta ctattgtcag agctattcta gcggcttcat ctttggagga   300
ggaaccaagc tgacagtgct g                                             321
```

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

Thr Gly Asn Ile Gly Ser Asn Tyr
1               5

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Gln Ser Tyr Ser Ser Gly Phe Ile
1               5

<210> SEQ ID NO 82
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Arg Asp Asp
1

<210> SEQ ID NO 83
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val

```
                35                  40                  45
Ala Ser Ile Thr Asn Ser Gly Gly Arg Ile Tyr Tyr Pro Asp Ser Val
        50                  55                  60
Lys Gly Arg Phe Thr Ile Ser Arg Glu Asn Thr Gln Lys Thr Leu Tyr
 65                  70                  75                  80
Leu Gln Met Asn Ser Leu Arg Ala Glu Asp Thr Ala Val Tyr Tyr Cys
                85                  90                  95
Thr Leu Asp Gly Arg Asp Gly Trp Val Ala Tyr Trp Gly Gln Gly Thr
            100                 105                 110
Leu Val Thr Val Ser Ser
            115

<210> SEQ ID NO 84
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
gaggtgcagc tggtggagag cggcggcggc ctggtgcagc ctggaggctc cctgcggctg      60
tcttgcgcag ccagcggcgt gacattcaac tactatggca tgagctggat cagacaggcc     120
ccaggcaagg gactggagtg ggtggcctcc atcaccaatt ctggcggcag gatctactat     180
cccgactctg tgaagggcag gtttacaatc agccgcgaga cacccagaa gacactgtac      240 ctgcagatga acagcctgcg ggccgaggat accgccgtgt actattgcac actggacggc    300
agagacggat gggtggcata ttggggacag ggcaccctgg tgacagtgag ctcc           354

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gly Val Thr Phe Asn Tyr Tyr Gly
1               5

<210> SEQ ID NO 86
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Thr Leu Asp Gly Arg Asp Gly Trp Val Ala Tyr
1               5                   10

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 87

Ile Thr Asn Ser Gly Gly Arg Ile
1               5

<210> SEQ ID NO 88
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gln Leu Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105

<210> SEQ ID NO 89
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
cagctggtgc tgacccagcc acctagcgcc tccggaaccc ctggccagcg ggtgacaatc    60
tcctgtaaga gaaacaccgg caatatcggc tctaactacg tgaattggta tcagcagctg   120
cctggcacag ccccaaagct gctgatctac cgggacgata agagacccga cggcgtgcct   180
gatagatttt ctggcagcaa gtccggcacc tctgccagcc tggccatcag cggactgcag   240
tccgaggacg aggcagatta ctattgtcag agctattcta gcggcttcat ctttggagga   300
ggaaccaagc tgacagtgct g                                             321

<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Thr Gly Asn Ile Gly Ser Asn Tyr
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gln Ser Tyr Ser Ser Gly Phe Ile
1               5

<210> SEQ ID NO 92
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Arg Asp Asp
1

<210> SEQ ID NO 93
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 94
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
gaggtgcagc tggtggagag cggcggcggc ctggtgcagc ctggaggctc cctgcggctg    60

-continued

```
tcttgcgcag ccagcggcgt gacattcaac tactatggca tgagctggat cagacaggcc      120
ccaggcaagg gactggagtg ggtggcctcc atcaccaatt ctggcggcag gatctactat      180
cccgactctg tgaagggcag gtttacaatc agccgcgaga cacccagaa gacactgtac       240 ctgcagatga acagcctgcg ggccgaggat accgccgtgt actattgcac actggacggc      300
agagacggat gggtggcata ttggggacag ggcaccctgg tgacagtgag ctcc            354
```

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 95

Gly Val Thr Phe Asn Tyr Tyr Gly
1               5

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 96

Thr Leu Asp Gly Arg Asp Gly Trp Val Ala Tyr
1               5                   10

<210> SEQ ID NO 97
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 97

Ile Thr Asn Ser Gly Gly Arg Ile
1               5

<210> SEQ ID NO 98
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 98

Gln Ile Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gln Ser Tyr Ser Ser Gly Phe
                 85                  90                  95

Ile Phe Gly Gly Gly Thr Lys Leu Thr Val Leu
            100                 105

<210> SEQ ID NO 99
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
cagatcgtgc tgacccagcc acctagcgcc tccggaaccc ctggccagcg ggtgacaatc      60
tcctgtaaga gaaacaccgg caatatcggc tctaactacg tgaattggta tcagcagctg     120
cctggcacag ccccaaagct gctgatctac cgggacgata agagacccga cggcgtgcct     180
gatagatttt ctggcagcaa gtccggcacc tctgccagcc tggccatcag cggactgcag     240
tccgaggacg aggcagatta ctattgtcag agctattcta gcggcttcat ctttggagga     300
ggaaccaagc tgacagtgct g                                               321

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Thr Gly Asn Ile Gly Ser Asn Tyr
1               5

<210> SEQ ID NO 101
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Ser Tyr Ser Ser Gly Phe Ile
1               5

<210> SEQ ID NO 102
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg Asp Asp
1
```

<210> SEQ ID NO 103
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 103

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115
```

<210> SEQ ID NO 104
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104

```
gaggtgcagc tggtggagag cggcggcggc ctggtgcagc ctggaggctc cctgcggctg      60
tcttgcgcag ccagcggcgt gacattcaac tactatggca tgagctggat cagacaggcc     120
ccaggcaagg gactggagtg ggtggcctcc atcaccaatt ctggcggcag gatctactat     180
cccgactctg tgaagggcag gtttacaatc agccgcgaga cacccagaa gacactgtac      240
ctgcagatga acagcctgcg ggccgaggat accgccgtgt actattgcac actggacggc     300
agagacggat gggtggcata ttggggacag ggcaccctgg tgacagtgag ctcc            354
```

<210> SEQ ID NO 105
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 105

```
Gly Val Thr Phe Asn Tyr Tyr Gly
1               5
```

<210> SEQ ID NO 106
<211> LENGTH: 11
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Thr Leu Asp Gly Arg Asp Gly Trp Val Ala Tyr
1               5                   10

<210> SEQ ID NO 107
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Ile Thr Asn Ser Gly Gly Arg Ile
1               5

<210> SEQ ID NO 108
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Val Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105

<210> SEQ ID NO 109
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
caggtggtgc tgacccagcc acctagcgcc tccggaaccc ctggccagcg ggtgacaatc        60
tcctgtaaga gaaacaccgg caatatcggc tctaactacg tgaattggta tcagcagctg       120
cctggcacag ccccaaagct gctgatctac cgggacgata agagacccga cggcgtgcct       180
gatagatttt ctggcagcaa gtccggcacc tctgccagcc tggccatcag cggactgcag       240

```
tccgaggacg aggcagatta ctattgtcag agctattcta gcggcttcat ctttggagga      300
ggaaccaagc tgacagtgct g                                                321
```

<210> SEQ ID NO 110
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Thr Gly Asn Ile Gly Ser Asn Tyr
1               5

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gln Ser Tyr Ser Ser Gly Phe Ile
1               5

<210> SEQ ID NO 112
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Arg Asp Asp
1

<210> SEQ ID NO 113
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
                20                  25                  30

Gly Met Ser Trp Ile Arg Gln Ala Pro Gly Lys Gly Leu Glu Trp Val
            35                  40                  45

Ala Ser Ile Thr Asn Ser Gly Gly Arg Ile Tyr Tyr Pro Asp Ser Val
        50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110
Leu Val Thr Val Ser Ser
        115

<210> SEQ ID NO 114
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
gaggtgcagc tggtggagtc tggcggcggc ctggtgcagc ctggcggcag cctgcggctg      60
tcctgcgccg cctctggcgt gaccttcaac tactatggca tgagctggat cagacaggcc     120
ccaggcaagg gactggagtg ggtggccagc atcaccaatt ccggcggcag gatctactat     180
cccgattccg tgaagggcag gtttacaatc agccgggaga cacccagaa gacactgtac      240 ctgcagatga acagcctgcg ggcagaggac accgccgtgt actattgcac actggacggc     300
agagacggat gggtggcata ttggggacag ggcacccctg gtgacagtga gctcc          354

<210> SEQ ID NO 115
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Gly Val Thr Phe Asn Tyr Tyr Gly
1               5

<210> SEQ ID NO 116
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Thr Leu Asp Gly Arg Asp Gly Trp Val Ala Tyr
1               5                   10

<210> SEQ ID NO 117
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ile Thr Asn Ser Gly Gly Arg Ile
1               5

<210> SEQ ID NO 118
<211> LENGTH: 109
<212> TYPE: PRT

<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 118

Gln Phe Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95

Gly Phe Ile Phe Gly Gly Gly Thr Lys Leu Thr Val Leu
            100                 105

<210> SEQ ID NO 119
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 119
cagttcgtgc tgacccagcc acctagcgcc tccggaaccc ctggccagcg ggtgacaatc      60
agctgtaaga gaaacacagg caatatcggc tccaactacg tgaattggta tcagcagctg     120
cctggcaccg ccccaaagac aatcatctac cggaacgaca gagacccga tggcgtgcct      180 gacagatttt ctggcagcat cgattctagc tccaattccg cctctctggc catctctggc     240
ctgcagagcg aggacgaggc cgattactat tgtcagagct attctagcgg cttcatcttt     300
ggaggaggaa ccaagctgac agtgctg                                         327

<210> SEQ ID NO 120
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 120

Thr Gly Asn Ile Gly Ser Asn Tyr
1               5

<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 121

```
Gln Ser Tyr Ser Ser Gly Phe Ile
1               5
```

<210> SEQ ID NO 122
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

```
Arg Asn Asp
1
```

<210> SEQ ID NO 123
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Arg Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115
```

<210> SEQ ID NO 124
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124

```
gaggtgcagc tggtggagtc cggaggagga ctggtgcagc tggaggctc cctgaggctg      60 tcttgcgcag ccagcggagt gacattcaac tactatggca tgagctggat cagacaggcc    120
ccaggcaagg gactggagtg gtggcctcc atcacccggt ctggcggcag aatctactat     180
cccgactctg tgaagggccg gtttacaatc agcagagaga cacccagaa gacactgtac     240 ctgcagatga acagcctgcg ggccgaggat accgccgtgt actattgcac actggacggc    300
agagatggat ggggtggcata ttggggacag ggcaccctgg tgacagtgag ctcc          354
```

<210> SEQ ID NO 125
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Val Thr Phe Asn Tyr Tyr Gly
1               5

<210> SEQ ID NO 126
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Thr Leu Asp Gly Arg Asp Gly Trp Val Ala Tyr
1               5                   10

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Ile Thr Arg Ser Gly Gly Arg Ile
1               5

<210> SEQ ID NO 128
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gln Val Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105

```
<210> SEQ ID NO 129
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
caggtggtgc tgacccagcc acctagcgcc tccggaaccc ctggccagag ggtgacaatc     60
tcctgtaagc gcaacaccgg caatatcggc tctaactacg tgaattggta tcagcagctg    120
cctggcacag ccccaaagct gctgatctac agggacgata agagacccga cggcgtgcct    180
gatcggtttt ctggcagcaa gtccggcacc tctgccagcc tggccatcag cggactgcag    240
tccgaggacg aggcagatta ctattgtcag agctattcta gcggcttcat ctttggagga    300
ggaaccaagc tgacagtgct g                                               321

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Thr Gly Asn Ile Gly Ser Asn Tyr
1               5

<210> SEQ ID NO 131
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Gln Ser Tyr Ser Ser Gly Phe Ile
1               5

<210> SEQ ID NO 132
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Arg Asp Asp
1

<210> SEQ ID NO 133
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Ser Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Glu Gly Trp Val Ala Tyr Trp Gly Gln Gly Thr
            100                 105                 110

Leu Val Thr Val Ser Ser
            115
```

```
<210> SEQ ID NO 134
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
gaggtgcagc tggtggagtc cggcggcggc ctggtgcagc caggaggctc cctgcggctg      60
tcttgcgcag ccagcggcgt gaccttcaac tactatggca tgtcctggat cagacaggcc     120
cccggcaagg gactggagtg ggtggcctct atcaccagct ccggcggcag gatctactat     180
cctgattccg tgaagggcag gtttacaatc agccgggaga cacccagaa gacactgtac      240 ctgcagatga atagcctgag ggccgaggat accgccgtgt actattgcac actggacggc     300
agagagggat gggtggcata ttggggacag ggcaccctgg tgacagtgtc tagc            354
```

```
<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Gly Val Thr Phe Asn Tyr Tyr Gly
1               5
```

```
<210> SEQ ID NO 136
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Thr Leu Asp Gly Arg Glu Gly Trp Val Ala Tyr
1               5                   10
```

<210> SEQ ID NO 137
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ile Thr Ser Ser Gly Gly Arg Ile
1               5

<210> SEQ ID NO 138
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45

Ile Tyr Arg Asn Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105

<210> SEQ ID NO 139
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 139
aacttcatgc tgacccagcc acacagcgtg tccgagtctc ccggcaagac cgtgacaatc      60
agctgtaaga gaaacacagg caatatcggc tccaactacg tgaattggta tcagcagcac     120
gagggctcct ctcctaccac aatcatctac cggaacgaca agagaccaga tggcgtgtcc     180
gaccggttca gcggctccat cgatagaagc tccaagtctg ccagcctgac catctctaat     240
ctgaagacag aggacgaggc cgattacttt tgtcagagct attctagcgg cttcatcttt     300
ggaggaggaa ccaagctgac agtgctg                                        327

<210> SEQ ID NO 140
<211> LENGTH: 8
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 140

Thr Gly Asn Ile Gly Ser Asn Tyr
1               5

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gln Ser Tyr Ser Ser Gly Phe Ile
1               5

<210> SEQ ID NO 142
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Arg Asn Asp
1

<210> SEQ ID NO 143
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Ser Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Glu Gly Trp Val Ala Tyr Trp Gly Gln Gly Thr
            100                 105                 110

Leu Val Thr Val Ser Ser
        115

<210> SEQ ID NO 144
<211> LENGTH: 354
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 144

```
gaggtgcagc tggtggagtc tggcggcggc ctggtgcagc ctggcggcag cctgcggctg      60
tcctgcgccg cctctggcgt gacattcaac tactatggca tgagctggat cagacaggcc    120
ccaggcaagg gactggagtg ggtggcctcc atcaccagct ccggcggcag gatctactat    180
cccgactctg tgaagggcag gtttacaatc agccgcgaga cacccagaa gacactgtac    240
ctgcagatga atagcctgag ggccgaggac accgccgtgt actattgcac actggatggc    300
cgcgagggat gggtggcata ttggggacag ggcaccctgg tgacagtgtc ttcc          354
```

<210> SEQ ID NO 145
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gly Val Thr Phe Asn Tyr Tyr Gly
1               5

<210> SEQ ID NO 146
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Thr Leu Asp Gly Arg Glu Gly Trp Val Ala Tyr
1               5                   10

<210> SEQ ID NO 147
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Ile Thr Ser Ser Gly Gly Arg Ile
1               5

<210> SEQ ID NO 148
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Gln Val Val Leu Thr Gln Pro Pro Ser Ala Ser Gly Thr Pro Gly Gln
1               5                   10                  15

```
Arg Val Thr Ile Ser Cys Lys Arg Asn Thr Gly Asn Ile Gly Ser Asn
             20                  25                  30

Tyr Val Asn Trp Tyr Gln Gln Leu Pro Gly Thr Ala Pro Lys Leu Leu
             35                  40                  45

Ile Tyr Arg Asp Asp Lys Arg Pro Asp Gly Val Pro Asp Arg Phe Ser
 50                  55                  60

Gly Ser Lys Ser Gly Thr Ser Ala Ser Leu Ala Ile Ser Gly Leu Gln
65                   70                  75                  80

Ser Glu Asp Glu Ala Asp Tyr Tyr Cys Gln Ser Tyr Ser Ser Gly Phe
                 85                  90                  95

Ile Phe Gly Gly Gly Thr Lys Leu Thr Val Leu
            100                 105
```

<210> SEQ ID NO 149
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 149

```
caggtggtgc tgacccagcc accttctgcc agcggaaccc ctggccagcg ggtgacaatc      60
tcctgtaaga gaaacaccgg caatatcggc tctaactacg tgaattggta tcagcagctg     120
cctggcacag ccccaaagct gctgatctac cgggacgata agagacccga cggcgtgcct     180
gatagatttt ccggctctaa gagcggcacc tccgcctctc tggccatcag cggactgcag     240
tccgaggacg aggcagatta ctattgtcag tcctattcct ctggcttcat ctttggagga     300
ggaaccaagc tgacagtgct g                                               321
```

<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

```
Thr Gly Asn Ile Gly Ser Asn Tyr
1               5
```

<210> SEQ ID NO 151
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 151

```
Gln Ser Tyr Ser Ser Gly Phe Ile
1               5
```

<210> SEQ ID NO 152
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 152

Arg Asp Asp
1

<210> SEQ ID NO 153
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Arg Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Glu Gly Trp Val Ala Tyr Trp Gly Gln Gly Thr
            100                 105                 110

Leu Val Thr Val Ser Ser
        115

<210> SEQ ID NO 154
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 154
gaggtgcagc tggtggagtc cggaggagga ctggtgcagc caggaggctc tctgaggctg      60
agctgcgcag cctccggcgt gaccttcaac tactatggca tgagctggat cagacaggcc     120
cccggcaagg gactggagtg ggtggcctct atcacccgga gcggcggcag aatctactat     180
cctgattccg tgaagggccg gtttacaatc tctagagaga cacccagaa gacactgtac      240 ctgcagatga acagcctgcg ggccgaggat accgccgtgt actattgcac actggacggc     300
agagagggat gggtggcata ttggggacag ggcacccctg tgacagtgag ctcc           354

<210> SEQ ID NO 155
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 155

```
Gly Val Thr Phe Asn Tyr Tyr Gly
1               5

<210> SEQ ID NO 156
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Thr Leu Asp Gly Arg Glu Gly Trp Val Ala Tyr
1               5                   10

<210> SEQ ID NO 157
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Ile Thr Arg Ser Gly Gly Arg Ile
1               5

<210> SEQ ID NO 158
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45

Ile Tyr Arg Asn Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105

<210> SEQ ID NO 159
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159
```

```
aacttcatgc tgacccagcc acactccgtg tctgagagcc ccggcaagac cgtgacaatc    60
agctgtaagc ggaacacagg caatatcggc tccaactacg tgaattggta tcagcagcac   120
gagggctcta gccctaccac aatcatctac aggaacgaca gcgcccaga tggcgtgagc    180 gacaggttct ccggctctat cgatcgctcc tctaagagcg cctccctgac catctctaat   240
ctgaagacag aggacgaggc cgattacttt tgtcagagct atagctccgg cttcatcttt   300
ggaggaggaa ccaagctgac agtgctg                                       327
```

```
<210> SEQ ID NO 160
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160
```

Thr Gly Asn Ile Gly Ser Asn Tyr
1               5

```
<210> SEQ ID NO 161
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161
```

Gln Ser Tyr Ser Ser Gly Phe Ile
1               5

```
<210> SEQ ID NO 162
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162
```

Arg Asn Asp
1

```
<210> SEQ ID NO 163
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
                20                  25                  30

Gly Met Ser Trp Ile Arg Gln Ala Pro Gly Lys Gly Leu Glu Trp Val
            35                  40                  45

Ala Ser Ile Thr Asn Ser Gly Gly Arg Ile Tyr Tyr Pro Asp Ser Val

```
                    50                  55                  60
Lys Gly Arg Phe Thr Ile Ser Arg Glu Asn Thr Gln Lys Thr Leu Tyr
 65                  70                  75                  80

Leu Gln Met Asn Ser Leu Arg Ala Glu Asp Thr Ala Val Tyr Tyr Cys
                 85                  90                  95

Thr Leu Asp Gly Arg Glu Gly Trp Val Ala Tyr Trp Gly Gln Gly Thr
            100                 105                 110

Leu Val Thr Val Ser Ser
            115

<210> SEQ ID NO 164
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
gaggtgcagc tggtggagtc cggcggcggc ctggtgcagc caggaggctc tctgcggctg    60
agctgcgcag cctccggcgt gaccttcaac tactatggca tgagctggat cagacaggcc   120
cccggcaagg gcctggagtg ggtggcctct atcaccaata gcggcggcag gatctactat   180
cctgactccg tgaagggcag gtttacaatc agcggggaga cacccagaa gacactgtac    240 ctgcagatga acagcctgcg ggcagaggac accgccgtgt actattgcac actggatggc   300
cgcgagggat gggtggcata ttggggacag ggcaccctgg tgacagtgag ctcc         354

<210> SEQ ID NO 165
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gly Val Thr Phe Asn Tyr Tyr Gly
 1               5

<210> SEQ ID NO 166
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Thr Leu Asp Gly Arg Glu Gly Trp Val Ala Tyr
 1               5                  10

<210> SEQ ID NO 167
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167
```

```
<210> SEQ ID NO 168
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45

Ile Tyr Arg Asp Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105

<210> SEQ ID NO 169
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169
aactttatgc tgacccagcc acactccgtg tctgagagcc ccggcaagac cgtgacaatc     60
agctgtaaga gaaacacagg caatatcggc tccaactacg tgaattggta tcagcagcac    120
gagggctcta gccctaccac aatcatctac cgggacgata gcggcccga cggcgtgagc     180 gatcggttct ccggctctat cgacagatcc tctaagagcg cctccctgac catctctaat    240
ctgaagacag aggacgaggc cgattacttt tgtcagagct atagctccgg cttcatcttt    300
ggaggaggaa ccaagctgac agtgctg                                         327

<210> SEQ ID NO 170
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Thr Gly Asn Ile Gly Ser Asn Tyr
1               5

<210> SEQ ID NO 171
<211> LENGTH: 8
```

<210> SEQ ID NO 172
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gln Ser Tyr Ser Ser Gly Phe Ile
1               5

<210> SEQ ID NO 172
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Arg Asp Asp
1

<210> SEQ ID NO 173
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Arg Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Glu Gly Trp Val Ala Tyr Trp Gly Gln Gly Thr
            100                 105                 110

Leu Val Thr Val Ser Ser
        115

<210> SEQ ID NO 174
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
gaggtgcagc tggtggagtc cggaggagga ctggtgcagc ctggaggctc cctgaggctg    60
tcttgcgcag ccagcggagt gacattcaac tactatggca tgagctggat cagacaggcc   120

```
ccaggcaagg gactggagtg ggtggcctcc atcacccggt ctggcggcag aatctactat    180
cccgactctg tgaagggccg gtttacaatc agcagagaga acacccagaa gacactgtac    240
ctgcagatga acagcctgcg ggcagaggac accgccgtgt actattgcac actggatggc    300
agagagggat gggtggcata ttggggacag ggcaccctgg tgacagtgag ctcc          354
```

```
<210> SEQ ID NO 175
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gly Val Thr Phe Asn Tyr Tyr Gly
1               5

<210> SEQ ID NO 176
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Thr Leu Asp Gly Arg Glu Gly Trp Val Ala Tyr
1               5                   10

<210> SEQ ID NO 177
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ile Thr Arg Ser Gly Gly Arg Ile
1               5

<210> SEQ ID NO 178
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gln Val Val Leu Thr Gln Pro Pro Ser Ala Ser Gly Thr Pro Gly Gln
1               5                   10                  15

Arg Val Thr Ile Ser Cys Lys Arg Asn Thr Gly Asn Ile Gly Ser Asn
                20                  25                  30

Tyr Val Asn Trp Tyr Gln Gln Leu Pro Gly Thr Ala Pro Lys Leu Leu
            35                  40                  45

Ile Tyr Arg Asp Asp Lys Arg Pro Asp Gly Val Pro Asp Arg Phe Ser
        50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Gln Ser Tyr Ser Ser Gly Phe
             85                  90                  95
Ile Phe Gly Gly Gly Thr Lys Leu Thr Val Leu
            100                 105
```

<210> SEQ ID NO 179
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 179

```
caggtggtgc tgacccagcc acctagcgcc tccggaaccc ctggccagag ggtgacaatc    60
tcctgtaagc gcaacaccgg caatatcggc tctaactacg tgaattggta tcagcagctg   120
cctggcacag ccccaaagct gctgatctac agggacgata agagacccga cggcgtgcct   180
gatcggtttt ctggcagcaa gtccggcacc tctgccagcc tggccatcag cggactgcag   240
tccgaggacg aggcagatta ctattgtcag agctattcta gcggcttcat ctttggagga   300
ggaaccaagc tgacagtgct g                                             321
```

<210> SEQ ID NO 180
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 180

```
Thr Gly Asn Ile Gly Ser Asn Tyr
1               5
```

<210> SEQ ID NO 181
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 181

```
Gln Ser Tyr Ser Ser Gly Phe Ile
1               5
```

<210> SEQ ID NO 182
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 182

```
Arg Asp Asp
1
```

<210> SEQ ID NO 183
<211> LENGTH: 118

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Val | Thr | Phe | Asn | Tyr | Tyr |
|---|---|---|---|---|---|---|---|---|---|---|---|---|---|---|---|
| | | | 20 | | | | | 25 | | | | | 30 | | |

| Gly | Met | Ser | Trp | Ile | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ser | Ile | Thr | Asn | Ser | Gly | Gly | Arg | Ile | Tyr | Tyr | Pro | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Glu | Asn | Thr | Gln | Lys | Thr | Leu | Tyr |
|---|---|---|---|---|---|---|---|---|---|---|---|---|---|---|---|
| 65 | | | | 70 | | | | | 75 | | | | | 80 | |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | 85 | | | | | 90 | | | | | 95 | | |

| Thr | Leu | Asp | Gly | Arg | Asp | Gly | Trp | Val | Ala | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser |
|---|---|---|---|---|---|
| | | | 115 | | |

```
<210> SEQ ID NO 184
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
gaggtgcagc tggtggagtc cggcggcggc ctggtgcagc ctggaggctc cctgaggctg      60
tcttgcgcag ccagcggagt gaccttcaac tactatggca tgtcctggat cagacaggcc     120
ccaggcaagg gactggagtg ggtggcctcc atcaccaatt ctggcggcag aatctactat     180
cccgattctg tgaagggcag gtttacaatc agccgcgaga cacccagaa gacactgtac      240 ctgcagatga atagcctgcg ggcagaggac accgccgtgt actattgcac actggacggc     300
agagatggat gggtggcata ttggggacag ggcaccctgg tgacagtgag ctcc           354

<210> SEQ ID NO 185
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185
```

| Gly | Val | Thr | Phe | Asn | Tyr | Tyr | Gly |
|---|---|---|---|---|---|---|---|
| 1 | | | | 5 | | | |

```
<210> SEQ ID NO 186
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 186

Thr Leu Asp Gly Arg Asp Gly Trp Val Ala Tyr
1               5                   10

<210> SEQ ID NO 187
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Ile Thr Asn Ser Gly Gly Arg Ile
1               5

<210> SEQ ID NO 188
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Thr Ile
        35                  40                  45

Ile Tyr Arg Asn Asp Lys Arg Pro Asp Gly Val Pro Asp Arg Phe Ser
    50                  55                  60

Gly Ser Ile Asp Ser Ser Asn Ser Ala Ser Leu Ala Ile Ser Gly
65                  70                  75                  80

Leu Gln Ser Glu Asp Glu Ala Asp Tyr Tyr Cys Gln Ser Tyr Ser Ser
                85                  90                  95

Gly Phe Ile Phe Gly Gly Gly Thr Lys Leu Thr Val Leu
            100                 105

<210> SEQ ID NO 189
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189
aacttcatgc tgacccagcc ccacagcgtg tccgagtctc ctggcaagac cgtgacaatc      60
tcctgtaagc gcaacacagg caatatcggc tctaactacg tgaattggta tcagcagctg     120
ccaggcaccg cccccaagac aatcatctac cggaacgaca agagacctga tggcgtgcca     180
gaccggttta gcggctccat cgattctagc tccaattctg ccagcctggc catcagcgga     240
ctgcagtccg aggacgaggc agattactat tgtcagtcct attctagcgg cttcatcttt     300
ggaggaggaa ccaagctgac agtgctg                                         327
```

<210> SEQ ID NO 190
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Thr Gly Asn Ile Gly Ser Asn Tyr
1               5

<210> SEQ ID NO 191
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Gln Ser Tyr Ser Ser Gly Phe Ile
1               5

<210> SEQ ID NO 192
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Arg Asn Asp
1

<210> SEQ ID NO 193
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 193

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ser Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Val Leu Pro Pro Ser Arg Asp Glu Leu Thr
        130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 194
<211> LENGTH: 693
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194
gaacctaaaa gcagcgacaa gacccacaca tgcccaccct gtccggcgcc agaggccgcc      60
ggaggaccat ccgtgttcct gtttccaccc aagcccaagg ataccctgat gatctctcgg     120
acccctgagg tgacatgcgt ggtggtgagc gtgtcccacg aggacccaga ggtgaagttc     180
aactggtacg tggatggcgt ggaggtgcac aatgccaaga caaagccccg ggaggagcag     240
tacaactcta cctatagagt ggtgagcgtg ctgacagtgc tgcaccagga ctggctgaac     300
ggcaaggagt ataagtgtaa ggtgtccaat aaggccctgc ccgcccctat cgagaaaact     360
atcagcaaag ccaagggcca gccaagggaa ccacaggtct atgtcctgcc accatctcgc     420
gacgagctga ccaagaacca ggtctcactg ctgtgtctgg tgaaaggatt ctatccttcc     480
gatattgccg tggagtggga atctaatggc cagccagaga caattacct gacctggccc      540 cctgtgctgg acagcgatgg gtccttcttt ctgtattcaa agctgacagt ggacaaaagc     600
agatggcagc agggaaacgt ctttagctgt tccgtgatgc acgaagccct gcacaatcat     660
tacacccaga gtctctgag tctgtcacct ggc                                    693

<210> SEQ ID NO 195
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser Val Ser His Glu Asp Pro Glu Val Lys Phe Asn Trp Tyr

```
                35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 196
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
gcgccagagg ccgccggagg accatccgtg ttcctgtttc cacccaagcc caaggatacc     60
ctgatgatct ctcggacccc tgaggtgaca tgcgtggtgg tgagcgtgtc ccacgaggac    120
ccagaggtga agttcaactg gtacgtggat ggcgtggagg tgcacaatgc caagacaaag    180 cccc gggagg agcagtacaa ctctacctat agagtggtga gcgtgctgac agtgctgcac    240
caggactggc tgaacggcaa ggagtataag tgtaaggtgt ccaataaggc cctgcccgcc    300
cctatcgaga aaactatcag caaagccaag                                      330

<210> SEQ ID NO 197
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Gly Gln Pro Arg Glu Pro Gln Val Tyr Val Leu Pro Pro Ser Arg Asp
  1               5                  10                  15

Glu Leu Thr Lys Asn Gln Val Ser Leu Leu Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Leu Thr Trp Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 198
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 198

```
ggccagccaa gggaaccaca ggtctatgtc ctgccaccat ctcgcgacga gctgaccaag    60
aaccaggtct cactgctgtg tctggtgaaa ggattctatc cttccgatat tgccgtggag   120
tgggaatcta atggccagcc agagaacaat tacctgacct ggccccctgt gctggacagc   180
gatgggtcct tctttctgta ttcaaagctg acagtggaca aaagcagatg gcagcaggga   240
aacgtcttta gctgttccgt gatgcacgaa gccctgcaca tcattacac ccagaagtct   300 ctgagtctgt cacctggc                                                  318
```

<210> SEQ ID NO 199
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 199

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ser Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 200
<211> LENGTH: 693
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 200

```
gagccaaaga gctccgacaa gacccacaca tgcccccctt gtccggcgcc agaggcagca    60
ggaggaccaa gcgtgttcct gtttccaccc aagcccaaag acaccctgat gattagccga   120
acccctgaag tcacatgcgt ggtcgtgtcc gtgtctcacg aggacccaga agtcaagttc   180
aactggtacg tggatggcgt cgaggtgcat aatgccaaga caaaaccccg ggaggaacag   240
tacaacagca cctatagagt cgtgtccgtc ctgacagtgc tgcaccagga ttggctgaac   300
ggcaaggaat ataagtgcaa agtgtccaat aaggccctgc ccgctcctat cgagaaaacc   360
atttctaagg caaaaggcca gcctcgcgaa ccacaggtct acgtgctgcc tccatcccgg   420
gacgagctga caaagaacca ggtctctctg ctgtgcctgg tgaaaggctt ctatccatca   480
gatattgctg tggagtggga aagcaatggg cagcccgaga caattacct gacttggccc   540
cctgtgctgg actctgatgg gagtttcttt ctgtattcta agctgaccgt ggataaaagt   600
aggtggcagc agggaaatgt ctttagttgt cagtgatgc atgaagccct gcataaccac   660
tacacccaga aaagcctgtc cctgtccccc gga                                693
```

<210> SEQ ID NO 201
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 202
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202

```
gcgccagagg cagcaggagg accaagcgtg ttcctgtttc cacccaagcc caaagacacc    60
ctgatgatta gccgaacccc tgaagtcaca tgcgtggtcg tgtccgtgtc tcacgaggac   120
```

```
ccagaagtca agttcaactg gtacgtggat ggcgtcgagg tgcataatgc caagacaaaa      180
ccccgggagg aacagtacaa cagcacctat agagtcgtgt ccgtcctgac agtgctgcac      240
caggattggc tgaacggcaa ggaatataag tgcaaagtgt ccaataaggc cctgcccgct      300
cctatcgaga aaaccatttc taaggcaaaa                                      330
```

<210> SEQ ID NO 203
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

```
Gly Gln Pro Arg Glu Pro Gln Val Tyr Val Leu Pro Pro Ser Arg Asp
1               5                  10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 204
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 204

```
ggccagcctc gcgaaccaca ggtctacgtg ctgcctccat cccgggacga gctgacaaag       60
aaccaggtct ctctgctgtg cctggtgaaa ggcttctatc catcagatat tgctgtggag      120
tgggaaagca atgggcagcc cgagaacaat tacctgactt ggccccctgt gctggactct      180
gatgggagtt tctttctgta ttctaagctg accgtggata aaagtaggtg gcagcaggga      240
aatgtcttta gttgttcagt gatgcatgaa gccctgcata accactacac ccagaaaagc      300
ctgtccctgt ccccggga                                                   318
```

<210> SEQ ID NO 205
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (37)..(37)
<223> OTHER INFORMATION: a, c, t, g, unknown or other

```
<400> SEQUENCE: 205
gctagcgcta ccggactcag atcccccccc ccccdn                              37

<210> SEQ ID NO 206
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
ttccacatca ctcgggtaga aatcag                                         26

<210> SEQ ID NO 207
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
taacaccagg gtagaaatct gtcaccat                                       28

<210> SEQ ID NO 208
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
ctggctcagg gaaatagcc                                                 19

<210> SEQ ID NO 209
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209
tccctggagc tcctcagt                                                  18

<210> SEQ ID NO 210
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210
gccttgtcag tcttgagc                                                  18

<210> SEQ ID NO 211
<211> LENGTH: 354
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 211
gaggtgcagt tggtggagtc tgggggaggc ctggtgcagc ctggaagggc cctgaaactc    60
tcctgtgtag tctctggagt cacattcaat tactacggga tgagctggat ccgccaggct   120
ccagggaagg ggctggagtg ggttgcatcc attactaatt ctggtggtag aatttactat   180
ccagactctg tgaagggccg attcactatc tccagagaaa atacacaaaa gaccctatac   240
ctacaaatga acagtctgag gtctgaggac acggccactt attactgtac tctcgatggt   300
cgcgatggtt gggttgctta ctggggccaa ggcactctgg tcactgtctc ttca         354

<210> SEQ ID NO 212
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Glu Val Gln Leu Val Glu Ser Gly Gly Gly Leu Val Gln Pro Gly Arg
1               5                   10                  15

Ala Leu Lys Leu Ser Cys Val Val Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ser Glu Asp Thr Ala Thr Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115

<210> SEQ ID NO 213
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
cagtttgtgc ttactcagcc aaactctgtg tctacgaatc tcggaaccac agtcgaactg    60
tcttgcaagc gcaacactgg gaacattgga agcaattatg tgaactggta ccagcagcat   120
gagggaagat ctcccaccac tattatttat gggatgataa gagaccagat ggagtttct    180 gacaggttct ctgggtccat tgacagatct tccaagtcag ccctcctgac aatcaataat   240
gtgcagactg aagatgaagc tgactacttc tgtcagtctt acagtagtgg ttttatttc    300 ggcggtggaa ccaagctcac tgtccta                                        327

<210> SEQ ID NO 214
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 214

```
Gln Phe Val Leu Thr Gln Pro Asn Ser Val Ser Thr Asn Leu Gly Thr
1               5                   10                  15
Thr Val Glu Leu Ser Cys Lys Arg Asn Thr Gly Asn Ile Gly Ser Asn
            20                  25                  30
Tyr Val Asn Trp Tyr Gln Gln His Glu Gly Arg Ser Pro Thr Thr Ile
        35                  40                  45
Ile Tyr Arg Asp Asp Lys Arg Pro Asp Gly Val Ser Asp Arg Phe Ser
    50                  55                  60
Gly Ser Ile Asp Arg Ser Ser Lys Ser Ala Leu Leu Thr Ile Asn Asn
65                  70                  75                  80
Val Gln Thr Glu Asp Glu Ala Asp Tyr Phe Cys Gln Ser Tyr Ser Ser
                85                  90                  95
Gly Phe Ile Phe Gly Gly Gly Thr Lys Leu Thr Val Leu
            100                 105
```

<210> SEQ ID NO 215
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
gtcactgtct cttcaggtgg aggcggttca ggcggaggtg gcagcggcgg tggcgggagt    60
cagtttgtgc ttact    75

<210> SEQ ID NO 216
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
agtaagcaca aactgactcc cgccaccgcc gctgccacct ccgcctgaac cgcctccacc    60
tgaagagaca gtgac    75

<210> SEQ ID NO 217
<211> LENGTH: 867
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 217
atgaaacacc tgtggttctt cctcctgctg gtggcagctc ccagatgggt gctgagcgag    60

| | | |
|---|---|---|
| gtgcagttgg tggagtctgg gggaggcctg gtgcagcctg gaagggccct gaaactctcc | 120 | |
| tgtgtagtct ctggagtcac attcaattac tacgggatga gctggatccg ccaggctcca | 180 | |
| gggaagggc tggagtgggt tgcatccatt actaattctg gtggtagaat ttactatcca | 240 | |
| gactctgtga agggccgatt cactatctcc agagaaaata cacaaaagac cctataccta | 300 | |
| caaatgaaca gtctgaggtc tgaggacacg gccacttatt actgtactct cgatggtcgc | 360 | |
| gatggttggg ttgcttactg gggccaaggc actctggtca ctgtctcttc aggtggaggc | 420 | |
| ggttcaggcg gaggtggcag cggcggtggc gggagtcagt ttgtgcttac tcagccaaac | 480 | |
| tctgtgtcta cgaatctcgg aaccacagtc gaactgtctt gcaagcgcaa cactgggaac | 540 | |
| attggaagca attatgtgaa ctggtaccag cagcatgagg aagatctccc caccactatt | 600 | |
| atttataggg atgataagag accagatgga gtttctgaca ggttctctgg gtccattgac | 660 | |
| agatcttcca agtcagccct cctgacaatc aataatgtgc agactgaaga tgaagctgac | 720 | |
| tacttctgtc agtcttacag tagtggtttt attttcggcg gtggaaccaa gctcactgtc | 780 | |
| ctaggcgcgt ctgcggccgc aggatccggt ggtgattaca agatgatga cgataaaggt | 840 | |
| gcagcggcgc atcaccatca tcaccac | 867 | |

<210> SEQ ID NO 218
<211> LENGTH: 270
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Glu Val Gln Leu Val Glu Ser Gly Gly Gly Leu Val Gln Pro Gly Arg
1               5                   10                  15

Ala Leu Lys Leu Ser Cys Val Val Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ser Glu Asp Thr Ala Thr Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser Gly Gly Gly Ser Gly Gly Gly Gly Gly Ser
        115                 120                 125

Gly Gly Gly Gly Ser Gln Phe Val Leu Thr Gln Pro Asn Ser Val Ser
    130                 135                 140

Thr Asn Leu Gly Thr Thr Val Glu Leu Ser Cys Lys Arg Asn Thr Gly
145                 150                 155                 160

Asn Ile Gly Ser Asn Tyr Val Asn Trp Tyr Gln Gln His Glu Gly Arg
                165                 170                 175

Ser Pro Thr Thr Ile Ile Tyr Arg Asp Asp Lys Arg Pro Asp Gly Val
            180                 185                 190

Ser Asp Arg Phe Ser Gly Ser Ile Asp Arg Ser Ser Lys Ser Ala Leu
        195                 200                 205

```
Leu Thr Ile Asn Asn Val Gln Thr Glu Asp Glu Ala Asp Tyr Phe Cys
    210                 215                 220

Gln Ser Tyr Ser Ser Gly Phe Ile Phe Gly Gly Gly Thr Lys Leu Thr
225                 230                 235                 240

Val Leu Gly Ala Ser Ala Ala Ala Gly Ser Gly Gly Asp Tyr Lys Asp
                245                 250                 255

Asp Asp Asp Lys Gly Ala Ala Ala His His His His His His
                260                 265                 270
```

<210> SEQ ID NO 219
<211> LENGTH: 864
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219

```
atgaaacacc tgtggttctt cctcctgctg gtggcagctc ccagatgggt gctgagcgga    60
gaagtgcagc tggtggaatc cgggggggc ctggtgcagc ctgggggag cctgagactg    120
agttgtgccg cctctggggt gacatttaac tactatggca tgtcttggat ccgccaggca    180
cctggaaagg gcctggagtg ggtggccagc atcactaatt ccggcgggcg aatctactat    240
cccgacagcg tcaagggcag gttcacaatt tcccgcgaga acacacagaa aactctgtac    300
ctgcagatga atagcctgag agccgaagat acagctgtgt actattgcac tctggacggc    360
agggatgggt gggtcgccta ttgggggcag ggaaccctgg tgacagtcag ctccggagga    420
ggaggatctg cggaggagg cagtggggga ggcgggtcaa actttatgct gacccagccc    480
cacagtgtgt cagagagccc tggcaagact gtcaccatct cttgtaaaag gaacaccgga    540
aatattggca gtaactacgt gaattggtat cagcagcatg aagggtctag tccaaccaca    600
atcatctacc gggacgataa agacccgac ggggtgtccg atcgattctc cggatctatc    660
gaccggtcaa gcaagagtgc ttcactgacc attagcaatc tgaaaacaga ggacgaagca    720
gattactttt gccagtccta ttcctctggc ttcatctttg gaggcgggac taaactgacc    780
gtgctgggcg cggccgcagg tgcaggtggt gattacaaag atgatgacga taaaggtgca    840
gcggcgcatc accatcatca ccac                                          864
```

<210> SEQ ID NO 220
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 220

```
Gln Phe Val Leu Tyr Gln Pro Asn Ser Val Ser Thr Asn Leu Gly Thr
1               5                   10                  15

Thr Val Glu Leu Ser Cys Lys Arg Asn Thr Gly Asn Ile Gly Ser Asn
                20                  25                  30

Tyr Val Asn Trp Tyr Gln Gln His Glu Gly Arg Ser Pro Thr Thr Ile
            35                  40                  45

Ile Tyr Arg Asp Asp Lys Arg Pro Asp Gly Val Ser Asp Arg Phe Ser
        50                  55                  60

Gly Ser Ile Asp Arg Ser Ser Lys Ser Ala Leu Leu Thr Ile Asn Asn
```

```
                65                  70                  75                  80
Val Gln Thr Glu Asp Glu Ala Asp Tyr Phe Cys Gln Ser Tyr Ser Ser
                    85                  90                  95

Gly Phe Ile Phe Gly Gly Gly Thr Lys Leu Thr Val Leu
                100                 105
```

<210> SEQ ID NO 221
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Leu Thr Val Leu
                100                 105                 110
```

<210> SEQ ID NO 222
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

```
Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Phe Gly Gly Gly Thr Lys Leu Thr Val Leu
                100                 105
```

<210> SEQ ID NO 223
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Asp Gly Tyr Asn Tyr Phe Asp Tyr Trp Gly Gln Gly Thr
            100                 105                 110

Leu Val Thr Val Ser Ser
        115

<210> SEQ ID NO 224
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 224

Gly Gly Gly Gly Ser Gly Gly Gly Ser Gly Gly Gly Gly Ser
1               5                   10                  15

<210> SEQ ID NO 225
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 225

Gly Gly Gly Gly Ser Gly Gly Gly Ser Gly Gly Gly Gly Ser Gly
1               5                   10                  15

Gly Gly Gly Ser
            20

<210> SEQ ID NO 226
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 226

Ser Ser Thr Gly Gly Gly Ser Gly Gly Gly Ser Gly Gly Gly
1               5                   10                  15

Gly Ser Asp Ile
            20

<210> SEQ ID NO 227
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Val Glu Gly Gly Ser Gly Gly Ser Gly Gly Ser Gly Gly Ser Gly Gly
1               5                   10                  15

Val Asp

<210> SEQ ID NO 228
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Gly Ser Thr Ser Gly Gly Gly Ser Gly Gly Ser Gly Gly Gly Gly
1               5                   10                  15

Ser Ser

<210> SEQ ID NO 229
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Gly Ser Thr Ser Gly Ser Gly Lys Pro Gly Ser Gly Glu Gly Ser Thr
1               5                   10                  15

Lys Gly

<210> SEQ ID NO 230
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(50)
<223> OTHER INFORMATION: /note="This sequence may encompass 1-10 'Gly
      Gly Gly Gly Ser' repeating units"

<400> SEQUENCE: 230

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
        35                  40                  45

```
Gly Ser
    50

<210> SEQ ID NO 231
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(50)
<223> OTHER INFORMATION: /note="This sequence may encompass 1-10 'Ser
      Gly Gly Gly Gly' repeating units"

<400> SEQUENCE: 231

Ser Gly Gly Gly Gly Ser Gly Gly Gly Ser Gly Gly Gly Gly Ser
1               5                   10                  15

Gly Gly Gly Gly Ser Gly Gly Gly Ser Gly Gly Gly Ser Gly
            20                  25                  30

Gly Gly Gly Ser Gly Gly Gly Ser Gly Gly Gly Ser Gly Gly
        35                  40                  45

Gly Gly
    50

<210> SEQ ID NO 232
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (5)..(54)
<223> OTHER INFORMATION: /note="This region may encompass 1-10 'Ser Gly
      Gly Gly Gly' repeating units"

<400> SEQUENCE: 232

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly
    50

<210> SEQ ID NO 233
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (3)..(32)
<223> OTHER INFORMATION: /note="This region may encompass 1-10 'Ser Gly'
      repeating units"

<400> SEQUENCE: 233
```

```
Gly Gly Ser Gly Gly Ser Gly Gly Ser Gly Gly Ser Gly
1               5                   10                  15

Gly Ser Gly Gly Ser Gly Gly Ser Gly Gly Ser Gly Gly
            20                  25                  30

<210> SEQ ID NO 234
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Gly Gly Gly Gly Ser
1               5

<210> SEQ ID NO 235
<211> LENGTH: 75
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(75)
<223> OTHER INFORMATION: /note="This sequence may encompass 1-15 'Gly
      Gly Gly Gly Ser' repeating units"
<220> FEATURE:
<221> NAME/KEY: source
<223> OTHER INFORMATION: /note="See specification as filed for detailed
      description of substitutions and preferred embodiments"

<400> SEQUENCE: 235

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly Ser Gly Gly Gly Ser Gly Gly Gly Gly
    50                  55                  60

Ser Gly Gly Gly Gly Ser Gly Gly Gly Ser
65                  70                  75

<210> SEQ ID NO 236
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xhis tag"

<400> SEQUENCE: 236

His His His His His His
1               5

<210> SEQ ID NO 237
<211> LENGTH: 25
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 237
tttttttttt tttttttttt ttttt                                              25

<210> SEQ ID NO 238
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Glu Pro Lys Ser Cys Asp Lys Thr His Thr Cys Pro Pro Cys Pro
1               5                   10                  15

<210> SEQ ID NO 239
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gagcccaaga gctgtgataa gacccacacc tgccctccct gtcca                        45

<210> SEQ ID NO 240
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ala Ala Glu Pro Lys Ser Ser Asp Lys Thr His Thr Cys Pro Pro Cys
1               5                   10                  15

Pro

<210> SEQ ID NO 241
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gcagccgaac ccaaatcctc tgataagacc cacacatgcc ctccatgtcc a                 51

<210> SEQ ID NO 242
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242
```

Glu Pro Lys Ser Ser Asp Lys Thr His Thr Cys Pro Pro Cys Pro
1               5                   10                  15

<210> SEQ ID NO 243
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gagcctaaaa gctccgacaa gacccacaca tgcccacctt gtccg            45

<210> SEQ ID NO 244
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Asp Lys Thr His Thr Cys Pro Pro Cys Pro
1               5                   10

<210> SEQ ID NO 245
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gacaagaccc acacatgccc accttgtccg                             30

<210> SEQ ID NO 246
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Gly Thr Cys Pro Pro Cys Pro
1               5

<210> SEQ ID NO 247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ggcacatgcc ctccatgtcc a                                      21

COMPOSITIONS INCLUDING CD3 ANTIGEN BINDING FRAGMENTS AND USES THEREOF

RELATED APPLICATION

This application is the U.S. National Stage of PCT/IB2019/055228, filed Jun. 20, 2019, which claims priority under 35 U.S.C. § 119(e) to U.S. Provisional Application 62/687,967 filed Jun. 21, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 16, 2020, is named 098065-0282_SL.txt and is 129,610 bytes in size.

TECHNICAL FIELD

The present technology relates generally to the preparation of immunoglobulin-related compositions (e.g., antibodies or antigen binding fragments thereof) that specifically bind CD3 and uses of the same.

BACKGROUND

The following description of the background of the present technology is provided simply as an aid in understanding the present technology and is not admitted to describe or constitute prior art to the present technology.

The development of multivalent and multispecific therapeutic proteins with favorable pharmacokinetics and functional activity has been a challenge.

Bi-specific antibodies capable of targeting and recruiting T cells to tumor cells have been identified and tested for their efficacy in the treatment of cancers. Blinatumomab is an example of a bi-specific anti-CD3-CD19 antibody in a format called BiTE™ (Bi-specific T-cell Engager) that has been identified for the treatment of B-cell diseases such as relapsed B-cell non-Hodgkin lymphoma and chronic lymphocytic leukemia (Baeuerle et al., 12:4941-4944 (2009)). The BiTE™ format is a bi-specific single chain antibody construct that links variable domains derived from two different antibodies. Blinatumomab, however, possesses poor half-life in vivo, and is difficult to manufacture in terms of production and stability.

Thus, there is an urgent need for improved bi-specific antibodies, capable of targeting T-cells to tumor cells and having improved manufacturability.

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of GVTFNYYG (SEQ ID NO: 3), a $V_H$-CDR2 sequence selected from the group consisting of ITRSGGRI (SEQ ID NO: 5) and ITSSGGRI (SEQ ID NO: 14), and a $V_H$-CDR3 sequence of TLDGRDGWVAY (SEQ ID NO: 4) or TLDGREGWVAY (SEQ ID NO: 156); and/or (b) the $V_L$ comprises a $V_L$-CDR1 sequence of: TGNIGSNY (SEQ ID NO: 7), a $V_L$-CDR2 sequence of RND (SEQ ID NO: 9), and a $V_L$-CDR3 sequence of: QSYSSGFI (SEQ ID NO: 8).

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence, a $V_H$-CDR2 sequence, and a $V_H$-CDR3 sequence of SEQ ID NO: 155, SEQ ID NO: 157, and SEQ ID NO: 156 respectively, and the $V_L$ comprises a $V_L$-CDR1 sequence, a $V_L$-CDR2 sequence, and a $V_L$-CDR3 sequence of SEQ ID NO: 160, SEQ ID NO: 162, and SEQ ID NO: 161 respectively; (b) the $V_H$ comprises a $V_H$-CDR1 sequence, a $V_H$-CDR2 sequence, and a $V_H$-CDR3 sequence of SEQ ID NO: 115, SEQ ID NO: 117, and SEQ ID NO: 116 respectively, and the $V_L$ comprises a $V_L$-CDR1 sequence, a $V_L$-CDR2 sequence, and a $V_L$-CDR3 sequence of SEQ ID NO: 120, SEQ ID NO: 122, and SEQ ID NO: 121 respectively; (c) the $V_H$ comprises a $V_H$-CDR1 sequence, a $V_H$-CDR2 sequence, and a $V_H$-CDR3 sequence of SEQ ID NO: 185, SEQ ID NO: 187, and SEQ ID NO: 186 respectively, and the $V_L$ comprises a $V_L$-CDR1 sequence, a $V_L$-CDR2 sequence, and a $V_L$-CDR3 sequence of SEQ ID NO: 190, SEQ ID NO: 192, and SEQ ID NO: 191 respectively; (d) the $V_H$ comprises a $V_H$-CDR1 sequence, a $V_H$-CDR2 sequence, and a $V_H$-CDR3 sequence of SEQ ID NO: 135, SEQ ID NO: 137, and SEQ ID NO: 136 respectively, and the $V_L$ comprises a $V_L$-CDR1 sequence, a $V_L$-CDR2 sequence, and a $V_L$-CDR3 sequence of SEQ ID NO: 140, SEQ ID NO: 142, and SEQ ID NO: 141 respectively; (e) the $V_H$ comprises a $V_H$-CDR1 sequence, a $V_H$-CDR2 sequence, and a $V_H$-CDR3 sequence of SEQ ID NO: 175, SEQ ID NO: 177, and SEQ ID NO: 176 respectively, and the $V_L$ comprises a $V_L$-CDR1 sequence, a $V_L$-CDR2 sequence, and a $V_L$-CDR3 sequence of SEQ ID NO: 180, SEQ ID NO: 182, and SEQ ID NO: 181 respectively; (f) the $V_H$ comprises a $V_H$-CDR1 sequence, a $V_H$-CDR2 sequence, and a $V_H$-CDR3 sequence of SEQ ID NO: 145, SEQ ID NO: 147, and SEQ ID NO: 146 respectively, and the $V_L$ comprises a $V_L$-CDR1 sequence, a $V_L$-CDR2 sequence, and a $V_L$-CDR3 sequence of SEQ ID NO: 150, SEQ ID NO: 152, and SEQ ID NO: 151 respectively; (g) the $V_H$ comprises a $V_H$-CDR1 sequence, a $V_H$-CDR2 sequence, and a $V_H$-CDR3 sequence of SEQ ID NO: 125, SEQ ID NO: 127, and SEQ ID NO: 126 respectively, and the $V_L$ comprises a $V_L$-CDR1 sequence, a $V_L$-CDR2 sequence, and a $V_L$-CDR3 sequence of SEQ ID NO: 130, SEQ ID NO: 132, and SEQ ID NO: 131 respectively; (h) the $V_H$ comprises a $V_H$-CDR1 sequence, a $V_H$-CDR2 sequence, and a $V_H$-CDR3 sequence of SEQ ID NO: 65, SEQ ID NO: 67, and SEQ ID NO: 66 respectively, and the $V_L$ comprises a $V_L$-CDR1 sequence, a $V_L$-CDR2 sequence, and a $V_L$-CDR3 sequence of SEQ ID NO: 70, SEQ ID NO: 72, and SEQ ID NO: 71 respectively; or (i) the $V_H$ comprises a $V_H$-CDR1 sequence, a $V_H$-CDR2 sequence, and a $V_H$-CDR3 sequence of SEQ ID NO: 165, SEQ ID NO: 167, and SEQ ID NO: 166 respectively, and the $V_L$ comprises a $V_L$-CDR1 sequence, a $V_L$-CDR2 sequence, and a $V_L$-CDR3 sequence of SEQ ID NO: 170, SEQ ID NO: 172, and SEQ ID NO: 171 respectively.

In one aspect, the present disclosure provides an antibody or antigen binding fragment thereof comprising a heavy chain immunoglobulin variable domain ($V_H$) amino acid sequence comprising SEQ ID NO: 1, SEQ ID NO: 10, SEQ ID NO: 20, SEQ ID NO: 30, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123, SEQ ID NO: 133, SEQ ID NO: 143, SEQ ID NO: 153, SEQ ID NO: 163, SEQ ID NO: 173, or SEQ ID NO: 183; and a light chain immunoglobulin variable domain ($V_L$) amino acid sequence comprising SEQ ID NO: 6, SEQ ID NO: 15, SEQ ID NO: 25, SEQ ID NO: 35, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 138, SEQ ID NO: 148, SEQ ID NO: 158, SEQ ID NO: 168, SEQ ID NO: 178, or SEQ ID NO: 188.

In some embodiments, the antibody or antigen binding fragment comprises a $V_H$ amino acid sequence and a $V_L$ amino acid sequence selected from the group consisting of: (a) SEQ ID NO: 163 and SEQ ID NO: 168 (v18596); (b) SEQ ID NO: 153 and SEQ ID NO: 158 (v21826); (c) SEQ ID NO: 113 and SEQ ID NO: 118 (v19363); (d) SEQ ID NO: 183 and SEQ ID NO: 188 (v19362); (e) SEQ ID NO: 133 and SEQ ID NO: 138 (v21828); (f) SEQ ID NO: 30 and SEQ ID NO: 35 (v23790); (g) SEQ ID NO: 20 and SEQ ID NO: 25 (v23791); (h) SEQ ID NO: 10 and SEQ ID NO: 15 (v23792); (i) SEQ ID NO: 1 and SEQ ID NO: 6 (v23793); (j) SEQ ID NO: 173 and SEQ ID NO: 178 (v21825); (k) SEQ ID NO: 143 and SEQ ID NO: 148 (v21827); (l) SEQ ID NO: 123 and SEQ ID NO: 128 (v21829); (m) SEQ ID NO: 63 and SEQ ID NO: 68 (v21831); (n) SEQ ID NO: 53 and SEQ ID NO: 58 (v18343); (o) SEQ ID NO: 73 and SEQ ID NO: 78 (v19373); (p) SEQ ID NO: 83 and SEQ ID NO: 88 (v19372); (q) SEQ ID NO: 93 and SEQ ID NO: 98 (v19371); and (r) SEQ ID NO: 103 and SEQ ID NO: 108 (v19370).

In any of the above embodiments of the antibody or antigen binding fragment described herein, the $V_H$ and $V_L$ are connected via an amino acid linker. In some embodiments, the amino acid linker comprises the sequence $(GGGGS)_3$ (SEQ ID NO: 224), $(GGGGS)_4$ (SEQ ID NO: 225), $SST(GGGGS)_3DI$ (SEQ ID NO: 226), $VE(GGS)_4$ GGVD (SEQ ID NO: 227), GSTSGGGSGGGSGGGSS (SEQ ID NO: 228), and GSTSGSGKPGSGEGSTKG (SEQ ID NO: 229).

Additionally or alternatively, in some embodiments, the antibody or antigen binding fragment of the present technology binds to human CD3 and cynomolgus monkey CD3. In certain embodiments, the antibody or antigen binding fragment of the present technology is a monoclonal antibody, chimeric antibody, humanized antibody, or bispecific antibody. In any of the above embodiments, the antigen binding fragment is selected from the group consisting of Fab, F(ab')$_2$, Fab', scF$_v$, sdAb, and F$_v$.

Additionally or alternatively, in some embodiments, the antibody or antigen binding fragment of the present technology further comprises an Fc domain. The Fc domain may be of any isotype, e.g., but are not limited to, IgG (including IgG1, IgG2, IgG3, and IgG4), IgA (including IgA$_1$ and IgA$_2$), IgD, IgE, or IgM.

Additionally or alternatively, in some embodiments of the antibody or antigen binding fragment of the present technology, the Fc domain is heterodimeric and comprises an IgG constant domain. In certain embodiments, the IgG constant domain is human IgG1 constant domain. The heterodimeric Fc domain may comprise a first CH2 region, a first CH3 region, a second CH2 region and a second CH3 region. Additionally or alternatively, in some embodiments, the first CH3 region comprises one or more amino acid substitutions selected from the group consisting of T350V, L351Y, F405A, and Y407V and/or the second CH3 region comprises one or more amino acid substitutions selected from the group consisting of T350V, T366L, K392L, and T394W. Additionally or alternatively, in some embodiments, the first CH2 region and/or the second CH2 region comprises one or more amino acid substitutions selected from the group consisting of D265S, L234A, and L235A. In any of the above embodiments described herein, the first CH2 region comprises the amino acid sequence of SEQ ID NO: 195 and the first CH3 domain comprises the amino acid sequence of SEQ ID NO: 197 and/or the second CH2 region comprises the amino acid sequence of SEQ ID NO: 201 and the second CH3 domain comprises the amino acid sequence of SEQ ID NO: 203.

In one aspect, the present disclosure provides a recombinant nucleic acid sequence encoding any antibody or antigen binding fragment of the present technology. In some embodiments, the recombinant nucleic acid sequence comprises the sequence of any one of SEQ ID NOs: 54, 59, 64, 69, 74, 79, 84, 89, 94, 99, 104, 109, 114, 119, 124, 129, 134, 139, 144, 149, 154, 159, 164, 169, 174, 179, 184, or 189. Also disclosed herein are host cells or vectors comprising any recombinant nucleic acid sequence of the present technology.

In another aspect, the present disclosure provides a pharmaceutical composition comprising an antibody or antigen binding fragment disclosed herein and a pharmaceutically-acceptable carrier, wherein the antibody or antigen binding fragment is optionally conjugated to an agent selected from the group consisting of isotopes, dyes, chromogens, contrast agents, drugs, toxins, cytokines, enzymes, enzyme inhibitors, hormones, hormone antagonists, growth factors, radionuclides, metals, liposomes, nanoparticles, RNA, DNA, antioxidants, proteins, carbohydrates, lipids, chelating agents, stabilizers, or any combination thereof. In some embodiments of the pharmaceutical composition of the present technology, the antibody or antigen binding fragment is a bispecific antibody disclosed herein.

In one aspect, the present disclosure provides a method for treating a cancer in a subject in need thereof, comprising administering to the subject an effective amount of a bispecific antibody or antigen binding fragment of the present technology. In some embodiments, the bispecific antibody or antigen binding fragment binds to CD3 and a tumor-associated antigen. In certain embodiments, the subject is human. The antibody or antigen binding fragment may be administered intravenously, intramuscularly, intraarterially, intrathecally, intracapsularly, intraorbitally, intradermally, intraperitoneally, transtracheally, subcutaneously, intracerebroventricularly, orally or intranasally. Additionally or alternatively, in some embodiments, the antibody or antigen binding fragment of the present technology recruits T cells for T cell-dependent cellular cytotoxicity (TDCC) against the cancer.

Also disclosed herein are kits comprising at least one immunoglobulin-related composition of the present technology (e.g., any antibody or antigen binding fragment described herein), and instructions for use. In certain embodiments, the immunoglobulin-related composition is coupled to one or more detectable labels. In one embodiment, the one or more detectable labels comprise a radioactive label, a fluorescent label, or a chromogenic label. Additionally or alternatively, the kits further comprise a secondary antibody that specifically binds to the at least one immunoglobulin-related composition of the present technology.

BRIEF DESCRIPTION OF THE DRAWINGS

FIG. 2a shows a ribbon illustration of the crystal structure of rat C3E-1 in complex with human CD3-Epsilon. FIG. 2b shows a model of humanized C3E-1 based on the human V1 framework. The crystal structure of rat C3E-1 was used as template.

FIG. 3a discloses SEQ ID NOS 220-222, 48, 138, 6, 25, 58, 68, 98, 88, and 78, respectively, in order of appearance. FIG. 3b discloses SEQ ID NOS 43, 223, 43, 1, 10, 153 and 133, respectively, in order of appearance.

FIG. 4a is the UPLC-SEC of variant 19363. FIG. 4b is the UPLC-SEC of variant 21825.

FIGS. 5a-5e depict the differential scanning calorimetry (DSC) thermograms of select anti-CD3 variants versus the parental variants.

DETAILED DESCRIPTION

Figure 1:
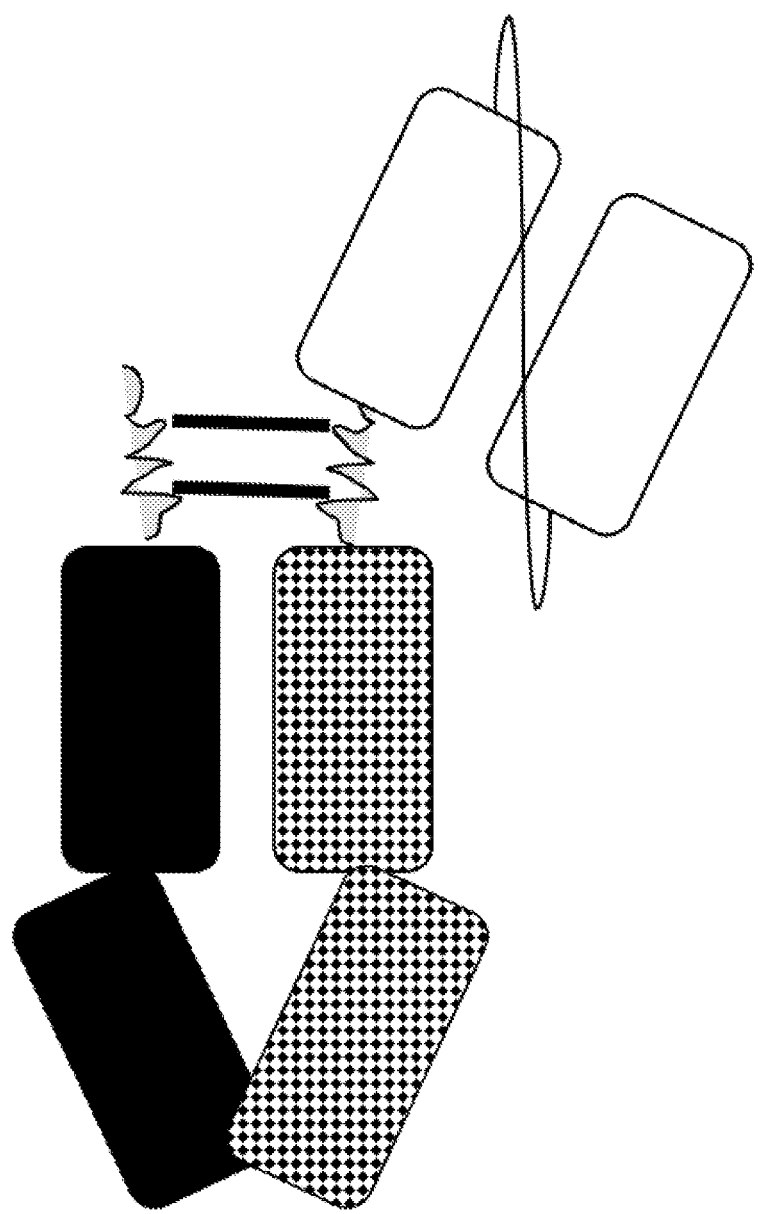
FIG. 1 shows a schematic of an exemplary monovalent anti-CD3 immunoglobulin-related composition used in the Examples described herein. The antigen binding scFv domain is in white, and the non-identical chains of the heterodimeric Fc region are depicted in black and diamond pattern.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, 3rd Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$-CDR3 is located in the variable domain of the heavy chain of the antibody in which it is found, whereas a $V_L$-CDR1 is the CDR1 from the variable domain of the light chain of the antibody in which it is found. An antibody that binds CD3 will have a specific $V_H$ region sequence and $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.) as well as antibody fragments. An antibody or antigen binding fragment thereof specifically binds to an antigen.

As used herein, the term "antibody-related polypeptide" means antigen binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods include, e.g., but are not limited to, Fab, Fab' and F(ab')$_2$, Fd, single-chain Fvs (scFv), single-chain antibodies, single domain antibodies (sdAb), disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', F(ab')$_2$, and Fv fragments; diabodies; linear antibodies; single-chain antibody molecules; and multispecific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scFv)). Bird et al. (1988) *Science* 242:423-426 and Huston et al. (1988) *Proc. Natl. Acad Sci.* USA 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and functional activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be CD3. An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab', sdAb, Fd and F(ab')$_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a breast, lung, pancreas, adrenal gland, brain, kidney, nerve, or muscle tissue sample obtained by needle biopsy. Surgical biopsy samples may be derived from fresh samples or frozen samples obtained at the time of surgery, patient-derived xenografts, or cell lines established for surgical specimens.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., Nature 314: 446-449, 1885; and Shaw et al., *J. Natl. Cancer Inst.* 80: 1553-1559, 1988.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

The term "Fc domain" or "Fc region" herein refers to a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. An "Fc polypeptide" of a dimeric Fc as used herein refers to one of the two polypeptides forming the dimeric Fc domain, i.e., a polypeptide comprising C-terminal constant region of an immunoglobulin heavy chain that is capable of stable self-association. For example, an Fc polypeptide of a dimeric IgG Fc may comprise an IgG CH2 and an IgG CH3 constant domain sequence.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., Nature 321: 522-525 (1986); Reichmann et al., Nature 332:323-329 (1988); and Presta, Curr. Op. Struct. Biol. 2:593-596 (1992). See e.g., Ahmed & Cheung, FEBS Letters 588(2):288-297 (2014).

As used herein, the term "hypervariable region" refers to the amino acid residues of an antibody which are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., Sequences of Proteins of Immunological Interest, 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region as measured using a BLAST or BLAST 2.0 sequence comparison algorithms with default parameters described below, or by manual alignment and visual inspection, (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816, 567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.). The term "pharmaceutically-acceptable carrier" includes diluents, adjuvants, excipients, or vehicles with which a therapeutic agent is administered. Pharmaceutically-acceptable carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a carbohydrate antigen or an epitope on a carbohydrate antigen), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds"

may also refer to binding where a molecule (e.g., an antibody or antigen binding fragment thereof) binds to a particular antigen (e.g., CD3), without substantially binding to any other antigen or form of antigen.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-CD3 antibodies described herein are contemplated. For example, it may be desirable to improve the binding affinity and/or other biological properties of the antibody. Amino acid sequence variants of an anti-CD3 antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in Table A below.

TABLE A

Amino Acid Substitutions

| Original Residue | Exemplary Substitutions | Conservative Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

CD3

The immunoglobulin-related compositions described herein specifically bind a CD3 antigen. "CD3" or "CD3 complex" as described herein is a complex of at least five membrane-bound polypeptides in mature T-lymphocytes that are non-covalently associated with one another and with the T-cell receptor. The CD3 complex includes the gamma, delta, epsilon, and zeta chains (also referred to as subunits). Non-human monoclonal antibodies have been developed against some of these chains, as exemplified by the murine antibodies OKT3, SP34, UCHT1 or 64.1. (See e.g., June et al., *J. Immunol.* 136:3945-3952 (1986); Yang et al., *J. Immunol.* 137:1097-1100 (1986); and Hayward et al., *Immunol.* 64:87-92 (1988)). Clustering of CD3 on T cells, e.g., by immobilized anti-CD3-antibodies, leads to T cell activation similar to the engagement of the T cell receptor but independent from its clone typical specificity. Most anti-CD3-antibodies recognize the CD3ε-chain (UniProt ID: P07766).

Immunoglobulin-Related Compositions of the Present Technology

Provided herein are immunoglobulin-related compositions that bind to a CD3 complex on at least one CD3 expressing cell, wherein the CD3 expressing cell is a T-cell. In certain embodiments, the CD3 expressing cell is a human cell. In some embodiments, the CD3 expressing cell is a non-human, mammalian cell. In some embodiments, the T cell is a cytotoxic T cell or a helper T cell. In some embodiments, the T cell is a CD4 or a CD8 T cell. Additionally or alternatively, in some embodiments, the immunoglobulin-related composition is capable of activating and redirecting cytotoxic activity of a T cell to a target cell. In a particular embodiment, said redirection is independent of MHC-mediated peptide antigen presentation by the target cell and and/or specificity of the T cell.

The present technology describes methods and compositions for the generation and use of anti-CD3 immunoglobulin-related compositions (e.g., anti-CD3 antibodies or antigen binding fragments thereof). Anti-CD3 immunoglobulin-related compositions within the scope of the present technology include, e.g., but are not limited to, monoclonal, chimeric, humanized, and diabodies that specifically bind CD3, a homolog, derivative or a fragment thereof. Anti-CD3 immunoglobulin-related compositions within the scope of the present technology also include compositions in a bispecific antibody format for enhanced anti-tumor potency (e.g., via T cell recruitment or payload delivery). The present disclosure also provides antigen binding fragments of any of the anti-CD3 antibodies disclosed herein, wherein the antigen binding fragment is selected from the group consisting of Fab, F(ab)'$_2$, Fab', scF$_v$, sdAb, and F$_v$. The amino acid sequences of the CDR regions of the immunoglobulin-related compositions disclosed herein are defined according to the Kabat system.

In one aspect, the present technology provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of GVTFNYYG (SEQ ID NO: 3), a $V_H$-CDR2 sequence selected from the group consisting of ITRSGGRI (SEQ ID NO: 5) and ITSSGGRI (SEQ ID NO: 14), and a $V_H$-CDR3 sequence of TLDGRDGWVAY (SEQ ID NO: 4) or TLDGREGWVAY (SEQ ID NO: 156); and/or (b) the $V_L$ comprises a $V_L$-CDR1 sequence of: TGNIGSNY (SEQ ID NO: 7), a $V_L$-CDR2 sequence of RND (SEQ ID NO: 9), and a $V_L$-CDR3 sequence of: QSYSSGFI (SEQ ID NO: 8).

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence, a $V_H$-CDR2 sequence, and a $V_H$-CDR3 sequence of SEQ ID NO: 155, SEQ ID NO: 157, and SEQ ID NO: 156 respectively, and the $V_L$ comprises a $V_L$-CDR1 sequence, a $V_L$-CDR2 sequence, and a $V_L$-CDR3 sequence of SEQ ID NO: 160, SEQ ID NO: 162, and SEQ ID NO: 161 respectively; (b) the $V_H$ comprises a $V_H$-CDR1 sequence, a $V_H$-CDR2 sequence, and a $V_H$-CDR3 sequence of SEQ ID NO: 115, SEQ ID NO: 117, and SEQ ID NO: 116 respectively, and the $V_L$ comprises a $V_L$-CDR1 sequence, a $V_L$-CDR2 sequence, and a $V_L$-CDR3 sequence of SEQ ID NO: 120, SEQ ID NO: 122, and SEQ ID NO: 121 respectively; (c) the $V_H$ comprises a $V_H$-CDR1 sequence, a $V_H$-CDR2 sequence, and a $V_H$-CDR3 sequence of SEQ ID NO: 185, SEQ ID NO: 187, and SEQ ID NO: 186 respectively, and the $V_L$ comprises a $V_L$-CDR1 sequence, a $V_L$-CDR2 sequence, and a $V_L$-CDR3 sequence of SEQ ID NO: 190, SEQ ID NO: 192, and SEQ ID NO: 191 respectively; (d) the $V_H$ comprises a $V_H$-CDR1 sequence, a $V_H$-CDR2 sequence, and a $V_H$-CDR3 sequence of SEQ ID NO: 135, SEQ ID NO: 137, and SEQ ID NO: 136 respectively, and the $V_L$ comprises a $V_L$-CDR1 sequence, a $V_L$-CDR2 sequence, and a $V_L$-CDR3 sequence of SEQ ID NO: 140, SEQ ID NO: 142, and SEQ ID NO: 141 respectively; (e) the $V_H$ comprises a $V_H$-CDR1 sequence, a $V_H$-CDR2 sequence, and a $V_H$-CDR3 sequence of SEQ ID NO: 175, SEQ ID NO: 177, and SEQ ID NO: 176 respectively, and the $V_L$ comprises a $V_L$-CDR1 sequence, a $V_L$-CDR2 sequence, and a $V_L$-CDR3 sequence of SEQ ID NO: 180, SEQ ID NO: 182, and SEQ ID NO: 181 respectively; (f) the $V_H$ comprises a $V_H$-CDR1 sequence, a $V_H$-CDR2 sequence, and a $V_H$-CDR3 sequence of SEQ ID NO: 145, SEQ ID NO: 147, and SEQ ID NO: 146 respectively, and the $V_L$ comprises a $V_L$-CDR1 sequence, a $V_L$-CDR2 sequence, and a $V_L$-CDR3 sequence of SEQ ID NO: 150, SEQ ID NO: 152, and SEQ ID NO: 151 respectively; (g) the $V_H$ comprises a $V_H$-CDR1 sequence, a $V_H$-CDR2 sequence, and a $V_H$-CDR3 sequence of SEQ ID NO: 125, SEQ ID NO: 127, and SEQ ID NO: 126 respectively, and the $V_L$ comprises a $V_L$-CDR1 sequence, a $V_L$-CDR2 sequence, and a $V_L$-CDR3 sequence of SEQ ID NO: 130, SEQ ID NO: 132, and SEQ ID NO: 131 respectively; (h) the $V_H$ comprises a $V_H$-CDR1 sequence, a $V_H$-CDR2 sequence, and a $V_H$-CDR3 sequence of SEQ ID NO: 65, SEQ ID NO: 67, and SEQ ID NO: 66 respectively, and the $V_L$ comprises a $V_L$-CDR1 sequence, a $V_L$-CDR2 sequence, and a $V_L$-CDR3 sequence of SEQ ID NO: 70, SEQ ID NO: 72, and SEQ ID NO: 71 respectively; or (i) the $V_H$ comprises a $V_H$-CDR1 sequence, a $V_H$-CDR2 sequence, and a $V_H$-CDR3 sequence of SEQ ID NO: 165, SEQ ID NO: 167, and SEQ ID NO: 166 respectively, and the $V_L$ comprises a $V_L$-CDR1 sequence, a $V_L$-CDR2 sequence, and a $V_L$-CDR3 sequence of SEQ ID NO: 170, SEQ ID NO: 172, and SEQ ID NO: 171 respectively.

In one aspect, the present disclosure provides an antibody or antigen binding fragment thereof comprising a heavy chain immunoglobulin variable domain ($V_H$) amino acid sequence comprising SEQ ID NO: 1, SEQ ID NO: 10, SEQ ID NO: 20, SEQ ID NO: 30, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123, SEQ ID NO: 133, SEQ ID NO: 143, SEQ ID NO: 153, SEQ ID NO: 163, SEQ ID NO: 173, or SEQ ID NO: 183; and a light chain immunoglobulin variable domain ($V_L$) amino acid sequence comprising SEQ ID NO: 6, SEQ ID NO: 15, SEQ ID NO: 25, SEQ ID NO: 35, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 138, SEQ ID NO: 148, SEQ ID NO: 158, SEQ ID NO: 168, SEQ ID NO: 178, or SEQ ID NO: 188.

In some embodiments, the antibody or antigen binding fragment comprises a $V_H$ amino acid sequence and a $V_L$ amino acid sequence selected from the group consisting of: (a) SEQ ID NO: 163 and SEQ ID NO: 168 (v18596); (b) SEQ ID NO: 153 and SEQ ID NO: 158 (v21826); (c) SEQ ID NO: 113 and SEQ ID NO: 118 (v19363); (d) SEQ ID NO: 183 and SEQ ID NO: 188 (v19362); (e) SEQ ID NO: 133 and SEQ ID NO: 138 (v21828); (f) SEQ ID NO: 30 and SEQ ID NO: 35 (v23790); (g) SEQ ID NO: 20 and SEQ ID NO: 25 (v23791); (h) SEQ ID NO: 10 and SEQ ID NO: 15 (v23792); (i) SEQ ID NO: 1 and SEQ ID NO: 6 (v23793); (j) SEQ ID NO: 173 and SEQ ID NO: 178 (v21825); (k) SEQ ID NO: 143 and SEQ ID NO: 148 (v21827); (l) SEQ ID NO: 123 and SEQ ID NO: 128 (v21829); (m) SEQ ID NO: 63 and SEQ ID NO: 68 (v21831); (n) SEQ ID NO: 53 and SEQ ID NO: 58 (v18343); (o) SEQ ID NO: 73 and SEQ ID NO: 78 (v19373); (p) SEQ ID NO: 83 and SEQ ID NO: 88 (v19372); (q) SEQ ID NO: 93 and SEQ ID NO: 98 (v19371); and (r) SEQ ID NO: 103 and SEQ ID NO: 108 (v19370).

In any of the above embodiments described herein, the $V_H$ and $V_L$ are connected via an amino acid linker. In some embodiments, the amino acid linker comprises the sequence (GGGGS)$_3$ (SEQ ID NO: 224), (GGGGS)$_4$ (SEQ ID NO: 225), SST(GGGGS)$_3$DI (SEQ ID NO: 226), VE(GGS)$_4$GGVD (SEQ ID NO: 227), GSTSGGGSGGGSGGGGSS (SEQ ID NO: 228), and GSTSGSGKPGSGEGSTKG (SEQ ID NO: 229).

Additionally or alternatively, in some embodiments, the immunoglobulin-related compositions of the present technology binds to human CD3 and cynomolgus monkey CD3. In some embodiments, the immunoglobulin-related compositions of the present technology bind human and/or cynomolgus monkey CD3 with a dissociation constant ($K_D$) of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In some embodiments, the immunoglobulin-related composition of the present technology further comprises an Fc domain of any isotype, e.g., but are not limited to, IgG (including IgG1, IgG2, IgG3, and IgG4), IgA (including IgA$_1$ and IgA$_2$), IgD, IgE, or IgM, and IgY.

In some embodiments, the $V_H$ and $V_L$ domain sequences are components of the same polypeptide chain. In other embodiments, the $V_H$ and $V_L$ domain sequences are components of different polypeptide chains. In certain embodiments, the antibody is a full-length antibody.

In certain embodiments, the immunoglobulin-related composition includes one or more of the following characteristics: (a) the light chain immunoglobulin variable domain sequence is at least 80%, at least 85%, at least 90%, at least 95%, or at least 99% identical to the light chain immunoglobulin variable domain sequence present in any one of SEQ ID NOs: 6, 15, 25, 35, 58, 68, 78, 88, 98, 108, 118, 128, 138, 148, 158, 168, 178, or 188; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 1, 10, 20, 30, 53, 63, 73, 83, 93, 103, 113, 123, 133, 143, 153, 163, 173, or SEQ ID NO: 183. In another aspect, one or more amino acid residues in the immunoglobulin-related compositions provided herein are substituted with another amino acid. The substitution may be a "conservative substitution" as defined herein.

scFv. In some embodiments, the immunoglobulin-related composition is in an scFv format (antigen binding domains composed of a heavy chain variable domain and a light chain variable domain that are connected via a polypeptide linker). In certain embodiments, the scFv are human. In another embodiment the scFv molecules are humanized. The scFvs may be optimized for protein expression and yield using one or more of the modifications described below.

The scFv can be optimized by changing the order of the variable domains $V_L$ and $V_H$ in the scFv. In some embodiments of an scFv described herein, the C-terminus of the light chain variable region may be connected to the N-terminus of the heavy chain variable region, or the C-terminus of the heavy chain variable region may be connected to the N-terminus of the light chain variable region.

The variable regions may be connected via a linker peptide, or scFv linker, that allows the formation of a functional antigen-binding moiety. The scFv can be optimized for protein expression and yield by changing the composition and/or length of the scFv linker polypeptide. Typical peptide linkers comprise about 2-20 amino acids, and are described herein or known in the art. Suitable, non-immunogenic linker peptides include, for example, (G$_4$S)$_n$ (SEQ ID NO: 230), (SG$_4$)$_n$ (SEQ ID NO: 231), G$_4$(SG$_4$)$_n$ (SEQ ID NO: 232) or G$_2$(SG$_2$)$_n$ (SEQ ID NO: 233) linker peptides, wherein n is generally a number between 1 and 10, typically between 2 and 4.

The scFv molecule may be optimized for protein expression and yield by including stabilizing disulfide bridges between the heavy and light chain variable domains, for example as described in Reiter et al. *Nat Biotechnol* 14, 1239-1245 (1996). Hence, in one embodiment, the immunoglobulin-related composition of the present technology comprises a scFv molecule wherein an amino acid in the heavy chain variable domain and an amino acid in the light chain variable domain have been replaced by cysteine so that a disulfide bridge can be formed between the heavy and light chain variable domain. In one embodiment, the amino acid at position 44 of the light chain variable domain and the amino acid at position 100 of the heavy chain variable domain are replaced by cysteine (Kabat numbering).

scFvs can also be stabilized by mutation of CDR sequences, as described in Miller et al., *Protein Eng Des Sel.* 23(7):549-57 (2010); Igawa et al., *MAbs.* 3(3):243-5 (2011); Perchiacca & Tessier, *Annu Rev Chem Biomol Eng.* 3:263-86 (2012).

Fc domains of the Immunoglobulin-Related Compositions of the Present Technology. The immunoglobulin-related compositions described herein may comprise an Fc domain, e.g., a dimeric Fc. In some embodiments of the immunoglobulin-related compositions of the present technology, the Fc domain is a heterodimeric Fc comprising a first Fc polypeptide and a second Fc polypeptide. In some embodiments, each Fc polypeptide of the heterodimeric Fc comprises a modified CH3 sequence, wherein each modified CH3 sequence comprises asymmetric amino acid modifications that promote the formation of a heterodimeric Fc and the dimerized CH3 domains have a melting temperature (Tm) of about 68° C. or higher, and wherein the first Fc polypeptide is linked to an antigen binding fragment, optionally via a first hinge linker. In a further embodiment, the second Fc polypeptide is linked to a second antigen-binding fragment, optionally via a second hinge linker. Each Fc polypeptide of a dimeric Fc comprises either a CH3 domain or a CH3 and a CH2 domain.

In some embodiments, the Fc domain comprises at least one or two CH3 domains (monomeric or dimeric) and optionally at least one or two CH2 domains. In some aspects, the Fc is a heterodimeric Fc. In some embodiments, the Fc domain is coupled, with or without one or more linkers, to a first antigen-binding fragment and/or a second antigen-binding fragment.

Additionally or alternatively, in some embodiments, the Fc domain comprises an IgG constant domain (e.g., IgG1 constant domain). Additionally or alternatively, in some embodiments, the IgG constant domain is human (e.g., human IgG1 constant domain).

In any of the embodiments described herein, the Fc comprises one or more modifications in at least one of the CH3 sequences. Additionally or alternatively, in some embodiments, the Fc comprises one or more modifications in at least one of the CH2 sequences. In some embodiments, the Fc is an Fc described in WO12058768 or WO13063702, the entire disclosures of which are hereby incorporated by reference in its entirety for all purposes.

The heterodimeric Fc domain may comprise a first CH2 region, a first CH3 region, a second CH2 region and a second CH3 region. Additionally or alternatively, in some embodiments, the first CH3 region comprises one or more amino acid substitutions selected from the group consisting of T350V, L351Y, F405A, and Y407V and/or the second CH3 region comprises one or more amino acid substitutions selected from the group consisting of T350V, T366L, K392L, and T394W. Additionally or alternatively, in some embodiments, the first CH2 region and/or the second CH2 region comprises one or more amino acid substitutions selected from the group consisting of D265S, L234A, and L235A. In any of the above embodiments described herein, the first CH2 region comprises the amino acid sequence of SEQ ID NO: 195 and the first CH3 domain comprises the amino acid sequence of SEQ ID NO: 197 and/or the second CH2 region comprises the amino acid sequence of SEQ ID NO: 201 and the second CH3 domain comprises the amino acid sequence of SEQ ID NO: 203.

Modified CH3 Domains. In some embodiments, the immunoglobulin-related composition described herein comprises a heterodimeric Fc comprising a modified CH3 domain that has been asymmetrically modified. The heterodimeric Fc can comprise two heavy chain constant domain polypeptides: a first Fc polypeptide and a second Fc polypeptide, which can be used interchangeably provided that the heterodimeric Fc comprises one first Fc polypeptide and one second Fc polypeptide. Generally, the first Fc polypeptide comprises a first CH3 sequence and the second Fc polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Typically a dimeric Fc can include two contiguous heavy chain sequences (A and B) that are capable of dimerizing. With respect to the immunoglobulin-related compositions described herein, in some embodiments, the first antigen binding fragment is linked to chain A of the heterodimeric Fc and the second antigen binding fragment is linked to chain B of the heterodimeric Fc. In some embodiments, the second antigen binding fragment is linked to chain A of the heterodimeric Fc and the first antigen binding fragment is linked to chain B of the heterodimeric Fc.

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from among L351Y, F405A, and Y407V, and the second CH3 sequence having one or more amino acid modifications selected from among T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351. F405 and Y407, and a second CH3 sequence having amino acid modifications at position T366. K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351. F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In some embodiments, a heterodimeric Fc comprises a modified CH3 domain comprising the following amino acid modifications, where "A" represents the amino acid modifications to the first CH3 sequence, and "B" represents the amino acid modifications to the second CH3 sequence: A: L351Y_F405A_Y407V, B: T366L_K392M_T394W, A: L351Y_F405A_Y407V, B: T366L_K392L_T394W, A: T350V_L351Y_F405A_Y407V, B: T350V_T366L_K392L_T394W, A: T350V_L351Y_F405A_Y407V, B: T350V_T366L_K392M_T394W, A: T350V_L351Y_S400E_F405A_Y407V, and/or B: T350V_T366L N390R_K392M_T394W.

In some embodiments, one or both sequences of an Fc domain include one or more mutations or modifications at the following locations of the human IgG1 constant domain: L351, F405, Y407, T366, K392, T394, T350, S400, and/or N390, using EU numbering. In some embodiments, a dimeric Fc includes a mutant sequence shown in Table B. In some embodiments, a dimeric Fc includes the mutations of Variant 1 A-B. In other embodiments, a dimeric Fc includes the mutations of Variant 2 A-B. In certain embodiments, a dimeric Fc includes the mutations of Variant 3 A-B. In some embodiments, a dimeric Fc includes the mutations of Variant 4 A-B. In some embodiments, a dimeric Fc includes the mutations of Variant 5 A-B.

TABLE B

| Exemplar Heterodimeric IgG1 Variants | Chain | Mutations |
|---|---|---|
| 1 | A | L351Y_F405A_Y407V |
|   | B | T366L_K392M_T394W |
| 2 | A | L351Y_F405A_Y407V |
|   | B | T366L_K392L_T394W |
| 3 | A | T350V_L351Y_F405A_Y407V |
|   | B | T350V_T366L_K392L_T394W |
| 4 | A | T350V_L351Y_F405A_Y407V |
|   | B | T350V_T366L_K392M_T394W |
| 5 | A | T350V_L351Y_S400E_F405A_Y407V |
|   | B | T350V_T366L_N390R_K392M_T394W |

The one or more asymmetric amino acid modifications can promote the formation of a heterodimeric Fc in which the heterodimeric CH3 domain has a stability that is comparable to a wild-type homodimeric CH3 domain. In certain embodiments, the one or more asymmetric amino acid modifications promote the formation of a heterodimeric Fc domain in which the heterodimeric Fc domain has a stability that is comparable to a wild-type homodimeric Fc domain. In some embodiments, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some embodiments, the Fc comprises one or more modifications in at least one of the CH3 sequences that promote the formation of a heterodimeric Fc with stability comparable to a wild-type homodimeric Fc.

In certain embodiments, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some embodiments, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some embodiments, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in WO96/027011, Gunasekaran K. et al. (2010) *J Biol Chem.* 285, 19637-46 (electrostatic design to achieve selective heterodimerization), Davis, J H. et al. (2010) *Prot Eng Des Sel* 23(4): 195-202 (strand exchange engineered domain (SEED) technology), and in Labrijn et al., *Proc Natl Acad Sci* (2013) 110(13):5145-50.

CH2 Domains. As described herein, in some embodiments, the Fc of the immunoglobulin-related composition of the present technology comprises a CH2 domain in addition to a CH3 domain. The CH2 domain of the Fc binds to Fc receptors and complement and is thus involved in mediating effector cell functions.

The terms "Fc receptor" and "FcR" are used to describe a receptor that binds to the Fc region of an antibody, and includes Fc gamma receptors (FcγRs) and the neonatal receptor FcRn.

Generally, an FcγR is one which binds an IgG antibody (a gamma receptor) and includes receptors of the FcγRI, FcγRII, and FcγRIII subclasses in humans, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcγRs, including those to be identified in the future, are encompassed by the term "FcR" herein. An FcγR are also found in other organisms, including but not limited to mice, rats, rabbits, and monkeys. Mouse FcγRs include but are not limited to FcγRI (CD64), FcγRII (CD32), FcγRIII (CD 16), and FcγRIII-2 (CD 16-2). FcγRs are expressed by effector cells such as NK cells or B cells.

Complement activation requires binding of the complement protein C1q to antigen-antibody complexes. Residues in the CH2 domain of the Fc are involved in the interaction between C1q and the Fc.

The immunoglobulin-related compositions described herein are able to bind FcRn. As is known in the art, binding to FcRn recycles endocytosed antibody from the endosome back to the bloodstream (Raghavan et al., 1996, *Annu Rev Cell Dev Biol* 12:181-220; Ghetie et al., 2000, *Annu Rev Immunol* 18:739-766). This process, coupled with preclusion of kidney filtration due to the large size of the full-length molecule, results in favorable antibody serum half-lives ranging from one to three weeks. Binding of Fc to FcRn also plays a key role in antibody transport. FcRn is responsible for the transfer of maternal IgGs to the fetus (Guyer et al., *J. Immunol.* 117:587 (1976); and Kim et al., *J. Immunol.* 24:249 (1994)). Binding of the FcRn to IgG involves residues in the CH2 and CH3 domains of the Fc.

Modifications in the CH2 domain can affect the binding of FcRs to the Fc. As described herein, a dimeric Fc may comprise two CH2 sequences, one on each of the two Fc polypeptides of the dimeric Fc. Typically, the modifications to the CH2 domain are symmetric and are thus the same on both CH2 sequences of the Fc polypeptides of the dimeric Fc. However, asymmetric mutations are also possible in the presence of mutations on the CH3 domain that enhance heterodimerization. In one embodiment, the CH2 domain comprises modifications to reduce FcγR or C1q binding and/or effector function.

Modifications to Reduce Effector Function. Fc modifications reducing FcγR and/or complement binding and/or effector function are known in the art. Recent publications describe strategies that have been used to engineer antibodies with reduced or silenced effector activity (see Strohl, W R (2009), *Curr Opin Biotech* 20:685-691, and Strohl, W R and Strohl L M. "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO2006/105338 (Xencor), US Patent Publication No. 2012/0225058 (Xencor), US Patent Publication No. 2012/0251531 (Genentech), and Strop et al., *J. Mol. Biol.* 420: 204-219 (2012) describe specific modifications to reduce FcγR or complement binding to the Fc.

Specific, non-limiting examples of symmetric amino acid modifications include: N297A, L234A/L235A, L234F/L235E/P331S, C226S/P230S, C220S/C226S/C229S/P238S, and C226S/C229S/E3233P/L235V/L235A in human IgG1 constant domain; V234A/G237A and H268Q/V309L/A330S/A331S in human IgG2 constant domain; and L235A/G237A/E318A and S228P/L236E in human IgG4 constant domain. In some embodiments of the immunoglobulin-related compositions of the present technology, the Fc comprises at least one amino acid modification selected from the group consisting of N297A, L234A/L235A, L234F/L235E/P331S, C226S/P230S, C220S/C226S/C229S/P238S, and C226S/C229S/E3233P/L235V/L235A in human IgG1 constant domain; V234A/G237A and H268Q/V309L/A330S/A331S in human IgG2 constant domain; and L235A/G237A/E318A and S228P/L236E in human IgG4 constant domain.

In another embodiment, the Fc comprises an amino acid modification of at least one of L234, L235, or D265. In another embodiment, the Fc comprises an amino acid modification of at least one of L234, L235 and D265. In another embodiment, the Fc comprises an amino acid modification of at least one of L234A, L235A and D265S.

In some embodiments, the Fc comprises one or more asymmetric amino acid modifications in the lower hinge region of the Fc as described in International Patent Application No. PCT/CA2014/050507. Examples of such asymmetric amino acid modifications that reduce FcγR binding are shown in Table C.

TABLE C

| Chain A | Chain B |
| --- | --- |
| L234D/L235E | L234K/L235K |
| E233A/L234D/L235E | E233A/L234R/L235R |

TABLE C-continued

| Chain A | Chain B |
| --- | --- |
| L234D/L235E | E233K/L234R/L235R |
| E233A/L234K/L235A | E233K/L234A/L235K |

Hinge Linkers. In some embodiments of the immunoglobulin-related compositions described herein, the first Fc polypeptide is linked to a first antigen-binding fragment with a first hinge linker, and optionally the second Fc polypeptide is linked to a second antigen-binding fragment with a second hinge linker. Examples of hinge linker sequences are well-known to one of skill in the art and can be used in the immunoglobulin-related compositions described herein. Alternatively, modified versions of known hinge linkers can be used.

The hinge linker polypeptides are selected such that they maintain or optimize the functional activity of the immunoglobulin-related composition. Suitable linker polypeptides include IgG hinge regions such as, for example those from $IgG_1$, $IgG_2$, or $IgG_4$, including the upper hinge sequences and core hinge sequences. The amino acid residues corresponding to the upper and core hinge sequences vary depending on the IgG type, as is known in the art and one of skill in the art would readily be able to identify such sequences for a given IgG type. Modified versions of these exemplary linkers can also be used. For example, modifications to improve the stability of the IgG4 hinge are known in the art (see for example, Labrijn et al. (2009) *Nature Biotechnology* 27, 767-771). Examples of hinge linker sequences are found in the following Table D.

TABLE D

EPKSCDKTHTCPPCP (SEQ ID NO: 238)

GAGCCCAAGAGCTGTGATAAGACCCACACCTGCCCTCCCTGTCCA (SEQ ID NO: 239)

AAEPKSSDKTHTCPPCP (SEQ ID NO: 240)

GCAGCCGAACCCAAATCCTCTGATAAGACCC ACACATGCCCTCCATGTCCA (SEQ ID NO: 241)

EPKSSDKTHTCPPCP (SEQ ID NO: 242)

GAGCCTAAAAGCTCCGACAAGACCCACACAT GCCCACCTTGTCCG (SEQ ID NO: 243)

DKTHTCPPCP (SEQ ID NO: 244)

GACAAGACCCACACATGCCCACCTTGTCCG (SEQ ID NO: 245)

GTCPPCP (SEQ ID NO: 246)

GGCACATGCCCTCCATGTCCA (SEQ ID NO: 247)

Amino acid and nucleotide sequences of exemplary anti-CD3 immunoglobulin-related compositions are shown, for example, in Tables E and F.

scFv Variants

TABLE E

| SEQ ID No. | Variant number | Domain | Sequence Type | Sequence |
| --- | --- | --- | --- | --- |
| 1. | 23793 | $V_H$ | Protein | EVQLVESGGGLVQPGGSLRLSCAASGVTFNY YGMSWIRQAPGKGLEWVASITRSGGRIYYPD SVKGRFTISRENTQKTLYLQMNSLRAEDTAV YYCTLDGRDGWVAYWGQGTLVTVSS |

TABLE E-continued

| SEQ ID No. | Variant number | Domain | Sequence Type | Sequence |
|---|---|---|---|---|
| 2. | 23793 | $V_H$ | DNA | — |
| 3. | 23793 | $V_H$CDR1 | Protein | GVTFNYYG |
| 4. | 23793 | $V_H$CDR3 | Protein | TLDGRDGWVAY |
| 5. | 23793 | $V_H$CDR2 | Protein | ITRSGGRI |
| 6. | 23793 | $V_L$ | Protein | QFVLTQPPSASGTPGQRVTISCKRNTGNIGSNYVNWYQQLPGTAPKTIIYRNDKRPDGVPDRFSGSIDSSSNSASLAISGLQSEDEADYYCQSYSSGFIFGGGTKLTVL |
| 7. | 23793 | $V_L$CDR1 | Protein | TGNIGSNY |
| 8. | 23793 | $V_L$CDR3 | Protein | QSYSSGFI |
| 9. | 23793 | $V_L$CDR2 | Protein | RND |
| 10. | 23792 | $V_H$ | Protein | EVQLVESGGGLVQPGGSLRLSCAASGVTFNYYGMSWIRQAPGKGLEWVASITSSGGRIYYPDSVKGRFTISRENTQKTLYLQMNSLRAEDTAVYYCTLDGRDGWVAYWGQGTLVTVSS |
| 11. | 23792 | $V_H$ | DNA | — |
| 12. | 23792 | $V_H$CDR1 | Protein | GVTFNYYG |
| 13. | 23792 | $V_H$CDR3 | Protein | TLDGRDGWVAY |
| 14. | 23792 | $V_H$CDR2 | Protein | ITSSGGRI |
| 15. | 23792 | $V_L$ | Protein | QFVLTQPPSASGTPGQRVTISCKRNTGNIGSNYVNWYQQLPGTAPKTIIYRNDKRPDGVPDRFSGSIDSSSNSASLAISGLQSEDEADYYCQSYSSGFIFGGGTKLTVL |
| 16. | 23792 | $V_L$ | DNA | — |
| 17. | 23792 | $V_L$CDR1 | Protein | TGNIGSNY |
| 18. | 23792 | $V_L$CDR3 | Protein | QSYSSGFI |
| 19. | 23792 | $V_L$CDR2 | Protein | RND |
| 20. | 23791 | $V_H$ | Protein | EVQLVESGGGLVQPGGSLRLSCAASGVTFNYYGMSWIRQAPGKGLEWVASITRSGGRIYYPDSVKGRFTISRENTQKTLYLQMNSLRAEDTAVYYCTLDGRDGWVAYWGQGTLVTVSS |
| 21. | 23791 | $V_H$ | DNA | — |
| 22. | 23791 | $V_H$CDR1 | Protein | GVTFNYYG |
| 23. | 23791 | $V_H$CDR3 | Protein | TLDGRDGWVAY |
| 24. | 23791 | $V_H$CDR2 | Protein | ITRSGGRI |
| 25. | 23791 | $V_L$ | Protein | NFMLTQPHSVSESPGKTVTISCKRNTGNIGSNYVNWYQQLPGTAPKTIIYRNDKRPDGVPDRFSGSIDSSSNSASLAISGLQSEDEADYYCQSYSSGFIFGGGTKLTVL |
| 26. | 23791 | $V_L$ | DNA | — |
| 27. | 23791 | $V_L$CDR1 | Protein | TGNIGSNY |
| 28. | 23791 | $V_L$CDR3 | Protein | QSYSSGFI |
| 29. | 23791 | $V_L$CDR2 | Protein | RND |
| 30. | 23790 | $V_H$ | Protein | EVQLVESGGGLVQPGGSLRLSCAASGVTFNYYGMSWIRQAPGKGLEWVASITSSGGRIYYPDSVKGRFTISRENTQKTLYLQMNSLRAEDTAVYYCTLDGRDGWVAYWGQGTLVTVSS |

TABLE E-continued

| SEQ ID No. | Variant number | Domain | Sequence Type | Sequence |
|---|---|---|---|---|
| 31. | 23790 | $V_H$ | DNA | — |
| 32. | 23790 | $V_H$CDR1 | Protein | GVTFNYYG |
| 33. | 23790 | $V_H$CDR3 | Protein | TLDGRDGWVAY |
| 34. | 23790 | $V_H$CDR2 | Protein | ITSSGGRI |
| 35. | 23790 | $V_L$ | Protein | NFMLTQPHSVSESPGKTVTISCKRNTGNIGSNYVNWYQQLPGTAPKTIIYRNDKRPDGVPDRFSGSIDSSSNSASLAISGLQSEDEADYYCQSYSSGFIFGGGTKLTVL |
| 36. | 23790 | $V_L$ | DNA | — |
| 37. | 23790 | $V_L$CDR1 | Protein | TGNIGSNY |
| 39. | 23790 | $V_L$CDR3 | Protein | QSYSSGFI |
| 41. | 23790 | $V_L$CDR2 | Protein | RND |
| 43. | 18346 | $V_H$ | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGRDGWVAYWGQGTLVTVSS |
| 44. | 18346 | $V_H$ | DNA | GAGGTGCAGCTGGTGGAGTCCGGCGGCGGCCTGGTGCAGCCAGGAGGCTCTCTGCGGCTGAGCTGCGCAGCCTCCGGCGTGACCTTCAACTACTATGGCATGAGCTGGATCAGACAGGCCCCCGGCAAGGGCCTGGAGTGGGTGGCCTCTATCACCAATAGCGGCGGCAGGATCTACTATCCTGACTCCGTGAAGGGCAGGTTTACAATCAGCCGGGAGAACACCCAGAAGACACTGTACCTGCAGATGAACAGCCTGCGGGCCGAGGATACCGCCGTGTACTATTGCACACTGGACGGCAGAGACGGATGGGTGGCATATTGGGGACAGGGCACCCTGGTGACAGTGAGCTCC |
| 45. | 18346 | $V_H$CDR1 | Protein | GVTFNYYG |
| 46. | 18346 | $V_H$CDR3 | Protein | TLDGRDGWVAY |
| 47. | 18346 | $V_H$CDR2 | Protein | ITNSGGRI |
| 48. | 18346 | $V_L$ | Protein | NFMLTQPHSVSESPGKTVTISCKRNTGNIGSNYVNWYQQHEGSSPTTIIYRDDKRPDGVSDRFSGSIDRSSKSASLTISNLKTEDEADYFCQSYSSGFIFGGGTKLTVL |
| 49. | 18346 | $V_L$ | DNA | AACTTTATGCTGACCCAGCCACACTCCGTGTCTGAGAGCCCCGGCAAGACCGTGACAATCAGCTGTAAGAGAAACACAGGCAATATCGGCTCCAACTACGTGAATTGGTATCAGCAGCACGAGGGCTCTAGCCCTACCACAATCATCTACCGGGACGATAAGCGGCCCGACGGCGTGAGCGATCGGTTCTCCGGCTCTATCGACAGATCCTCTAAGAGCGCCTCCCTGACCATCTCTAATCTGAAGACAGAGGACGAGGCCGATTACTTTTGTCAGAGCTATAGCTCCGGCTTCATCTTTGGAGGAGGAACCAAGCTGACAGTGCTG |
| 50. | 18346 | $V_L$CDR1 | Protein | TGNIGSNY |
| 51. | 18346 | $V_L$CDR3 | Protein | QSYSSGFI |
| 52. | 18346 | $V_L$CDR2 | Protein | RDD |
| 53. | 18343 | $V_H$ | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGRDGWVAYWGQGTLVTVSS |
| 54. | 18343 | $V_H$ | DNA | GAGGTGCAGCTGGTGGAGTCCGGCGGCGGCCTGGTGCAGCCTGGCGGCAGCCTGCGGCTG |

TABLE E-continued

| SEQ ID No. | Variant number | Domain | Sequence Type | Sequence |
|---|---|---|---|---|
| | | | | TCCTGCGCCGCCTCTGGCGTGACATTCAACT<br>ACTATGGCATGTCTTGGATCAGACAGGCCC<br>CAGGCAAGGGCCTGGAGTGGGTGGCCAGCA<br>TCACCAATTCCGGCGGCAGGATCTACTATC<br>CCGACAGCGTGAAGGGCAGGTTTACAATCT<br>CCCGCGAGAACACCCAGAAGACACTGTACC<br>TGCAGATGAATAGCCTGAGGGCCGAGGATA<br>CCGCCGTGTACTATTGCACACTGGACGGCA<br>GAGACGGATGGGTGGCATATTGGGGACAGG<br>GCACCCTGGTGACAGTGAGCTCC |
| 55. | 18343 | V$_H$CDR1 | Protein | GVTFNYYG |
| 56. | 18343 | V$_H$CDR3 | Protein | TLDGRDGWVAY |
| 57. | 18343 | V$_H$CDR2 | Protein | ITNSGGRI |
| 58. | 18343 | V$_L$ | Protein | QSVLTQPPSASGTPGQRVTISCKRNTGNIGSN<br>YVNWYQQLPGTAPKLLIYRDDKRPDGVPDRF<br>SGSKSGTSASLAISGLQSEDEADYYCQSYSSG<br>FIFGGGTKLTVL |
| 59. | 18343 | V$_L$ | DNA | CAGTCCGTGCTGACCCAGCCACCTTCTGCCA<br>GCGGAACCCCTGGCCAGCGGGTGACAATCT<br>CTTGTAAGAGAAACACCGGCAATATCGGCA<br>GCAACTACGTGAATTGGTATCAGCAGCTGC<br>CTGGCACAGCCCCAAAGCTGCTGATCTACC<br>GGGACGATAAGCGGCCCGACGGAGTGCCTG<br>ATAGATTTTCCGGCTCTAAGAGCGGCACCT<br>CCGCCTCTCTGGCCATCTCTGGCCTGCAGAG<br>CGAGGACGAGGCCGATTACTATTGTCAGTC<br>CTATTCTAGCGGCTTCATCTTTGGAGGAGGA<br>ACCAAGCTGACAGTGCTG |
| 60. | 18343 | V$_L$CDR1 | Protein | TGNIGSNY |
| 61. | 18343 | V$_L$CDR3 | Protein | QSYSSGFI |
| 62. | 18343 | V$_L$CDR2 | Protein | RDD |
| 63. | 21831 | V$_H$ | Protein | EVQLVESGGGLVQPGGSLRLSCAASGVTFNY<br>YGMSWIRQAPGKGLEWVASITSSGGRIYYPDS<br>VKGRFTISRENTQKTLYLQMNSLRAEDTAVY<br>YCTLDGRDGWVAYWGQGTLVTVSS |
| 64. | 21831 | V$_H$ | DNA | GAGGTGCAGCTGGTGGAGTCTGGCGGCGGC<br>CTGGTGCAGCCTGGCGGCAGCCTGCGGCTG<br>TCCTGCGCCGCCTCTGGCGTGACATTCAACT<br>ACTATGGCATGAGCTGGATCAGACAGGCCC<br>CAGGCAAGGGACTGGAGTGGGTGGCCTCCA<br>TCACCAGCTCCGGCGGCAGGATCTACTATC<br>CCGACTCTGTGAAGGGCAGGTTTACAATCA<br>GCCGCGAGAACACCCAGAAGACACTGTACC<br>TGCAGATGAATAGCCTGAGGGCCGAGGATA<br>CCGCCGTGTACTATTGCACACTGGACGGCA<br>GAGACGGATGGGTGGCATATTGGGGACAGG<br>GCACCCTGGTGACAGTGTCTTCC |
| 65. | 21831 | V$_H$CDR1 | Protein | GVTFNYYG |
| 66. | 21831 | V$_H$CDR3 | Protein | TLDGRDGWVAY |
| 67. | 21831 | V$_H$CDR2 | Protein | ITSSGGRI |
| 68. | 21831 | V$_L$ | Protein | QVVLTQPPSASGTPGQRVTISCKRNTGNIGSN<br>YVNWYQQLPGTAPKLLIYRDDKRPDGVPDRF<br>SGSKSGTSASLAISGLQSEDEADYYCQSYSSG<br>FIFGGGTKLTVL |
| 69. | 21831 | V$_L$ | DNA | CAGGTGGTGCTGACCCAGCCACCTTCTGCC<br>AGCGGAACCCCTGGCCAGCGGGTGACAATC<br>TCCTGTAAGAGAAACACCGGCAATATCGGC<br>TCTAACTACGTGAATTGGTATCAGCAGCTG<br>CCTGGCACAGCCCCAAAGCTGCTGATCTAC<br>CGGGACGATAAGAGACCCGACGGCGTGCCT<br>GATAGATTTTCCGGCTCTAAGAGCGGCACC |

TABLE E-continued

| SEQ ID No. | Variant number | Domain | Sequence Type | Sequence |
|---|---|---|---|---|
| | | | | TCCGCCTCTCTGGCCATCAGCGGACTGCAGT CCGAGGACGAGGCAGATTACTATTGTCAGT CCTATTCCTCTGGCTTCATCTTTGGAGGAGG AACCAAGCTGACAGTGCTG |
| 70. | 21831 | $V_L$CDR1 | Protein | TGNIGSNY |
| 71. | 21831 | $V_L$CDR3 | Protein | QSYSSGFI |
| 72. | 21831 | $V_L$CDR2 | Protein | RDD |
| 73. | 19373 | $V_H$ | Protein | EVQLVESGGGLVQPGGSLRLSCAASGVTFNY YGMSWIRQAPGKGLEWVASITNSGGRIYYPD SVKGRFTISRENTQKTLYLQMNSLRAEDTAV YYCTLDGRDGWVAYWGQGTLVTVSS |
| 74. | 19373 | $V_H$ | DNA | GAGGTGCAGCTGGTGGAGAGCGGCGGCGG CCTGGTGCAGCCTGGAGGCTCCCTGCGGCT GTCTTGCGCAGCCAGCGGCGTGACATTCAA CTACTATGGCATGAGCTGGATCAGACAGGC CCCAGGCAAGGGACTGGAGTGGGTGGCCTC CATCACCAATTCTGGCGGCAGGATCTACTA TCCCGACTCTGTGAAGGGCAGGTTTACAAT CAGCCGCGAGAACACCCAGAAGACACTGTA CCTGCAGATGAACAGCCTGCGGGCCGAGGA TACCGCCGTGTACTATTGCACACTGGACGG CAGAGACGGATGGGTGGCATATTGGGGACA GGGCACCCTGGTGACAGTGAGCTCC |
| 75. | 19373 | $V_H$CDR1 | Protein | GVTFNYYG |
| 76. | 19373 | $V_H$CDR3 | Protein | TLDGRDGWVAY |
| 77. | 19373 | $V_H$CDR2 | Protein | ITNSGGRI |
| 78. | 19373 | $V_L$ | Protein | QFVLTQPPSASGTPGQRVTISCKRNTGNIGSN YVNWYQQLPGTAPKLLIYRDDKRPDGVPDRF SGSKSGTSASLAISGLQSEDEADYYCQSYSSG FIFGGGTKLTVL |
| 79. | 19373 | $V_L$ | DNA | CAGTTCGTGCTGACCCAGCCACCTAGCGCC TCCGGAACCCCTGGCCAGCGGGTGACAATC TCCTGTAAGAGAAACACCGGCAATATCGGC TCTAACTACGTGAATTGGTATCAGCAGCTG CCTGGCACAGCCCCAAAGCTGCTGATCTAC CGGGACGATAAGAGACCCGACGGCGTGCCT GATAGATTTTCTGGCAGCAAGTCCGGCACC TCTGCCAGCCTGGCCATCAGCGGACTGCAG TCCGAGGACGAGGCAGATTACTATTGTCAG AGCTATTCTAGCGGCTTCATCTTTGGAGGAG GAACCAAGCTGACAGTGCTG |
| 80. | 19373 | $V_L$CDR1 | Protein | TGNIGSNY |
| 81. | 19373 | $V_L$CDR3 | Protein | QSYSSGFI |
| 82. | 19373 | $V_L$CDR2 | Protein | RDD |
| 83. | 19372 | $V_H$ | Protein | EVQLVESGGGLVQPGGSLRLSCAASGVTFNY YGMSWIRQAPGKGLEWVASITNSGGRIYYPD SVKGRFTISRENTQKTLYLQMNSLRAEDTAV YYCTLDGRDGWVAYWGQGTLVTVSS |
| 84. | 19372 | $V_H$ | DNA | GAGGTGCAGCTGGTGGAGAGCGGCGGCGG CCTGGTGCAGCCTGGAGGCTCCCTGCGGCT GTCTTGCGCAGCCAGCGGCGTGACATTCAA CTACTATGGCATGAGCTGGATCAGACAGGC CCCAGGCAAGGGACTGGAGTGGGTGGCCTC CATCACCAATTCTGGCGGCAGGATCTACTA TCCCGACTCTGTGAAGGGCAGGTTTACAAT CAGCCGCGAGAACACCCAGAAGACACTGTA CCTGCAGATGAACAGCCTGCGGGCCGAGGA TACCGCCGTGTACTATTGCACACTGGACGG CAGAGACGGATGGGTGGCATATTGGGGACA GGGCACCCTGGTGACAGTGAGCTCC |

TABLE E-continued

| SEQ ID No. | Variant number | Domain | Sequence Type | Sequence |
|---|---|---|---|---|
| 85. | 19372 | V<sub>H</sub>CDR1 | Protein | GVTFNYYG |
| 86. | 19372 | V<sub>H</sub>CDR3 | Protein | TLDGRDGWVAY |
| 87. | 19372 | V<sub>H</sub>CDR2 | Protein | ITNSGGRI |
| 88. | 19372 | V<sub>L</sub> | Protein | QLVLTQPPSASGTPGQRVTISCKRNTGNIGSNYVNWYQQLPGTAPKLLIYRDDKRPDGVPDRFSGSKSGTSASLAISGLQSEDEADYYCQSYSSGFIFGGGTKLTVL |
| 89. | 19372 | V<sub>L</sub> | DNA | CAGCTGGTGCTGACCCAGCCACCTAGCGCCTCCGGAACCCCTGGCCAGCGGGTGACAATCTCCTGTAAGAGAAACACCGGCAATATCGGCTCTAACTACGTGAATTGGTATCAGCAGCTGCCTGGCACAGCCCCAAAGCTGCTGATCTACCGGGACGATAAGAGACCCGACGGCGTGCCTGATAGATTTTCTGGCAGCAAGTCCGGCACCTCTGCCAGCCTGGCCATCAGCGGACTGCAGTCCGAGGACGAGGCAGATTACTATTGTCAGAGCTATTCTAGCGGCTTCATCTTTGGAGGAGGAACCAAGCTGACAGTGCTG |
| 90. | 19372 | V<sub>L</sub>CDR1 | Protein | TGNIGSNY |
| 91. | 19372 | V<sub>L</sub>CDR3 | Protein | QSYSSGFI |
| 92. | 19372 | V<sub>L</sub>CDR2 | Protein | RDD |
| 93. | 19371 | V<sub>H</sub> | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGRDGWVAYWGQGTLVTVSS |
| 94. | 19371 | V<sub>H</sub> | DNA | GAGGTGCAGCTGGTGGAGAGCGGCGGCGGCCTGGTGCAGCCTGGAGGCTCCCTGCGGCTGTCTTGCGCAGCCAGCGGCGTGACATTCAACTACTATGGCATGAGCTGGATCAGACAGGCCCCAGGCAAGGGACTGGAGTGGGTGGCCTCCATCACCAATTCTGGCGGCAGGATCTACTATCCCGACTCTGTGAAGGGCAGGTTTACAATCAGCCGCGAGAACACCCAGAAGACACTGTACCTGCAGATGAACAGCCTGCGGGCCGAGGATACCGCCGTGTACTATTGCACACTGGACGGCAGAGACGGATGGGTGGCATATTGGGGACAGGGCACCCTGGTGACAGTGAGCTCC |
| 95. | 19371 | V<sub>H</sub>CDR1 | Protein | GVTFNYYG |
| 96. | 19371 | V<sub>H</sub>CDR3 | Protein | TLDGRDGWVAY |
| 97. | 19371 | V<sub>H</sub>CDR2 | Protein | ITNSGGRI |
| 98. | 19371 | V<sub>L</sub> | Protein | QIVLTQPPSASGTPGQRVTISCKRNTGNIGSNYVNWYQQLPGTAPKLLIYRDDKRPDGVPDRFSGSKSGTSASLAISGLQSEDEADYYCQSYSSGFIFGGGTKLTVL |
| 99. | 19371 | V<sub>L</sub> | DNA | CAGATCGTGCTGACCCAGCCACCTAGCGCCTCCGGAACCCCTGGCCAGCGGGTGACAATCTCCTGTAAGAGAAACACCGGCAATATCGGCTCTAACTACGTGAATTGGTATCAGCAGCTGCCTGGCACAGCCCCAAAGCTGCTGATCTACCGGGACGATAAGAGACCCGACGGCGTGCCTGATAGATTTTCTGGCAGCAAGTCCGGCACCTCTGCCAGCCTGGCCATCAGCGGACTGCAGTCCGAGGACGAGGCAGATTACTATTGTCAGAGCTATTCTAGCGGCTTCATCTTTGGAGGAGGAACCAAGCTGACAGTGCTG |
| 100. | 19371 | V<sub>L</sub>CDR1 | Protein | TGNIGSNY |
| 101. | 19371 | V<sub>L</sub>CDR3 | Protein | QSYSSGFI |
| 102. | 19371 | V<sub>L</sub>CDR2 | Protein | RDD |

TABLE E-continued

| SEQ ID No. | Variant number | Domain | Sequence Type | Sequence |
|---|---|---|---|---|
| 103. | 19370 | V$_H$ | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGRDGWVAYWGQGTLVTVSS |
| 104. | 19370 | V$_H$ | DNA | GAGGTGCAGCTGGTGGAGAGCGGCGGCGGCCTGGTGCAGCCTGGAGGCTCCCTGCGGCTGTCTTGCGCAGCCAGCGGCGTGACATTCAACTACTATGGCATGAGCTGGATCAGACAGGCCCCCAGGCAAGGGACTGGAGTGGGTGGCCTCCATCACCAATTCTGGCGGCAGGATCTACTATCCCGACTCTGTGAAGGGCAGGTTTACAATCAGCCGCGAGAACACCCAGAAGACACTGTACCTGCAGATGAACAGCCTGCGGGCCGAGGATACCGCCGTGTACTATTGCACACTGGACGGCAGAGACGGATGGGTGGCATATTGGGGACAGGGCACCCTGGTGACAGTGAGCTCC |
| 105. | 19370 | V$_H$CDR1 | Protein | GVTFNYYG |
| 106. | 19370 | V$_H$CDR3 | Protein | TLDGRDGWVAY |
| 107. | 19370 | V$_H$CDR2 | Protein | ITNSGGRI |
| 108. | 19370 | V$_L$ | Protein | QVVLTQPPSASGTPGQRVTISCKRNTGNIGSNYVNWYQQLPGTAPKLLIYRDDKRPDGVPDRFSGSKSGTSASLAISGLQSEDEADYYCQSYSSGFIFGGGTKLTVL |
| 109. | 19370 | V$_L$ | DNA | CAGGTGGTGCTGACCCAGCCACCTAGCGCCTCCGGAACCCCTGGCCAGCGGGTGACAATCTCCTGTAAGAGAAACACCGGCAATATCGGCTCTAACTACGTGAATTGGTATCAGCAGCTGCCTGGCACAGCCCCAAAGCTGCTGATCTACCGGGACGATAAGAGACCCGACGGCGTGCCTGATAGATTTTCTGGCAGCAAGTCCGGCACCTCTGCCAGCCTGGCCATCAGCGGACTGCAGTCCGAGGACGAGGCAGATTACTATTGTCAGAGCTATTCTAGCGGCTTCATCTTTGGAGGAGGAACCAAGCTGACAGTGCTG |
| 110. | 19370 | V$_L$CDR1 | Protein | TGNIGSNY |
| 111. | 19370 | V$_L$CDR3 | Protein | QSYSSGFI |
| 112. | 19370 | V$_L$CDR2 | Protein | RDD |
| 113. | 19363 | V$_H$ | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGRDGWVAYWGQGTLVTVSS |
| 114. | 19363 | V$_H$ | DNA | GAGGTGCAGCTGGTGGAGTCTGGCGGCGGCCTGGTGCAGCCTGGCGGCAGCCTGCGGCTGTCCTGCGCCGCCTCTGGCGTGACCTTCAACTACTATGGCATGAGCTGGATCAGACAGGCCCCAGGCAAGGGACTGGAGTGGGTGGCCAGCATCACCAATTCCGGCGGCAGGATCTACTATCCCGATTCCGTGAAGGGCAGGTTTACAATCAGCCGGGAGAACACCCAGAAGACACTGTACCTGCAGATGAACAGCCTGCGGGCAGAGGACACCGCCGTGTACTATTGCACACTGGACGGCAGAGACGGATGGGTGGCATATTGGGGACAGGGCACCCTGGTGACAGTGAGCTCC |
| 115. | 19363 | V$_H$CDR1 | Protein | GVTFNYYG |
| 116. | 19363 | V$_H$CDR3 | Protein | TLDGRDGWVAY |
| 117. | 19363 | V$_H$CDR2 | Protein | ITNSGGRI |
| 118. | 19363 | V$_L$ | Protein | QFVLTQPPSASGTPGQRVTISCKRNTGNIGSNYVNWYQQLPGTAPKTIIYRDNKRPDGVPDRFSGSIDSSSNSASLAISGLQSEDEADYYCQSYSSGFIFGGGTKLTVL |

TABLE E-continued

| SEQ ID No. | Variant number | Domain | Sequence Type | Sequence |
|---|---|---|---|---|
| 119. | 19363 | $V_L$ | DNA | CAGTTCGTGCTGACCCAGCCACCTAGCGCC<br>TCCGGAACCCCTGGCCAGCGGGTGACAATC<br>AGCTGTAAGAGAAACACAGGCAATATCGGC<br>TCCAACTACGTGAATTGGTATCAGCAGCTG<br>CCTGGCACCGCCCCAAAGACAATCATCTAC<br>CGGAACGACAAGAGACCCGATGGCGTGCCT<br>GACAGATTTTCTGGCAGCATCGATTCTAGCT<br>CCAATTCCGCCTCTCTGGCCATCTCTGGCCT<br>GCAGAGCGAGGACGAGGCCGATTACTATTG<br>TCAGAGCTATTCTAGCGGCTTCATCTTTGGA<br>GGAGGAACCAAGCTGACAGTGCTG |
| 120. | 19363 | $V_L$CDR1 | Protein | TGNIGSNY |
| 121. | 19363 | $V_L$CDR3 | Protein | QSYSSGFI |
| 122. | 19363 | $V_L$CDR2 | Protein | RND |
| 123. | 21829 | $V_H$ | Protein | EVQLVESGGGLVQPGGSLRLSCAASGVTFNY<br>YGMSWIRQAPGKGLEWVASITRSGGRIYYPD<br>SVKGRFTISRENTQKTLYLQMNSLRAEDTAV<br>YYCTLDGRDGWVAYWGQGTLVTVSS |
| 124. | 21829 | $V_H$ | DNA | GAGGTGCAGCTGGTGGAGTCCGGAGGAGG<br>ACTGGTGCAGCCTGGAGGCTCCCTGAGGCT<br>GTCTTGCGCAGCCAGCGGAGTGACATTCAA<br>CTACTATGGCATGAGCTGGATCAGACAGGC<br>CCCAGGCAAGGGACTGGAGTGGGTGGCCTC<br>CATCACCCGGTCTGGCGGCAGAATCTACTA<br>TCCCGACTCTGTGAAGGGCCGGTTTACAAT<br>CAGCAGAGAGAACACCCAGAAGACACTGT<br>ACCTGCAGATGAACAGCCTGCGGGCCGAGG<br>ATACCGCCGTGTACTATTGCACACTGGACG<br>GCAGAGATGGATGGGTGGCATATTGGGGAC<br>AGGGCACCCTGGTGACAGTGAGCTCC |
| 125. | 21829 | $V_H$CDR1 | Protein | GVTFNYYG |
| 126. | 21829 | $V_H$CDR3 | Protein | TLDGRDGWVAY |
| 127. | 21829 | $V_H$CDR2 | Protein | ITRSGGRI |
| 128. | 21829 | $V_L$ | Protein | QVVLTQPPSASGTPGQRVTISCKRNTGNIGSN<br>YVNWYQQLPGTAPKLLIYRDDKRPDGVPDRF<br>SGSKSGTSASLAISGLQSEDEADYYCQSYSSG<br>FIFGGGTKLTVL |
| 129. | 21829 | $V_L$ | DNA | CAGGTGGTGCTGACCCAGCCACCTAGCGCC<br>TCCGGAACCCCTGGCCAGAGGGTGACAATC<br>TCCTGTAAGCGCAACACCGGCAATATCGGC<br>TCTAACTACGTGAATTGGTATCAGCAGCTG<br>CCTGGCACAGCCCCAAAGCTGCTGATCTAC<br>AGGGACGATAAGAGACCCGACGGCGTGCCT<br>GATCGGTTTTCTGGCAGCAAGTCCGGCACC<br>TCTGCCAGCCTGGCCATCAGCGGACTGCAG<br>TCCGAGGACGAGGCAGATTACTATTGTCAG<br>AGCTATTCTAGCGGCTTCATCTTTGGAGGAG<br>GAACCAAGCTGACAGTGCTG |
| 130. | 21829 | $V_L$CDR1 | Protein | TGNIGSNY |
| 131. | 21829 | $V_L$CDR3 | Protein | QSYSSGFI |
| 132. | 21829 | $V_L$CDR2 | Protein | RDD |
| 133. | 21828 | $V_H$ | Protein | EVQLVESGGGLVQPGGSLRLSCAASGVTFNY<br>YGMSWIRQAPGKGLEWVASITSSGGRIYYPDS<br>VKGRFTISRENTQKTLYLQMNSLRAEDTAVY<br>YCTLDGREGWVAYWGQGTLVTVSS |
| 134. | 21828 | $V_H$ | DNA | GAGGTGCAGCTGGTGGAGTCCGGCGGCGGC<br>CTGGTGCAGCCAGGAGGCTCCCTGCGGCTG<br>TCTTGCGCAGCCAGCGGCGTGACCTTCAAC<br>TACTATGGCATGTCCTGGATCAGACAGGCC<br>CCCGGCAAGGGACTGGAGTGGGTGGCCTCT<br>ATCACCAGCTCCGGCGGCAGGATCTACTAT |

TABLE E-continued

| SEQ ID No. | Variant number | Domain | Sequence Type | Sequence |
|---|---|---|---|---|
| | | | | CCTGATTCCGTGAAGGGCAGGTTTACAATC AGCCGGGAGAACACCCAGAAGACACTGTAC CTGCAGATGAATAGCCTGAGGGCCGAGGAT ACCGCCGTGTACTATTGCACACTGGACGGC AGAGAGGGATGGGTGGCATATTGGGGACA GGGCACCCTGGTGACAGTGTCTAGC |
| 135. | 21828 | $V_H$CDR1 | Protein | GVTFNYYG |
| 136. | 21828 | $V_H$CDR3 | Protein | TLDGREGWVAY |
| 137. | 21828 | $V_H$CDR2 | Protein | ITSSGGRI |
| 138. | 21828 | $V_L$ | Protein | NFMLTQPHSVSESPGKTVTISCKRNTGNIGSN YVNWYQQHEGSSPTTIIYRNDKRPDGVSDRFS GSIDRSSKSASLTISNLKTEDEADYFCQSYSSG FIFGGGTKLTVL |
| 139. | 21828 | $V_L$ | DNA | AACTTCATGCTGACCCAGCCACACAGCGTG TCCGAGTCTCCCGGCAAGACCGTGACAATC AGCTGTAAGAGAAACACAGGCAATATCGGC TCCAACTACGTGAATTGGTATCAGCAGCAC GAGGGCTCCTCTCCTACCACAATCATCTACC GGAACGACAAGAGACCAGATGGCGTGTCCG ACCGGTTCAGCGGCTCCATCGATAGAAGCT CCAAGTCTGCCAGCCTGACCATCTCTAATCT GAAGACAGAGGACGAGGCCGATTACTTTTG TCAGAGCTATTCTAGCGGCTTCATCTTTGGA GGAGGAACCAAGCTGACAGTGCTG |
| 140. | 21828 | $V_L$CDR1 | Protein | TGNIGSNY |
| 141. | 21828 | $V_L$CDR3 | Protein | QSYSSGFI |
| 142. | 21828 | $V_L$CDR2 | Protein | RND |
| 143. | 21827 | $V_H$ | Protein | EVQLVESGGGLVQPGGSLRLSCAASGVTFNY YGMSWIRQAPGKGLEWVASITSSGGRIYYPDS VKGRFTISRENTQKTLYLQMNSLRAEDTAVY YCTLDGREGWVAYWGQGTLVTVSS |
| 144. | 21827 | $V_H$ | DNA | GAGGTGCAGCTGGTGGAGTCTGGCGGCGGC CTGGTGCAGCCTGGCGGCAGCCTGCGGCTG TCCTGCGCCGCCTCTGGCGTGACATTCAACT ACTATGGCATGAGCTGGATCAGACAGGCCC CAGGCAAGGGACTGGAGTGGGTGGCCTCCA TCACCAGCTCCGGCGGCAGGATCTACTATC CCGACTCTGTGAAGGGCAGGTTTACAATCA GCCGCGAGAACACCCAGAAGACACTGTACC TGCAGATGAATAGCCTGAGGGCCGAGGACA CCGCCGTGTACTATTGCACACTGGATGGCC GCGAGGGATGGGTGGCATATTGGGGACAGG GCACCCTGGTGACAGTGTCTTCC |
| 145. | 21827 | $V_H$CDR1 | Protein | GVTFNYYG |
| 146. | 21827 | $V_H$CDR3 | Protein | TLDGREGWVAY |
| 147. | 21827 | $V_H$CDR2 | Protein | ITSSGGRI |
| 148. | 21827 | $V_L$ | Protein | QVVLTQPPSASGTPGQRVTISCKRNTGNIGSN YVNWYQQLPGTAPKLLIYRDDKRPDGVPDRF SGSKSGTSASLAISGLQSEDEADYYCQSYSSG FIFGGGTKLTVL |
| 149. | 21827 | $V_L$ | DNA | CAGGTGGTGCTGACCCAGCCACCTTCTGCC AGCGGAACCCCTGGCCAGCGGGTGACAATC TCCTGTAAGAGAAACACCGGCAATATCGGC TCTAACTACGTGAATTGGTATCAGCAGCTG CCTGGCACAGCCCCAAAGCTGCTGATCTAC CGGGACGATAAGAGACCCGACGGCGTGCCT GATAGATTTTCCGGCTCTAAGAGCGGCACC TCCGCCTCTCTGGCCATCAGCGGACTGCAGT CCGAGGACGAGGCAGATTACTATTGTCAGT CCTATTCCTCTGGCTTCATCTTTGGAGGAGG AACCAAGCTGACAGTGCTG |

TABLE E-continued

| SEQ ID No. | Variant number | Domain | Sequence Type | Sequence |
|---|---|---|---|---|
| 150. | 21827 | V_LCDR1 | Protein | TGNIGSNY |
| 151. | 21827 | V_LCDR3 | Protein | QSYSSGFI |
| 152. | 21827 | V_LCDR2 | Protein | RDD |
| 153. | 21826 | V_H | Protein | EVQLVESGGGLVQPGGSLRLSCAASGVTFNYYGMSWIRQAPGKGLEWVASITRSGGRIYYPDSVKGRFTISRENTQKTLYLQMNSLRAEDTAVYYCTLDGREGWVAYWGQGTLVTVSS |
| 154. | 21826 | V_H | DNA | GAGGTGCAGCTGGTGGAGTCCGGAGGAGGACTGGTGCAGCCAGGAGGCTCTCTGAGGCTGAGCTGCGCAGCCTCCGGCGTGACCTTCAACTACTATGGCATGAGCTGGATCAGACAGGCCCCCGGCAAGGGACTGGAGTGGGTGGCCTCTATCACCCGGAGCGGCGGCAGAATCTACTATCCTGATTCCGTGAAGGGCCGGTTTACAATCTCTAGAGAGAACACCCAGAAGACACTGTACCTGCAGATGAACAGCCTGCGGGCCGAGGATACCGCCGTGTACTATTGCACACTGGACGGCAGAGAGGGATGGGTGGCATATTGGGACAGGGCACCCTGGTGACAGTGAGCTCC |
| 155. | 21826 | V_HCDR1 | Protein | GVTFNYYG |
| 156. | 21826 | V_HCDR3 | Protein | TLDGREGWVAY |
| 157. | 21826 | V_HCDR2 | Protein | ITRSGGRI |
| 158. | 21826 | V_L | Protein | NFMLTQPHSVSESPGKTVTISCKRNTGNIGSNYVNWYQQHEGSSPTTIIYRNDKRPDGVSDRFSGSIDRSSKSASLTISNLKTEDEADYFCQSYSSGFIFGGGTKLTVL |
| 159. | 21826 | V_L | DNA | AACTTCATGCTGACCCAGCCACACTCCGTGTCTGAGAGCCCCGGCAAGACCGTGACAATCAGCTGTAAGCGGAACACAGGCAATATCGGCTCCAACTACGTGAATTGGTATCAGCAGCACGAGGGCTCTAGCCCTACCACAATCATCTACAGGAACGACAAGCGCCCAGATGGCGTGAGCGACAGGTTCTCCGGCTCTATCGATCGCTCCTCTAAGAGCGCCTCCCTGACCATCTCTAATCTGAAGACAGAGGACGAGGCCGATTACTTTTGTCAGAGCTATAGCTCCGGCTTCATCTTTGGAGGAGGAACCAAGCTGACAGTGCTG |
| 160. | 21826 | V_LCDR1 | Protein | TGNIGSNY |
| 161. | 21826 | V_LCDR3 | Protein | QSYSSGFI |
| 162. | 21826 | V_LCDR2 | Protein | RND |
| 163. | 18596 | V_H | Protein | EVQLVESGGGLVQPGGSLRLSCAASGVTFNYYGMSWIRQAPGKGLEWVASITNSGGRIYYPDSVKGRFTISRENTQKTLYLQMNSLRAEDTAVYYCTLDGREGWVAYWGQGTLVTVSS |
| 164. | 18596 | V_H | DNA | GAGGTGCAGCTGGTGGAGTCCGGCGGCGGCCTGGTGCAGCCAGGAGGCTCTCTGCGGCTGAGCTGCGCAGCCTCCGGCGTGACCTTCAACTACTATGGCATGAGCTGGATCAGACAGGCCCCCGGCAAGGGCCTGGAGTGGGTGGCCTCTATCACCAATAGCGGCGGCAGGATCTACTATCCTGACTCCGTGAAGGGCAGGTTTACAATCAGCCGGGAGAACACCCAGAAGACACTGTACCTGCAGATGAACAGCCTGCGGGCAGAGGACACCGCCGTGTACTATTGCACACTGGATGGCCGCGAGGGATGGGTGGCATATTGGGACAGGGCACCCTGGTGACAGTGAGCTCC |
| 165. | 18596 | V_HCDR1 | Protein | GVTFNYYG |
| 166. | 18596 | V_HCDR3 | Protein | TLDGREGWVAY |

TABLE E-continued

| SEQ ID No. | Variant number | Domain | Sequence Type | Sequence |
|---|---|---|---|---|
| 167. | 18596 | V_HCDR2 | Protein | ITNSGGRI |
| 168. | 18596 | V_L | Protein | NFMLTQPHSVSESPGKTVTISCKRNTGNIGSN YVNWYQQHEGSSPTTIIYRDDKRPDGVSDRFS GSIDRSSKSASLTISNLKTEDEADYFCQSYSSG FIFGGGTKLTVL |
| 169. | 18596 | V_L | DNA | AACTTTATGCTGACCCAGCCACACTCCGTGT CTGAGAGCCCCGGCAAGACCGTGACAATCA GCTGTAAGAGAAACACAGGCAATATCGGCT CCAACTACGTGAATTGGTATCAGCAGCACG AGGGCTCTAGCCCTACCACAATCATCTACC GGGACGATAAGCGGCCCGACGGCGTGAGC GATCGGTTCTCCGGCTCTATCGACAGATCCT CTAAGAGCGCCTCCCTGACCATCTCTAATCT GAAGACAGAGGACGAGGCCGATTACTTTTG TCAGAGCTATAGCTCCGGCTTCATCTTTGGA GGAGGAACCAAGCTGACAGTGCTG |
| 170. | 18596 | V_LCDR1 | Protein | TGNIGSNY |
| 171. | 18596 | V_LCDR3 | Protein | QSYSSGFI |
| 172. | 18596 | V_LCDR2 | Protein | RDD |
| 173. | 21825 | V_H | Protein | EVQLVESGGGLVQPGGSLRLSCAASGVTFNY YGMSWIRQAPGKGLEWVASITRSGGRIYYPD SVKGRFTISRENTQKTLYLQMNSLRAEDTAV YYCTLDGREGWVAYWGQGTLVTVSS |
| 174. | 21825 | V_H | DNA | GAGGTGCAGCTGGTGGAGTCCGGAGGAGG ACTGGTGCAGCCTGGAGGCTCCCTGAGGCT GTCTTGCGCAGCCAGCGGAGTGACATTCAA CTACTATGGCATGAGCTGGATCAGACAGGC CCCAGGCAAGGGACTGGAGTGGGTGGCCTC CATCACCCGTCTGGCGGCAGAATCTACTA TCCCGACTCTGTGAAGGGCCGGTTTACAAT CAGCAGAGAGAACACCCAGAAGACACTGT ACCTGCAGATGAACAGCCTGCGGGCAGAGG ACACCGCCGTGTACTATTGCACACTGGATG GCAGAGAGGGATGGGTGGCATATTGGGGAC AGGGCACCCTGGTGACAGTGAGCTCC |
| 175. | 21825 | V_HCDR1 | Protein | GVTFNYYG |
| 176. | 21825 | V_HCDR3 | Protein | TLDGREGWVAY |
| 177. | 21825 | V_HCDR2 | Protein | ITRSGGRI |
| 178. | 21825 | V_L | Protein | QVVLTQPPSASGTPGQRVTISCKRNTGNIGSN YVNWYQQLPGTAPKLLIYRDDKRPDGVPDRF SGSKSGTSASLAISGLQSEDEADYYCQSYSSG FIFGGGTKLTVL |
| 179. | 21825 | V_L | DNA | CAGGTGGTGCTGACCCAGCCACCTAGCGCC TCCGGAACCCCTGGCCAGAGGGTGACAATC TCCTGTAAGCGCAACACCGGCAATATCGGC TCTAACTACGTGAATTGGTATCAGCAGCTG CCTGGCACAGCCCCAAAGCTGCTGATCTAC AGGGACGATAAGAGACCCGACGGCGTGCCT GATCGGTTTTCTGGCAGCAAGTCCGGCACC TCTGCCAGCCTGGCCATCAGCGGACTGCAG TCCGAGGACGAGGCAGATTACTATTGTCAG AGCTATTCTAGCGGCTTCATCTTTGGAGGAG GAACCAAGCTGACAGTGCTG |
| 180. | 21825 | V_LCDR1 | Protein | TGNIGSNY |
| 181. | 21825 | V_LCDR3 | Protein | QSYSSGFI |
| 182. | 21825 | V_LCDR2 | Protein | RDD |
| 183. | 19362 | V_H | Protein | EVQLVESGGGLVQPGGSLRLSCAASGVTFNY YGMSWIRQAPGKGLEWVASITNSGGRIYYPD SVKGRFTISRENTQKTLYLQMNSLRAEDTAV YYCTLDGRDGWVAYWGQGTLVTVSS |

TABLE E-continued

| SEQ ID No. | Variant number | Domain | Sequence Type | Sequence |
|---|---|---|---|---|
| 184. | 19362 | V<sub>H</sub> | DNA | GAGGTGCAGCTGGTGGAGTCCGGCGGCGGC CTGGTGCAGCCTGGAGGCTCCCTGAGGCTG TCTTGCGCAGCCAGCGGAGTGACCTTCAAC TACTATGGCATGTCCTGGATCAGACAGGCC CCAGGCAAGGGACTGGAGTGGGTGGCCTCC ATCACCAATTCTGGCGGCAGAATCTACTAT CCCGATTCTGTGAAGGGCAGGTTTACAATC AGCCGCGAGAACACCCAGAAGACACTGTAC CTGCAGATGAATAGCCTGCGGGCAGAGGAC ACCGCCGTGTACTATTGCACACTGGACGGC AGAGATGGATGGGTGGCATATTGGGGACAG GGCACCCTGGTGACAGTGAGCTCC |
| 185. | 19362 | V<sub>H</sub>CDR1 | Protein | GVTFNYYG |
| 186. | 19362 | V<sub>H</sub>CDR3 | Protein | TLDGRDGWVAY |
| 187. | 19362 | V<sub>H</sub>CDR2 | Protein | ITNSGGRI |
| 188. | 19362 | V<sub>L</sub> | Protein | NFMLTQPHSVSESPGKTVTISCKRNTGNIGSN YVNWYQQLPGTAPKTIIYRNDKRPDGVPDRF SGSIDSSSNSASLAISGLQSEDEADYYCQSYSS GFIFGGGTKLTVL |
| 189. | 19362 | V<sub>L</sub> | DNA | AACTTCATGCTGACCCAGCCCCACAGCGTG TCCGAGTCTCCTGGCAAGACCGTGACAATC TCCTGTAAGCGCAACACAGGCAATATCGGC TCTAACTACGTGAATTGGTATCAGCAGCTG CCAGGCACCGCCCCCAAGACAATCATCTAC CGGAACGACAAGAGACCTGATGGCGTGCCA GACCGGTTTAGCGGCTCCATCGATTCTAGC TCCAATTCTGCCAGCCTGGCCATCAGCGGAC TGCAGTCCGAGGACGAGGCAGATTACTATT GTCAGTCCTATTCTAGCGGCTTCATCTTTGG AGGAGGAACCAAGCTGACAGTGCTG |
| 190. | 19362 | V<sub>L</sub>CDR1 | Protein | TGNIGSNY |
| 191. | 19362 | V<sub>L</sub>CDR3 | Protein | QSYSSGFI |
| 192. | 19362 | V<sub>L</sub>CDR2 | Protein | RND |

Fc Clone Sequences

TABLE F

| SEQ ID No. | Clone | Domain | Sequence Type | Sequence | Start/End |
|---|---|---|---|---|---|
| 193. | 9620 | Full | Protein | EPKSSDKTHTCPPCPAPEAAGGPSVF LFPPKPKDTLMISRTPEVTCVVVSVS HEDPEVKFNWYVDGVEVHNAKTKP REEQYNSTYRVVSVLTVLHQDWLN GKEYKCKVSNKALPAPIEKTISKAK GQPREPQVYVLPPSRDELTKNQVSL LCLVKGFYPSDIAVEWESNGQPENN YLTWPPVLDSDGSFFLYSKLTVDKS RWQQGNVFSCSVMHEALHNHYTQK SLSLSPG | — |
| 194. | 9620 | Full | DNA | GAACCTAAAAGCAGCGACAAGAC CCACACATGCCCACCTTGTCCGGC GCCAGAGGCCGCCGGAGGACCATC CGTGTTCCTGTTTCCACCCAAGCCC AAGGATACCCTGATGATCTCTCGG ACCCCTGAGGTGACATGCGTGGTG GTGAGCGTGTCCCACGAGGACCCA GAGGTGAAGTTCAACTGGTACGTG GATGGCGTGGAGGTGCACAATGCC AAGACAAAGCCCCGGGAGGAGCA GTACAACTCTACCTATAGAGTGGT GAGCGTGCTGACAGTGCTGCACCA | — |

TABLE F-continued

| SEQ ID No. | Clone | Domain | Sequence Type | Sequence | Start/End |
|---|---|---|---|---|---|
| | | | | GGACTGGCTGAACGGCAAGGAGTA TAAGTGTAAGGTGTCCAATAAGGC CCTGCCCGCCCCTATCGAGAAAAC TATCAGCAAAGCCAAGGGCCAGCC AAGGGAACCACAGGTCTATGTCCT GCCACCATCTCGCGACGAGCTGAC CAAGAACCAGGTCTCACTGCTGTG TCTGGTGAAAGGATTCTATCCTTCC GATATTGCCGTGGAGTGGGAATCT AATGGCCAGCCAGAGAACAATTAC CTGACCTGGCCCCCTGTGCTGGAC AGCGATGGGTCCTTCTTTCTGTATT CAAAGCTGACAGTGGACAAAAGC AGATGGCAGCAGGGAAACGTCTTT AGCTGTTCCGTGATGCACGAAGCC CTGCACAATCATTACACCCAGAAG TCTCTGAGTCTGTCACCTGGC | |
| 195. | 9620 | CH2 | Protein | APEAAGGPSVFLFPPKPKDTLMISRT PEVTCVVVSVSHEDPEVKFNWYVD GVEVHNAKTKPREEQYNSTYRVVS VLTVLHQDWLNGKEYKCKVSNKAL PAPIEKTISKAK | A16-K125 |
| 196. | 9620 | CH2 | DNA | GCGCCAGAGGCCGCCGGAGGACC ATCCGTGTTCCTGTTTCCACCCAAG CCCAAGGATACCCTGATGATCTCT CGGACCCCTGAGGTGACATGCGTG GTGGTGAGCGTGTCCCACGAGGAC CCAGAGGTGAAGTTCAACTGGTAC GTGGATGGCGTGGAGGTGCACAAT GCCAAGACAAAGCCCCGGGAGGA GCAGTACAACTCTACCTATAGAGT GGTGAGCGTGCTGACAGTGCTGCA CCAGGACTGGCTGAACGGCAAGGA GTATAAGTGTAAGGTGTCCAATAA GGCCCTGCCCGCCCCTATCGAGAA AACTATCAGCAAAGCCAAG | – |
| 197. | 9620 | CH3 | Protein | GQPREPQVYVLPPSRDELTKNQVSL LCLVKGFYPSDIAVEWESNGQPENN YLTWPPVLDSDGSFFLYSKLTVDKS RWQQGNVFSCSVMHEALHNHYTQK SLSLSPG | G126-G231 |
| 198. | 9620 | CH3 | DNA | GGCCAGCCAAGGGAACCACAGGTC TATGTCCTGCCACCATCTCGCGAC GAGCTGACCAAGAACCAGGTCTCA CTGCTGTGTCTGGTGAAAGGATTC TATCCTTCCGATATTGCCGTGGAGT GGGAATCTAATGGCCAGCCAGAGA ACAATTACCTGACCTGGCCCCCTG TGCTGGACAGCGATGGGTCCTTCT TTCTGTATTCAAAGCTGACAGTGG ACAAAAGCAGATGGCAGCAGGGA AACGTCTTTAGCTGTTCCGTGATGC ACGAAGCCCTGCACAATCATTACA CCCAGAAGTCTCTGAGTCTGTCAC CTGGC | – |
| 199. | 12153Full | | Protein | EPKSSDKTHTCPPCPAPEAAGGPSVF LFPPKPKDTLMISRTPEVTCVVVSVS HEDPEVKFNWYVDGVEVHNAKTKP REEQYNSTYRVVSVLTVLHQDWLN GKEYKCKVSNKALPAPIEKTISKAK GQPREPQVYVLPPSRDELTKNQVSL LCLVKGFYPSDIAVEWESNGQPENN YLTWPPVLDSDGSFFLYSKLTVDKS RWQQGNVFSCSVMHEALHNHYTQK SLSLSPG | – |
| 200. | 12153Full | | DNA | GAGCCAAAGAGCTCCGACAAGACC CACACATGCCCCCCTTGTCCGGCG CCAGAGGCAGCAGGAGGACCAAG CGTGTTCCTGTTTCCACCCAAGCCC AAAGACACCCTGATGATTAGCCGA | – |

TABLE F-continued

| SEQ ID No. | Clone Domain | Sequence Type | Sequence | Start/End |
|---|---|---|---|---|
| | | | ACCCCTGAAGTCACATGCGTGGTC GTGTCCGTGTCTCACGAGGACCCA GAAGTCAAGTTCAACTGGTACGTG GATGGCGTCGAGGTGCATAATGCC AAGACAAAACCCCGGGAGGAACA GTACAACAGCACCTATAGAGTCGT GTCCGTCCTGACAGTGCTGCACCA GGATTGGCTGAACGGCAAGGAATA TAAGTGCAAAGTGTCCAATAAGGC CCTGCCCGCTCCTATCGAGAAAAC CATTTCTAAGGCAAAAGGCCAGCC TCGCGAACCACAGGTCTACGTGCT GCCTCCATCCCGGGACGAGCTGAC AAAGAACCAGGTCTCTCTGCTGTG CCTGGTGAAAGGCTTCTATCCATC AGATATTGCTGTGGAGTGGGAAAG CAATGGGCAGCCCGAGAACAATTA CCTGACTTGGCCCCTGTGCTGGA CTCTGATGGGAGTTTCTTTCTGTAT TCTAAGCTGACCGTGGATAAAAGT AGGTGGCAGCAGGGAAATGTCTTT AGTTGTTCAGTGATGCATGAAGCC CTGCATAACCACTACACCCAGAAA AGCCTGTCCCTGTCCCCCGGA | |
| 201. | 12153CH2 | Protein | APEAAGGPSVFLFPPKPKDTLMISRT PEVTCVVVSVSHEDPEVKFNWYVD GVEVHNAKTKPREEQYNSTYRVVS VLTVLHQDWLNGKEYKCKVSNKAL PAPIEKTISKAK | A16-K125 |
| 202. | 12153CH2 | DNA | GCGCCAGAGGCAGCAGGAGGACC AAGCGTGTTCCTGTTTCCACCCAA GCCCAAAGACACCCTGATGATTAG CCGAACCCCTGAAGTCACATGCGT GGTCGTGTCCGTGTCTCACGAGGA CCCAGAAGTCAAGTTCAACTGGTA CGTGGATGGCGTCGAGGTGCATAA TGCCAAGACAAAACCCCGGGAGG AACAGTACAACAGCACCTATAGAG TCGTGTCCGTCCTGACAGTGCTGC ACCAGGATTGGCTGAACGGCAAGG AATATAAGTGCAAAGTGTCCAATA AGGCCCTGCCCGCTCCTATCGAGA AAACCATTTCTAAGGCAAAA | – |
| 203. | 12153CH3 | Protein | GQPREPQVYVLPPSRDELTKNQVSL LCLVKGFYPSDIAVEWESNGQPENN YLTWPPVLDSDGSFFLYSKLTVDKS RWQQGNVFSCSVMHEALHNHYTQK SLSLSPG | G126-G231 |
| 204. | 12153CH3 | DNA | GGCCAGCCTCGCGAACCACAGGTC TACGTGCTGCCTCCATCCCGGGAC GAGCTGACAAAGAACCAGGTCTCT CTGCTGTGCCTGGTGAAAGGCTTC TATCCATCAGATATTGCTGTGGAG TGGGAAAGCAATGGGCAGCCCGA GAACAATTACCTGACTTGGCCCCC TGTGCTGGACTCTGATGGGAGTTT CTTTCTGTATTCTAAGCTGACCGTG GATAAAAGTAGGTGGCAGCAGGG AAATGTCTTTAGTTGTTCAGTGATG CATGAAGCCCTGCATAACCACTAC ACCCAGAAAAGCCTGTCCCTGTCC CCCGGA | – |

In one aspect, the present technology provides a nucleic acid sequence encoding a heavy chain or a light chain of an immunoglobulin-related composition described herein. Also disclosed herein are recombinant nucleic acid sequences encoding any of the antibodies or antigen binding fragments described herein. In another aspect, the present technology provides a host cell or vector expressing any nucleic acid sequence encoding a heavy chain or a light chain of an immunoglobulin-related composition described herein.

In some aspects, the anti-CD3 immunoglobulin-related compositions described herein contain structural modifications to facilitate rapid binding and cell uptake and/or slow release. In some aspects, the anti-CD3 immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a F(ab)'$_2$ fragment is used to facilitate rapid binding and cell uptake and/or slow release.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO92/08495; WO91/14438; WO89/12624; U.S. Pat. No. 5,314,995; and EP0 396 387.

In any of the above embodiments of the immunoglobulin-related compositions of the present technology, the antibody or antigen binding fragment may be optionally conjugated to an agent selected from the group consisting of isotopes, dyes, chromogens, contrast agents, drugs, toxins, cytokines, enzymes, enzyme inhibitors, hormones, hormone antagonists, growth factors, radionuclides, metals, liposomes, nanoparticles, RNA, DNA, antioxidants, proteins, carbohydrates, lipids, chelating agents, stabilizers, or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985,566; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

Methods of Preparing Anti-CD3 Immunoglobulin-Related Compositions of the Present Technology General Overview. Initially, a target CD3 epitope is chosen to which an antibody of the present technology can be raised. Techniques for generating antibodies directed to such target antigens are well known to those skilled in the art. Examples of such techniques include, for example, but are not limited to, those involving display libraries, xeno or human, mice, hybridomas, and the like. The preparation of antibodies specific for CD3 is described herein.

It should be understood that recombinantly engineered antibodies and antibody fragments, e.g., antibody-related polypeptides, which are directed to CD3 are suitable for use in accordance with the present disclosure.

Anti-CD3 immunoglobulin-related compositions that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or other antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications,* pp. 127-149, 1998, Alan R. Liss, Inc.) so long as such a variant forms an operative antibody which recognizes CD3. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Monoclonal Antibody. In one embodiment of the present technology, the antibody is an anti-CD3 monoclonal antibody. For example, in some embodiments, the anti-CD3 monoclonal antibody may be a human or a mouse anti-CD3 monoclonal antibody. For preparation of monoclonal antibodies directed towards CD3, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci.* USA 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for CD3 or derivatives, fragments, analogs or homologs thereof. Alternatively, hybridomas expressing anti-CD3 monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., CD3 binding, can be used as expressed by the hybridoma, it can be bound to a molecule such as polyethylene glycol (PEG) to alter its properties, or a cDNA encoding it can be isolated, sequenced and manipulated in various ways. Other manipulations include substituting or deleting particular amino acyl residues that contribute to instability of the antibody during storage or after administration to a subject, and affinity maturation techniques to improve affinity of the anti-CD3 immunoglobulin-related composition to CD3.

Hybridoma Technique. In some embodiments, the antibody of the present technology is an anti-CD3 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Mono-* clonal Antibodies And T-Cell Hybridomas, 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-CD3 immunoglobulin-related compositions, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for CD3 or derivatives, fragments, analogs or homologs thereof. Other examples of phage display methods that can be used to make the antibodies of the present technology include those disclosed in Huston et al., *Proc. Natl. Acad. Sci U.S.A.*, 85: 5879-5883, 1988; Chaudhary et al., *Proc. Natl. Acad. Sci U.S.A.*, 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO90/02809; WO91/10737; WO92/01047; WO92/18619; WO93/11236; WO95/15982; WO95/20401; WO96/06213; WO92/01047 (Medical Research Council et al.); WO97/08320 (Morphosys); WO92/01047 (CAT/MRC); WO91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-CD3 Immunoglobulin-related Compositions. As noted above, the antibodies of the present technology can be produced through the application of recombinant DNA technology. Recombinant polynucleotide constructs encoding an anti-CD3 immunoglobulin-related composition of the present technology typically include an expression control sequence operably-linked to the coding sequences of anti-CD3 immunoglobulin chains, including naturally-associated or heterologous promoter regions. As such, another aspect of the technology includes vectors containing one or more nucleic acid sequences encoding an anti-CD3 immunoglobulin-related composition of the present technology. For recombinant expression of one or more of the polypeptides of the present technology, the nucleic acid containing all or a portion of the nucleotide sequence encoding the anti-CD3 immunoglobulin-related composition is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-CD3 immunoglobulin-related composition, and the collection and purification of the anti-CD3 immunoglobulin-related composition, e.g., cross-reacting anti-CD3 immunoglobulin-related compositions. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with CD3 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-CD3 immunoglobulin-related composition), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-CD3 immunoglobulin-related composition of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-CD3 immunoglobulin-related composition, etc.).

Another aspect of the present technology pertains to anti-CD3 immunoglobulin-related composition-expressing host cells, which contain a nucleic acid encoding one or more anti-CD3 immunoglobulin-related compositions. The recombinant expression vectors of the present technology can be designed for expression of an anti-CD3 immunoglobulin-related composition in prokaryotic or eukaryotic cells. For example, an anti-CD3 immunoglobulin-related composition can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-CD3 immunoglobulin-related composition, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-CD3 immunoglobulin-related composition, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-CD3 immunoglobulin-related composition expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-CD3 immunoglobulin-related composition can be expressed in insect cells using baculovirus expression vectors. Baculovirus vectors available for expression of polypeptides, e.g., anti-CD3 immunoglobulin-related composition, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding an anti-CD3 immunoglobulin-related composition of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-CD3 immunoglobulin-related composition of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-CD3 immunoglobulin-related composition can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-CD3 immunoglobulin-related composition or can be introduced on a separate vector. Cells stably transfected with the introduced nucleic acid can be identified by drug selection (e.g., cells that have incorporated the selectable marker gene will survive, while the other cells die).

A host cell that includes an anti-CD3 immunoglobulin-related composition of the present technology, such as a prokaryotic or eukaryotic host cell in culture, can be used to produce (i.e., express) the recombinant anti-CD3 immunoglobulin-related composition. In one embodiment, the method comprises culturing the host cell (into which a recombinant expression vector encoding the anti-CD3 immunoglobulin-related composition has been introduced) in a suitable medium such that the anti-CD3 immunoglobulin-related composition is produced. In another embodiment, the method further comprises the step of isolating the anti-CD3 immunoglobulin-related composition from the medium or the host cell. Once expressed, collections of the anti-CD3 immunoglobulin-related composition, e.g., the anti-CD3 immunoglobulin-related compositions or the anti-CD3 immunoglobulin-related composition-related polypeptides are purified from culture media and host cells. The anti-CD3 immunoglobulin-related composition can be purified according to standard procedures of the art, including HPLC purification, column chromatography, gel electrophoresis and the like. In one embodiment, the anti-CD3 immunoglobulin-related composition is produced in a host organism by the method of Boss et al., U.S. Pat. No. 4,816,397. Usually, anti-CD3 immunoglobulin chains are expressed with signal sequences and are thus released to the culture media. However, if the anti-CD3 immunoglobulin chains are not naturally secreted by host cells, the anti-CD3 immunoglobulin chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-CD3 immunoglobulin-related compositions, e.g., the anti-CD3 immunoglobulin-related composition coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-CD3 immunoglobulin-related composition of the present technology is a single-chain anti-CD3 antibody. According to the present technology, techniques can be adapted for the production of single-chain antibodies specific to CD3 (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology*, 203: 46-88, 1991; Shu, L. et al., *Proc. Natl. Acad. Sci. USA*, 90: 7995-7999, 1993; and Skerra et al., *Science* 240: 1038-1040, 1988.

Chimeric and Humanized Antibodies. In one embodiment, the anti-CD3 immunoglobulin-related composition of the present technology is a chimeric anti-CD3 immunoglobulin-related composition. In one embodiment, the anti-CD3 immunoglobulin-related composition of the present technology is a humanized anti-CD3 immunoglobulin-related composition. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-CD3 immunoglobulin-related compositions, such as chimeric and humanized monoclonal antibodies, comprising both human and non-human portions, can be made using standard recombinant DNA techniques, and are within the scope of the present technology. For some uses, including in vivo use of the anti-CD3 immunoglobulin-related composition of the present technology in humans as well as use of these agents in in vitro detection assays, it is possible to use chimeric or humanized anti-CD3 immunoglobulin-related compositions. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci.* USA 84: 3439-3443; Liu, et al., 1987. *J. Immunol.* 139: 3521-3526; Sun, et al., 1987. *Proc. Natl. Acad. Sci.* USA 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler et al., 1988. *J. Immunol.* 141: 4053-4060. For example, antibodies can be humanized using a variety of techniques including CDR-grafting (EP0 239 400; WO91/09967; U.S. Pat. Nos. 5,530,101; 5,585,089; 5,859,205; 6,248,516; EP460167), veneering or resurfacing (EP0 592 106; EP0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine anti-CD3 monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO86/01533; Cabilly et al. U.S. Pat. No. 4,816,567; Cabilly et al., European Patent Application 125, 023; Better et al. (1988) *Science* 240: 1041-1043; Liu et al. (1987) *Proc. Natl. Acad. Sci.* USA 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-CD3 immunoglobulin-related compositions that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for humanized anti-CD3 immunoglobulin-related compositions, such as heavy and light chain immunoglobulins.

CDR Antibodies. In some embodiments, the anti-CD3 immunoglobulin-related composition of the present technology is an anti-CD3 CDR antibody. Generally the donor and acceptor antibodies used to generate the anti-CD3 CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one need replace only as many as necessary to permit adequate binding of the resulting CDR-grafted antibody to CD3. Methods for generating CDR-grafted and humanized antibodies are taught by Queen et al. U.S. Pat. Nos. 5,585, 089; 5,693,761; 5,693,762; and Winter U.S. Pat. No. 5,225, 539; and EP0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-CD3 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-CD3 CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, CD3 and at least one other arm that specifically binds to a second target antigen. In some embodiments, the second target antigen is an antigen or an epitope present on a tumor, a B cell, a myeloid cell, a plasma cell, or a mast cell. Additionally or alternatively, in certain embodiments, the second target antigen is selected from the group consisting of CD20, CD19, CD23, CD80, CD14, CD15, CD16, CD123, NKp46 and KIR. In certain embodiments, the BsAbs are capable of binding to tumor cells that express the second target antigen on the cell surface. In some embodiments, the BsAbs have been engineered to facilitate killing of tumor cells by directing (or recruiting) cytotoxic T cells to a tumor site via TDCC.

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In other embodiments, the bispecific fusion protein is tetravalent, comprising, for example, an immunoglobulin (e.g., IgG) with two binding sites for one antigen and two identical scFv for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen is linked with an scFv that engages T cells (e.g., by binding CD3). In this way, T cells are recruited to a tumor site such that they can mediate cytotoxic killing of the tumor cells. See, e.g., Dreier et al., *J. Immunol.* 170:4397-4402 (2003); Bargou et al., *Science* 321:974-977 (2008).

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any anti-CD3 immunoglobulin disclosed herein. In some certain embodiments, scFvs are linked to the C-terminal end of the light chain of any anti-CD3 immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of an anti-CD3 immunoglobulin-related composition. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a $G_4S$ linker (SEQ ID NO: 234). In some certain embodiments, a BsAb of the present technology comprises a $(G_4S)_n$ linker, wherein n is 1, 2, 3, 4, 5, 6, 7, 8, 9, 10, 11, 12, 13, 14, 15 or more (SEQ ID NO: 235).

Fusion Proteins. In one embodiment, the anti-CD3 immunoglobulin-related composition of the present technology is a fusion protein. The anti-CD3 immunoglobulin-related compositions of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-CD3 immunoglobulin-related compositions. For instance, a region of additional amino acids, particularly charged amino acids, can be added to the N-terminus of the anti-CD3 immunoglobulin-related composition to improve stability and persistence during purification from the host cell or subsequent handling and storage. Also, peptide moieties can be added to an anti-CD3 immunoglobulin-related composition to facilitate purification. Such regions can be removed prior to final preparation of the anti-CD3 immunoglobulin-related composition. The addition of peptide moieties to facilitate handling of polypeptides are familiar and routine techniques in the art. The anti-CD3 immunoglobulin-related composition of the present technology can be fused to marker sequences, such as a peptide which facilitates purification of the fused polypeptide. In select embodiments, the marker amino acid sequence is a hexa-histidine peptide (SEQ ID NO: 236), such as the tag provided in a pQE vector (QIAGEN, Inc., Chatsworth, Calif), among others, many of which are commercially available. As described in Gentz et al., *Proc. Natl. Acad. Sci. USA* 86: 821-824, 1989, for instance, hexa-histidine (SEQ ID NO: 236) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.*, 270: 9459-9471, 1995.

Labeled Anti-CD3 immunoglobulin-related compositions. In one embodiment, the anti-CD3 immunoglobulin-related composition of the present technology is coupled with a label moiety, i.e., detectable group. The particular label or detectable group conjugated to the anti-CD3 immunoglobulin-related composition is not a critical aspect of the technology, so long as it does not significantly interfere with the specific binding of the anti-CD3 immunoglobulin-related composition of the present technology to CD3. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^3H$, $^{14}C$, $^{35}S$, $^{125}I$, $^{121}I$, $^{131}I$, $^{112}In$, $^{99}mTc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-CD3 immunoglobulin-related composition.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-CD3 immunoglobulin-related compositions. In this case, antigen-coated particles are agglutinated by samples comprising the target antibodies. In this format, none of the components need be labeled and the presence of the target antibody is detected by simple visual inspection.

Identifying and Characterizing the Anti-CD3 Immunoglobulin-Related Compositions of the Present Technology Methods for identifying and/or screening the anti-CD3 immunoglobulin-related compositions of the present technology. In one embodiment, anti-CD3 immunoglobulin-related compositions of the present technology are selected using display of CD3 on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP585 287; EP605522; EP616640; EP1024191; EP589 877; EP774 511; EP844 306. Methods useful for producing/selecting a filamentous bacteriophage particle containing a phagemid genome encoding for a binding molecule with a desired specificity has been described. See, e.g., EP774 511; U.S. Pat. Nos. 5,871,907; 5,969,108; 6,225,447; 6,291,650; 6,492,160.

In some embodiments, anti-CD3 immunoglobulin-related compositions of the present technology are selected using display of CD3 on the surface of a yeast host cell. Methods useful for the isolation of scFv polypeptides by yeast surface display have been described by Kieke et al., *Protein Eng.* 1997 November; 10(11): 1303-10.

In some embodiments, anti-CD3 immunoglobulin-related compositions of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

After selection of the desired anti-CD3 immunoglobulin-related compositions, it is contemplated that said antibodies can be produced in large volume by any technique known to those skilled in the art, e.g., prokaryotic or eukaryotic cell expression and the like. The anti-CD3 immunoglobulin-related compositions which are, e.g., but not limited to, anti-CD3 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of CD3 Binding. In some embodiments, a CD3 binding assay refers to an assay format wherein CD3 and an anti-CD3 immunoglobulin-related composition are mixed under conditions suitable for binding between the CD3 and the anti-CD3 immunoglobulin-related composition and assessing the amount of binding between the CD3 and the anti-CD3 immunoglobulin-related composition. The amount of binding is compared with a suitable control, which can be the amount of binding in the absence of the CD3, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of CD3 binding to anti-CD3 immunoglobulin-related composition are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-CD3 immunoglobulin-related composition is at least 1 percent greater than the binding observed in the absence of the candidate anti-CD3 immunoglobulin-related composition, the candidate anti-CD3 immunoglobulin-related composition is useful as an anti-CD3 immunoglobulin-related composition of the present technology.

Uses of the Anti-CD3 Immunoglobulin-Related Compositions of the Present Technology General. The anti-CD3 immunoglobulin-related compositions of the present technology are useful in methods known in the art relating to the detection and/or quantitation of CD3 (e.g., for use in measuring levels of CD3 within appropriate physiological samples, for use in diagnostic methods, for use in imaging the polypeptide, and the like). Antibodies or antigen binding fragments of the present technology are useful to isolate CD3 by standard techniques, such as affinity chromatography or immunoprecipitation. An anti-CD3 immunoglobulin-related composition of the present technology can facilitate the purification of immunoreactive CD3 species from biological samples, e.g., mammalian sera or cells as well as recombinantly-produced immunoreactive CD3 expressed in a host system. Moreover, anti-CD3 immunoglobulin-related compositions can be used to detect immunoreactive CD3 species (e.g., in plasma, intact cells, a cellular lysate or cell supernatant) in order to evaluate the abundance and pattern of expression of the immunoreactive CD3. The anti-CD3 immunoglobulin-related compositions of the present technology can be used diagnostically to monitor immunoreactive CD3 levels in tissue as part of a clinical testing procedure, e.g., to determine the efficacy of a given treatment regimen. As noted above, the detection can be facilitated by coupling (i.e., physically linking) the anti-CD3 immunoglobulin-related compositions of the present technology to a detectable substance.

Detection of CD3. An exemplary method for detecting the presence or absence of an immunoreactive CD3 in a biological sample involves obtaining a biological sample from a test subject and contacting the biological sample with an anti-CD3 immunoglobulin-related composition of the present technology capable of detecting an immunoreactive CD3 such that the presence of an immunoreactive CD3 is detected in the biological sample. Detection may be accomplished by means of a detectable label attached to the antibody.

The term "labeled" with regard to the anti-CD3 immunoglobulin-related composition is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-CD3 immunoglobulin-related compositions disclosed herein are conjugated to one or more detectable labels. For such uses, anti-CD3 immunoglobulin-related compositions may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled CD3-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive CD3 in a biological sample in vitro as well as in vivo. In vitro techniques for detection of an immunoreactive CD3 include enzyme linked immunosorbent assays (ELISAs), Western blots, immunoprecipitations, radioimmunoassay, and immunofluorescence. Furthermore, in vivo techniques for detection of an immunoreactive CD3 include introducing into a subject a labeled anti-CD3 immunoglobulin-related composition. For example, the anti-CD3 immunoglobulin-related composition can be labeled with a radioactive marker whose presence and location in a subject can be detected by standard imaging techniques. In one embodiment, the biological sample contains CD3 from the test subject.

Immunoassay and Imaging. An anti-CD3 immunoglobulin-related composition of the present technology can be used to assay immunoreactive CD3 levels in a biological sample (e.g., human plasma) using antibody-based techniques. For example, CD3 expression can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting CD3 expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein, rhodamine, and green fluorescent protein (GFP), as well as biotin.

In addition to assaying immunoreactive CD3 levels in a biological sample, anti-CD3 immunoglobulin-related compositions of the present technology may be used for in vivo imaging of CD3. Antibodies or antigen binding fragments useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-CD3 immunoglobulin-related compositions by labeling of nutrients for the relevant scFv clone.

An anti-CD3 immunoglobulin-related composition which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled anti-CD3 immunoglobulin-related composition will then accumulate at the location of cells which contain the specific target antigen. For example, labeled anti-CD3 immunoglobulin-related compositions of the present technology will accumulate within the subject in cells and tissues in which the CD3 has localized.

Thus, the present technology provides a diagnostic method of a medical condition, which involves: (a) assaying the expression of immunoreactive CD3 by measuring binding of an anti-CD3 immunoglobulin-related composition of the present technology in cells or body fluid of an individual; (b) comparing the amount of immunoreactive CD3 present in the sample with a standard reference, wherein an increase or decrease in immunoreactive CD3 levels compared to the standard is indicative of a medical condition.

Affinity Purification. The anti-CD3 immunoglobulin-related compositions of the present technology may be used to purify immunoreactive CD3 from a sample. In some embodiments, the antibodies or antigen binding fragments are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of an antibody polypeptide to a support. Accordingly, any of the conjugation methods and means disclosed herein with reference to conjugation of an antibody polypeptide to a solid support can also be applied for conjugation of a first support to a second support, where the first and second solid support can be the same or different.

Appropriate linkers, which can be cross-linking agents, for use for conjugating an antibody polypeptide to a solid support include a variety of agents that can react with a functional group present on a surface of the support, or with the antibody polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between an antibody polypeptide and the solid support. For example, a photolabile cross-linker, such as 3-amino-(2-nitrophenyl)propionic acid can be employed as a means for cleaving an antibody polypeptide from a solid support. (Brown et al., *Mol. Divers*, pp, 4-12 (1995); Rothschild et al., *Nucl. Acids Res.*, 24:351-66 (1996); and U.S. Pat. No. 5,643,722). Other cross-linking reagents are well-known in the art. (See, e.g., Wong (1991), supra; and Hermanson (1996), supra).

An antibody polypeptide can be immobilized on a solid support, such as a bead, through a covalent amide bond formed between a carboxyl group functionalized bead and the amino terminus of the antibody polypeptide or, conversely, through a covalent amide bond formed between an amino group functionalized bead and the carboxyl terminus of the antibody polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the antibody polypeptide is cleaved and can be removed. In such a case, the antibody polypeptide can be deposited as a beadless patch at the bottom of a well of a solid support or on the flat surface of a solid support. After addition of a matrix solution, the antibody polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the antibody polypeptide. Acid lability can also be changed. For example, trityl, monomethoxytrityl, dimethoxytrityl or trimethoxytrityl can be changed to the appropriate p-substituted, or more acid-labile tritylamine derivatives, of the antibody polypeptide, i.e., trityl ether and tritylamine bonds can be made to the antibody polypeptide. Accordingly, an antibody polypeptide can be removed from a hydrophobic linker, e.g., by disrupting the hydrophobic attraction or by cleaving trityl-ether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest (e.g., antibody polypeptide) to a solid support. Using such linkers, a first solid support, e.g., a bead, can be selectively cleaved from a second solid support, without cleaving the antibody polypeptide from the support; the antibody polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize an antibody polypeptide to the support. As desired, the linkage of the antibody polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with an antibody polypeptide, e.g., an antibody polypeptide containing an attached trityl group or with a second solid support having hydrophobic character.

A solid support can also be provided with a member of a specific binding pair and, therefore, can be conjugated to an antibody polypeptide or a second solid support containing a complementary binding moiety. For example, a bead coated with avidin or with streptavidin can be bound to an antibody polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either an antibody polypeptide or a solid support and, conversely, avidin or other biotin binding moiety would be incorporated into the support or the antibody polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

Therapeutic Use of Anti-CD3 immunoglobulin-related Compositions of the Present Technology. The immunoglobulin-related compositions (e.g., antibodies or antigen binding fragments thereof) of the present technology are useful for the treatment of a disease or condition described herein.

In one aspect, the present disclosure provides a method for treating a cancer in a subject in need thereof, comprising administering to the subject an effective amount of a bispecific antibody (or antigen binding fragment thereof) of the present technology. In some embodiments, the bispecific antibody or antigen binding fragment of the present technology binds to CD3 and a tumor-associated antigen. Examples of tumor-associated antigen include GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PlGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

Examples of cancers that can be treated by the bispecific antibodies of the present technology include, but are not limited to: lymphomas such as non-Hodgkin's lymphoma (NHL), mantle cell lymphoma (MCL), acute lymphoblastic leukemia (ALL), chronic lymphocytic leukemia (CLL), small lymphocytic lymphoma, pituitary tumors, acute myeloid leukemia, neuroblastoma, renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, or melanoma. In some embodiments, the bispecific antigen-binding molecules of the present technology are used to treat a B cell cancer (e.g., Hodgkin's lymphoma, non-Hodgkin's lymphoma (NHL), precursor B cell lymphoblastic leukemia/lymphoma, mature B cell neoplasms, B cell chronic lymphocytic leukemia/small lymphocytic lymphoma, B cell prolymphocytic leukemia, lymphoplasmacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma).

In some embodiments, the subject is human. Additionally or alternatively, in some embodiments, the antibody or antigen binding fragment of the present technology recruits T cells for TDCC against the cancer.

The compositions of the present technology may be employed in conjunction with other therapeutic agents useful in the treatment of cancer.

For example, the antibodies of the present technology may be separately, sequentially or simultaneously administered with at least one additional therapeutic agent selected from the group consisting of cytotoxic agents, chemotherapeutic agents, cytokines, growth inhibitory agents, kinase inhibitors, anti-angiogenic agents, cardioprotectants, immunostimulatory agents, immunosuppressive agents, protein tyrosine kinase (PTK) inhibitors, alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO2012007137, WO2005000889, WO2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof. The immunoglobulin-related compositions described herein may be administered alone or in combination with other types of treatments (e.g., radiation therapy, chemotherapy, hormonal therapy, immunotherapy and anti-tumor agents).

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intraarterially, intrathecally, intracapsularly, intraorbitally, intradermally, transtracheally, intracerebroventricularly, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies or antigen binding fragments of the present technology comprise pharmaceutical formulations which may be administered to subjects in need thereof in one or more doses. Dosage regimens can be adjusted to provide the desired response (e.g., a therapeutic response).

Typically, an effective amount of the antibody or antigen binding fragment compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-CD3 immunoglobulin-related compositions, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody or antigen binding fragment ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-CD3 immunoglobulin-related compositions may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 µg/mL to about 125 µg/mL, 100 µg/mL to about 150 µg/mL, from about 125 µg/mL to about 175 µg/mL, or from about 150 µg/mL to about 200 µg/mL. Alternatively, anti-CD3 immunoglobulin-related compositions can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

Toxicity. Optimally, an effective amount (e.g., dose) of anti-CD3 immunoglobulin-related composition described herein will provide therapeutic benefit without causing substantial toxicity to the subject. Toxicity of the anti-CD3 immunoglobulin-related composition described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-CD3 immunoglobulin-related composition described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Demonstration of Therapeutic or Prophylactic Activity. The immunoglobulin-related compositions described herein are tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art.

Various delivery systems are known and can be used to administer an anti-CD3 immunoglobulin-related composition described herein, e.g., encapsulation in liposomes, microparticles, microcapsules, recombinant cells capable of expressing the antigen-binding constructs, receptor-mediated endocytosis (see, e.g., Wu et al., *J. Biol. Chem.* 262: 4429-4432 (1987)), construction of a nucleic acid as part of a retroviral or other vector, etc. Methods of administration include but are not limited to intradermal, intramuscular, intraperitoneal, intravenous, subcutaneous, intranasal, epidural, and oral routes.

The immunoglobulin-related compositions of the present technology may be administered by any convenient route, for example by infusion or bolus injection, by absorption through epithelial or mucocutaneous linings (e.g., oral mucosa, rectal and intestinal mucosa, etc.) and may be administered together with other therapeutic agents. Administration can be systemic or local. Suitable routes of administration include intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it may be desirable to administer the immunoglobulin-related compositions of the present technology locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In other embodiments, the immunoglobulin-related compositions of the present technology can be delivered in a vesicle, in particular a liposome (see Langer, *Science* 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In some embodiments, the immunoglobulin-related compositions of the present technology can be delivered in a controlled release system. In one embodiment, a pump may be used (Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance. Smolen and Ball (eds.), Wiley, New York (1984); Ranger and Peppas, *J., Macromol. Sci. Rev. Macromol. Chem.* 23:61 (1983); see also Levy et al., Science 228:190 (1985); During et al., *Ann. Neurol.* 25:351 (1989); Howard et al., J. *Neurosurg.* 71:105 (1989)). In certain embodiments, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (*Science* 249:1527-1533 (1990)).

Pharmaceutical Compositions

According to the methods of the present technology, the anti-CD3 immunoglobulin-related composition can be incorporated into pharmaceutical compositions suitable for administration. The pharmaceutical compositions generally comprise recombinant or substantially purified antibody (or antigen binding fragment) and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Examples of pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

Pharmaceutically-acceptable esters include esters formed from carboxy, sulfonyloxy, and phosphonoxy groups present in the anti-CD3 antibody or antigen binding fragment, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-CD3 antibody (or antigen binding fragment) of the present technology can be present in unsalified or unesterified form, or in salified and/or esterified form, and the naming of such anti-CD3 antibody (or antigen binding fragment) is intended to include both the original (unsalified and unesterified) compound and its pharmaceutically-acceptable salts and esters. Also, certain embodiments of the present technology can be present in more than one stereoisomeric form, and the naming of such anti-CD3 antibody or antigen binding fragment is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-CD3 antibody (or antigen binding fragment), use thereof in the compositions is contemplated. Supplementary active compounds can also be incorporated into the compositions.

A pharmaceutical composition of the present technology is formulated to be compatible with its intended route of administration. The anti-CD3 immunoglobulin-related compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-CD3 immunoglobulin-related compositions can optionally be administered in combination with other agents that are at least partly effective in treating various cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-CD3 immunoglobulin-related composition of the present technology in the required amount in an appropriate solvent with one or a combination of ingredients enumerated above, as required, followed by filtered sterilization. Generally, dispersions are prepared by incorporating the anti-CD3 immunoglobulin-related composition into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies or antigen binding fragments of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-CD3 immunoglobulin-related composition can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Oral formulations can include standard carriers such as pharmaceutical grades of mannitol, lactose, starch, magnesium stearate, sodium saccharine, cellulose, magnesium carbonate, etc. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-CD3 immunoglobulin-related composition is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-CD3 immunoglobulin-related composition is formulated into ointments, salves, gels, or creams as generally known in the art.

The anti-CD3 immunoglobulin-related composition can also be prepared as pharmaceutical compositions in the form of suppositories (e.g., with conventional suppository bases such as cocoa butter and other glycerides) or retention enemas for rectal delivery.

In one embodiment, the anti-CD3 immunoglobulin-related composition is prepared with carriers that will protect the anti-CD3 immunoglobulin-related composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

The pharmaceutical compositions, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The formulation should suit the mode of administration.

In certain embodiments, the pharmaceutical composition is formulated in accordance with routine procedures as a pharmaceutical composition adapted for intravenous administration to humans. Typically, compositions for intravenous administration are solutions in sterile isotonic aqueous buffer. Where necessary, the pharmaceutical composition may also include a solubilizing agent and a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients may be mixed prior to administration.

In some embodiments, the pharmaceutical composition can be used for treating and/or preventing any CD3-related disease or condition as Muromonab-CD3/OKT3 can, e.g., acute rejection in patients with organ transplants. In certain embodiments, the pharmaceutical composition may be used for treating cancer for which the anti-CD3 immunoglobulin-related composition comprised therein is preferably a multispecific antibody, more preferably a bispecific antibody.

Kits

The present technology provides kits for the detection of CD3-expressing T-cells and/or treatment of cancers, comprising at least one immunoglobulin-related composition of the present technology (e.g., any antibody or antigen binding fragment described herein), or a functional variant (e.g., a substitutional variant) thereof. Optionally, the above described components of the kits of the present technology are packed in suitable containers and labeled for treatment of cancers. The above-mentioned components may be stored in unit or multi-dose containers, for example, sealed ampoules, vials, bottles, syringes, IV solution bags, and test tubes, as an aqueous, preferably sterile, solution or as a lyophilized, preferably sterile, formulation for reconstitution. When one or more components of the kit are provided as solutions, for example an aqueous solution, or a sterile aqueous solution, the container means may itself be an inhalant, nasal spray device, syringe, pipette, eye dropper, or other such like apparatus, from which the solution may be administered to a subject or applied to and mixed with the other components of the kit. In other embodiments, the kit can additionally comprise a suitable solvent for reconstitution of the lyophilized components.

The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

Additionally or alternatively, in some embodiments, the kits may comprise (a) an anti-CD3 immunoglobulin-related composition of the present technology and (b) one or more additional cytotoxic or therapeutic agents including, but not limited to those described herein.

The kits are useful for detecting the presence of an immunoreactive CD3-expressing T cell in a biological sample, e.g., any body fluid including, but not limited to, e.g., serum, plasma, lymph, cystic fluid, urine, stool, cerebrospinal fluid, ascitic fluid or blood and including biopsy samples of body tissue.

For example, the kit can comprise: one or more humanized, chimeric, or bispecific anti-CD3 antibodies of the present technology (or antigen binding fragments thereof) capable of binding CD3-expressing T cells in a biological sample; means for determining the amount of the CD3-expressing T cells in the sample; and means for comparing the amount of the immunoreactive CD3-expressing T cells in the sample with a standard. One or more of the anti-CD3 antibodies may be labeled. The kit components, (e.g., reagents) can be packaged in a suitable container. The kit can further comprise instructions for using the kit to detect the immunoreactive CD3-expressing T cells.

For antibody-based kits, the kit can comprise, e.g., 1) a first antibody, e.g. a humanized, chimeric or bispecific anti-CD3 antibody of the present technology (or an antigen binding fragment thereof), attached to a solid support, which binds to CD3; and, optionally; 2) a second, different antibody which binds to either CD3 or to the first antibody. The first antibody or the second antibody may be conjugated to a detectable label. The detectable label may comprise a radioactive label, a fluorescent label, or a chromogenic label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of CD3 in vitro or in vivo, or for treatment of cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative anti-CD3 immunoglobulin-related compositions of the present technology. The following Examples demonstrate the production of the anti-CD3 immunoglobulin-related compositions of the present technology, and characterization of their binding specificities and biological activities.

Example 1: Design, Expression and Purification of the Parental Rat-C3E-1 and Humanized C3E-1

Preparation of Rat Anti-Human CD3 Antibody

Construction of human CD3εδ expression vector. A control vector pcDNA3.1-DEST engineered as a destination vector was prepared using the Gateway Vector Conversion System (Thermo Fisher Scientific Inc., Waltham MA). A cDNA encoding the human CD3ε protein (NCBI Reference Sequence: NP_000724.1) was purchased from Sino Biological Inc. and cloned in the pcDNA3.1-DEST vector using Gateway LR Clonase Enzyme mix (Thermo Fisher Scientific Inc., Waltham MA) to construct hCD3ε-pcDNA3.1. A cDNA encoding the human CD3δ protein (NP_000723.1) was amplified by PCR using a human T cell-derived cDNA as a template according to a method known to those skilled in the art, and cloned in pcDNA3.1(+) (Thermo Fisher Scientific Inc., Waltham MA) to construct an expression vector hCD3δ-pcDNA3.1. For the large-scale preparation of each expression vector, Endofree Plasmid Giga Kit (Qiagen N.V., Hilden Germany) was used.

Immunization. For immunization, WKY/Izm female rats (Japan SLC, Inc., Hamamatsu, Japan) were used. First, both lower thighs of each rat were pretreated with hyaluronidase (Sigma-Aldrich Corp., St. Louis, MO). Then, the hCD3ε-pcDNA3.1 and hCD3δ-pcDNA3.1 expression vectors (described above) were intramuscularly injected at these pretreated sites. In vivo electroporation of these sites was subsequently carried out using ECM830 (BTX) and a two-needle electrode. The same in vivo electroporation step was repeated approximate once every two weeks. The lymph nodes or the spleens were then harvested from the rats and used in hybridoma preparation.

Hybridoma preparation. The lymph node cells or the spleen cells were electrically fused with mouse myeloma SP2/0-ag14 cells (ATCC, No. CRL-1 581) using LF301 Cell Fusion Unit (BEX Co., Ltd.). The fused cells were diluted with ClonaCell-HY Selection Medium D (StemCell Technologies Inc., Vancouver, Canada) and cultured. Hybridoma colonies were recovered to prepare monoclonal hybridomas. Each hybridoma colony thus recovered was cultured using ClonaCell-HY Selection Medium E (StemCell Technologies Inc., Vancouver, Canada), and the resulting hybridoma culture supernatant was used to screen for an anti-human CD3 antibody-producing hybridoma.

Antibody screening by Cell-ELISA. HEK293a cells (stable expression HEK293-derived cell line expressing integrin αv and integrin β3) were adjusted to $7.5 \times 10^5$ cells/mL in a DMEM medium containing 10% FBS. hCD3ε-pcDNA3.1 and hCD3δ-pcDNA3.1, or a control pcDNA3.1-DEST was transfected thereto according to transfection procedures using Lipofectamine 2000 (Thermo Fisher Scientific Inc., Waltham MA). The resulting cells were dispensed in an amount of 100 μL/well to a 96-well plate (Corning Inc., Corning NY) and cultured overnight at 37° C. under 5% $CO_2$ conditions in a DMEM medium containing 10% FBS. The resulting transfected cells were used in the attached state in Cell-ELISA.

After removal of the culture supernatant from the expression vector-transfected HEK293α cells, each hybridoma culture supernatant was added to the hCD3ε-pcDNA3.1- and hCD3δ-pcDNA3.1-, or pcDNA3.1-DEST-transfected HEK293α cells, and the plate was left standing at 4° C. for 1 hour. The cells in the wells were washed once with PBS containing 5% FBS. Then, anti-Rat IgG and HRP-Linked Whole Ab Goat (GE Healthcare Bio-Sciences Corp., Little Chalfont U.K.) diluted 500-fold with PBS containing 5% FBS was added, and the plate was left standing at 4° C. for 1 hour. The cells in the wells were washed twice with PBS containing 5% FBS. An OPD chromogenic solution (OPD solution (o-phenylenediamine dihydrochloride (Wako Pure Chemicals Industries, Ltd., Osaka, Japan) and $H_2O_2$ dissolved at concentrations of 0.4 mg/mL and 0.6% (v/v), respectively, in 0.05 M trisodium citrate and 0.1 M disodium hydrogen phosphate dodecahydrate, pH 4.5 were then added at a concentration of 100 μL/well. Color reaction was performed with occasional stirring and stopped by the addition of 1 M HCl at a concentration of 100 μL/well. Then, the absorbance was measured at 490 nm using a plate reader (ENVISION; PerkinElmer, Inc., Waltham MA). In order to select a hybridoma producing an antibody binding to human CD3 expressed on cell membrane surface, hybridomas that yielded a culture supernatant exhibiting higher absorbance for the hCD3ε-pcDNA3.1 and hCD3δ-pcDNA3.1 expression vector-transfected HEK293α cells compared with the control pcDNA3.1-DEST-transfected HEK293 cells were selected as anti-human CD3 antibody production-positive hybridomas.

Antibody screening based on activation of human T cells. The anti-CD3 antibody obtained from hybridoma was evaluated for its activation of T cells with the detection of a CD69 activation marker as an index. Human T cell line Jurkat cells (ATCC, No. TIB-152) were adjusted to a concentration of $5 \times 10^6$ cells/mL in an RPMI1640 medium containing FBS and added at a concentration of 100 μL/well to a 96-well plate. After removal of the supernatant by centrifugation, the culture supernatant of each anti-human CD3 antibody production-positive hybridoma selected by Cell-ELISA or a rat IgG isotype control antibody (R&D Systems, Inc., Minneapolis, MN) was added at a final concentration of 5 μg/mL to the Jurkat cells, and the plate was left standing at 37° C. for 30 minutes. Then, the cross-linker Goat Anti-rat IgG Fcγ Fragment specific (Jackson ImmunoResearch Laboratories, Inc., West Grove, PA) was added at a final concentration of 10 μg/well, and the cells were cultured overnight at 37° C. under 5% $CO_2$ conditions. On the next day, the supernatant was removed, and the cells in the wells were washed once with PBS containing 5% FBS. Then, PE Mouse Anti-Human CD69 antibody (BD Biosciences, Franklin Lakes, NJ) was added at a concentration of 20 μL/well, and the plate was left standing at 4° C. for 30 minutes. The cells in the wells were washed twice with PBS containing 5% FBS and then resuspended in PBS containing 5% FBS, followed by detection using a flow cytometer (FC500; Beckman Coulter Inc., Carlsbad, CA). The data was analyzed using Flowjo (Tree Star Inc.). The PE fluorescence intensity was plotted to a histogram. Hybridomas that yielded a sample exhibiting a shift to stronger fluorescence intensity in the fluorescence intensity histogram of PE than in the fluorescence intensity histogram of the rat IgG isotype control antibody were selected as anti-human CD3 antibody-producing hybridomas positive for the ability to activate human T cells.

Screening based on selective binding activity to human or monkey CD3 by flow cytometry. Lenti-X293T cells (Takara Bio Inc., Cat #632180, Shiga Prefecture, Japan) were added at a density of $5.3 \times 10^4$ cells/cm$^2$ to a 225-cm$^2$ flask and cultured overnight at 37° C. under 5% $CO_2$ conditions in a DMEM medium containing 10% FBS. On the next day, hCD3ε-pcDNA3.1 and hCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. On the next day, the expression vector-transfected Lenti-X293T cells were treated with TrypLE Express (Thermo Fisher Scientific Inc., Waltham MA), washed with DMEM containing 10% FBS, and then adjusted to a concentration of $5 \times 10^6$ cells/mL in PBS containing 5% FBS. The resulting cell suspension was used in flow cytometry analysis.

Flow cytometry analysis of binding activity to human CD3. The human CD3 binding specificity of the antibody produced by each hybridoma determined to be positive for the ability to activate human T cells was further confirmed by flow cytometry. Each Lenti-X293T cell suspension was added at a concentration of 100 μL/well to a 96-well U-bottomed microplate and centrifuged to remove the supernatant. The hCD3ε-pcDNA3.1- and hCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate (Sigma-Aldrich Corp., St. Louis, MO) diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D (Molecular Probes, Inc., Eugene OR), followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the hCD3ε-pcDNA3.1- and hCD3δ-pcDNA3.1-transfected Lenti-X293T cells than in the fluorescence intensity histogram of the control pcDNA3.1-DEST-transfected Lenti-X293T cells were selected as hybridomas producing antibodies binding to human CD3.

Construction of monkey CD3εδ expression vector. cDNAs encoding the monkey CD3ε protein (NCBI Reference Sequence: NP_001270544.1) and the monkey CD3δ protein (NCBI Reference Sequence: NP_001274617.1) were amplified by PCR using a monkey T cell-derived cDNA as a template according to a method known to those skilled in the art, and cloned in pcDNA3.1(+) (Thermo Fisher Scientific Inc., Waltham MA) to construct expression vectors cynoCD3ε-pcDNA3.1 and cynoCD3δ-pcDNA3.1.

Preparation of monkey antigen gene-expressing cells. Lenti-X293T cells were inoculated at a density of $5.3 \times 10^4$ cells/cm² to a 225-cm² flask and cultured overnight at 37° C. under 5% $CO_2$ conditions in a DMEM medium containing 10% FBS. On the next day, cynoCD3ε-pcDNA3.1 and cynoCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. The next day, the expression vector-transfected Lenti-X293T cells were treated with TrypLE Express, washed with DMEM containing 10% FBS, and then adjusted to a concentration of $5 \times 10^6$ cells/mL in PBS containing 5% FBS. The resulting cell suspension was used in flow cytometry analysis.

Flow cytometry analysis of binding activity to monkey CD3. The monkey CD3 binding specificity of the antibody produced by each hybridoma determined to produce the antibody binding to human CD3 was further confirmed by flow cytometry. Each Lenti-X293T cell suspension was added at a concentration of 100 μL/well to a 96-well U-bottomed microplate and centrifuged to remove a supernatant. The cynoCD3ε-pcDNA3.1- and cynoCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the cynoCD3ε-pcDNA3.1- and cynoCD3δ-pcDNA3.1-transfected Lenti-X293T cells than in the fluorescence intensity histogram of the control pcDNA3.1-DEST-transfected Lenti-X293T cells were selected as hybridomas producing antibodies binding to monkey CD3.

Preparation of human CD3δ gene-expressing cells. Lenti-X293T cells were inoculated at a density of $5.3 \times 10^4$ cells/cm² to a 225-cm² flask and cultured overnight at 37° C. under 5% $CO_2$ conditions in a DMEM medium containing 10% FBS. On the next day, hCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. The next day, the expression vector-transfected Lenti-X293T cells were treated with TrypLE Express, washed with DMEM containing 10% FBS, and then adjusted to a concentration of $5 \times 10^6$ cells/mL in PBS containing 5% FBS. The resulting cell suspension was used in flow cytometry analysis.

Flow cytometry analysis of binding activity against human CD3δ. The human CD3δ binding specificity of the antibody produced by each hybridoma determined to produce the antibody binding to monkey CD3 was further confirmed by flow cytometry. Each Lenti-X293T cell suspension was added at a concentration of 100 μL/well to a 96-well U-bottomed microplate and centrifuged to remove a supernatant. The hCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the hCD3δ-pcDNA3.1-transfected Lenti-X293T cells than in the fluorescence intensity histogram of the control pcDNA3.1-DEST-transfected Lenti-X293T cells were excluded as hybridomas producing antibodies binding to human CD3δ.

Flow cytometry analysis of binding activity to monkey T cell lines. The monkey T cell line binding specificity of the antibody produced by each antibody-producing hybridoma that was not excluded was further confirmed by flow cytometry. A cynomolgus monkey T cell line HSC-F (JCRB Cell Bank, No. JCRB1164) was adjusted to a concentration of $5 \times 10^6$ cells/mL in an RPMI1640 medium containing FBS and added at a concentration of 100 μL/well to a 96-well plate. After removal of the supernatant by centrifugation, the culture supernatant of the antibody-producing hybridoma that was not excluded, or a rat IgG isotype control antibody was added to the HSC-F cells, and the plate was left standing at 4° C. for 1 hour. The supernatant was then removed, and the cells in the wells were washed once with PBS containing 5% FBS, then suspended by the addition of Anti-Rat IgG FITC conjugate diluted 500-fold with PBS containing 5% FBS, and left standing at 4° C. for 1 hour. The cells were washed three times with PBS containing 5% FBS and then resuspended in PBS containing 5% FBS and 2 µg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the fluorescence intensity histogram of FITC than in the fluorescence intensity histogram of the rat IgG isotype control antibody were selected as hybridomas producing antibodies also binding to the monkey T cell line.

Isotyping of antibodies. C3-147 suggestive of binding to human and monkey CD3ε and also binding to a monkey T cell line, and having the high ability to activate human T cells was selected from among the rat anti-CD3 antibody-producing hybridomas, and identified by antibody isotyping. The isotype was determined using Rat Immunoglobulin Isotyping ELISA Kit (BD Pharmingen, Franklin Lakes, NJ). As a result, the isotype of the rat anti-CD3 monoclonal antibody C3-147 was confirmed to be IgG2b and λ chains.

Sequencing of cDNAs Encoding Variable Regions in Rat Anti-CD3 Antibodies (C3-147)

The cDNAs encoding the variable regions of the rat anti-CD3 antibody (C3-147) were sequenced using the following methods.

cDNA synthesis. Cell lysates (50 mM Tris-HCl (pH 7.5), 250 mM LiCl, 5 mM EDTA (pH 8), 0.5% lithium dodecyl sulfate (LiDS), and 2.5 mM dithiothreitol (DTT)) of the rat anti-CD3 antibody (C3-147)-producing hybridoma were mixed with oligo dT25-bound ("dT25" disclosed as SEQ ID NO: 237) magnetic beads of Dynabeads mRNA DIRECT Kit (Thermo Fisher Scientific Inc., Waltham MA) so that the mRNA was bound to the magnetic beads. Next, the magnetic beads were washed once each with mRNA washing solution A (10 mM Tris-HCl (pH 7.5), 0.15 M LiCl, 1 mM EDTA, 0.1% LiDS, and 0.1% Triton X-100) and a solution for cDNA synthesis (50 mM Tris-HCl (pH 8.3), 75 mM KCl, 3 mM MgCl2, 5 mM DTT, 0.5 mM dNTP, 0.2% Triton X-100, and 1.2 units of RNase inhibitor (Thermo Fisher Scientific Inc., Waltham MA)). Then, a cDNA was synthesized using a solution for cDNA synthesis supplemented with 12 units of SuperScript III Reverse Transcriptase (Thermo Fisher Scientific Inc., Waltham MA). The cDNA was subsequently washed with a 3' tailing reaction solution (50 mM potassium phosphate, 4 mM $MgCl_2$, 0.5 mM dGTP, 0.2% Triton X-100, and 1.2 units of RNase inhibitor), followed by 3' tailing reaction with a reaction solution supplemented with 48 units of recombinant Terminal Transferase (Roche Applied Science, Penzberg, Germany).

Amplification and sequencing of rat immunoglobulin heavy and light chain variable region gene fragments. The magnetic beads were washed with a TE solution (10 mM Tris-HCl (pH 7.5), 1 mM EDTA, and 0.1% Triton X-100). Then, the rat immunoglobulin heavy and light chain genes were amplified by 5'-RACE PCR. Specifically, the magnetic beads were transferred to a PCR reaction solution (0.2 µM primers, 0.2 mM dNTP, and 0.25 units of PrimeSTAR HS DNA Polymerase (Takara Bio Inc., Shiga Prefecture, Japan)) and subjected to 35 reaction cycles each involving 94° C. for 30 seconds and 68° C. for 90 seconds. The primer sets used are described below.

PCR Primer Set for Heavy Chain Gene Amplification

```
Sense primer Nhe-polyC-S
                                        (SEQ ID NO: 38)
5'-GCTAGCGCTACCGGACTCAGATCCCCCCCCCCCCCDN-3'

First antisense primer rIgγ-AS1
                                        (SEQ ID NO: 40)
5'-TCACTGAGCTGGTGAGAGTGTAGAGCCC-3'

Second antisense primer rIgγ-AS2
                                        (SEQ ID NO: 42)
5'-TCACCGAGCTGCTGAGGGTGTAGAGCCC-3'
```

PCR Primer Set for Light Chain Gene Amplification

```
Sense primer Nhe-polyC-S2
                                        (SEQ ID NO: 205)
5'-GCTAGCGCTACCGGACTCAGATCCCCCCCCCCCCCDN-3'

First antisense primer rIgL-AS1
                                        (SEQ ID NO: 206)
5'-TTCCACATCACTCGGGTAGAAATCAG-3'

Second antisense primer rIgγ-AS2
                                        (SEQ ID NO: 207)
5'-TAACACCAGGGTAGAAATCTGTCACCAT-3'
```

Sequence analysis was carried out on the nucleotide sequences of the fragments amplified by the PCR reaction. The primers used are described below.

```
Sense primer rIgγ-seq for heavy chain sequencing
                                        (SEQ ID NO: 208)
5'-CTGGCTCAGGGAAATAGCC-3'

Antisense primer rIgL-seq1 for light chain
sequencing
                                        (SEQ ID NO: 209)
5'-TCCCTGGAGCTCCTCAGT-3'

Antisense primer rIgL-seq2 for light chain
sequencing
                                        (SEQ ID NO: 210)
5'-GCCTTGTCAGTCTTGAGC-3'
```

The sequence analysis was carried out using a gene sequence analyzer ("ABI PRISM 3700 DNA Analyzer; Applied Biosystems, Inc." or "Applied Biosystems 3730xl Analyzer; Applied Biosystems, Inc."). The Dye Terminator Cycle Sequencing System with AmpliTaq DNA polymerase (Life Technologies Corp.) and GeneAmp 9700 (Applied Biosystems, Inc.) were used in sequencing reaction.

The nucleotide and amino acid sequences of the C3-147 heavy chain variable region and light chain variable region are provided below:

Nucleotide Sequence Encoding the Heavy Chain Variable Region of C3-147 (SEQ ID NO: 211)

```
GAGGTGCAGTTGGTGGAGTCTGGGGGAGGCCTGGTGCAGCCTGGAAGGG

CCCTGAAACTCTCCTGTGTAGTCTCTGGAGTCACATTCAATTACTACGG

GATGAGCTGGATCCGCCAGGCTCCAGGGAAGGGGCTGGAGTGGGTTGCA

TCCATTACTAATTCTGGTGGTAGAATTTACTATCCAGACTCTGTGAAGG

GCCGATTCACTATCTCCAGAGAAAATACACAAAAGACCCTATACCTACA

AATGAACAGTCTGAGGTCTGAGGACACGGCCACTTATTACTGTACTCTC
```

-continued

GATGGTCGCGATGGTTGGGTTGCTTACTGGGGCCAAGGCACTCTGGTCA

CTGTCTCTTCA

Amino Acid Sequence of the Heavy Chain Variable Region of C3-147 (SEQ ID NO: 212)

EVQLVESGGGLVQPGRALKLSCVVSGVTFNYYGMSWIRQAPGKGLEWVA

SITNSGGRIYYPDSVKGRFTISRENTQKTLYLQMNSLRSEDTATYYCTL

DGRDGWVAYWGQGTLVTVSS

Nucleotide Sequence Encoding the Light Chain Variable Region of C3-147 (SEQ ID NO: 213)

CAGTTTGTGCTTACTCAGCCAAACTCTGTGTCTACGAATCTCGGAACCA

CAGTCGAACTGTCTTGCAAGCGCAACACTGGGAACATTGGAAGCAATTA

TGTGAACTGGTACCAGCAGCATGAGGGAAGATCTCCCACCACTATTATT

TATAGGGATGATAAGAGACCAGATGGAGTTTCTGACAGGTTCTCTGGGT

CCATTGACAGATCTTCCAAGTCAGCCCTCCTGACAATCAATAATGTGCA

GACTGAAGATGAAGCTGACTACTTCTGTCAGTCTTACAGTAGTGGTTTT

ATTTTCGGCGGTGGAACCAAGCTCACTGTCCTA

Amino Acid Sequence of the Light Chain Variable Region of C3-147 (SEQ ID NO: 214)
QFVLTQPNSVSTNLGTTVELSCKRNTGNIG-SNYVNWYQQHEGRSPTTIIYRDDKRP DGVS-DRFSGSIDRSSKSALLTINNVQTEDEADYFCQSYSSG-FIFGGGTKLTVL Preparation of Rat Anti-CD3 scFv (Rat C3E-1) and its Humanized Form (hC3E-1)

Construction of rat antibody CD3 scFv expression vector (pRat C3E-1). A sense strand oligonucleotide (5' GTCACTGTCTCTTCAGGTGGAGGCGGTTCAGGCG-GAGGTGGCAGCGGCGGTGG CGG-GAGTCAGTTTGTGCTTACT 3' (SEQ ID NO: 215)) of a DNA fragment having 15-base additional sequences upstream and downstream of a DNA sequence encoding a linker to be inserted between the heavy chain variable region ($V_H$) and the light chain variable region ($V_L$) of C3-147, and an antisense strand oligonucleotide thereof (5' AGTAAGCACAAACTGACTCCCGC-CACCGCCGCTGCCACCTCCGCCTGAACCGCC TCCACCTGAAGAGACAGTGAC 3' (SEQ ID NO: 216)) were synthesized (Sigma-Aldrich Corp., St. Louis, MO), and adjusted to 100 pmol/μL. Then, 20 μL each of these oligonucleotides was mixed and left standing at 96° C. for 10 minutes, at 70° C. for 2 minutes, at 60° C. for 2 minutes, at 40° C. for 2 minutes, and at 30° C. for 2 minutes for annealing to prepare a DNA fragment of the linker to be inserted between $V_H$ and $V_L$. Next, a DNA fragment amplified by PCR to add a human IgG heavy chain signal sequence, the DNA fragment of $V_H$ of the rat anti-CD3 antibody C3-147 amplified by PCR, the DNA fragment of the linker to be inserted between VH and VL, and a DNA fragment amplified by PCR in which a DNA sequence encoding a FLAG-His tag was added to a region containing the C3-147 $V_L$ DNA sequence such that the FLAG-His tag was located at the carboxyl terminus, were ligated with a vector backbone derived from an expression vector pcDNA-3.3TOPO for animal cells (Thermo Fisher Scientific Inc., Waltham MA) using In-Fusion HD cloning kit (Clontech Laboratories, Inc., Mountain View, CA) to prepare an scFv expression vector pRat C3E-1 containing the following nucleotide sequence in ORF.

Nucleotide sequence encoding rat C3E-1
(SEQ ID NO: 217)
ATGAAACACCTGTGGTTCTTCCTCCTGCTGGTGGCAGCTCCCAGATGGG

TGCTGAGCGAGGTGCAGTTGGTGGAGTCTGGGGGAGGCCTGGTGCAGCC

TGGAAGGGCCCTGAAACTCTCCTGTGTAGTCTCTGGAGTCACATTCAAT

TACTACGGGATGAGCTGGATCCGCCAGGCTCCAGGGAAGGGGCTGGAGT

GGGTTGCATCCATTACTAATTCTGGTGGTAGAATTTACTATCCAGACTC

TGTGAAGGGCCGATTCACTATCTCCAGAGAAAATACACAAAAGACCCTA

TACCTACAAATGAACAGTCTGAGGTCTGAGGACACGGCCACTTATTACT

GTACTCTCGATGGTCGCGATGGTTGGGTTGCTTACTGGGGCCAAGGCAC

TCTGGTCACTGTCTCTTCAGGTGGAGGCGGTTCAGGCGGAGGTGGCAGC

GGCGGTGGCGGGAGTCAGTTTGTGCTTACTCAGCCAAACTCTGTGTCTA

CGAATCTCGGAACCACAGTCGAACTGTCTTGCAAGCGCAACACTGGGAA

CATTGGAAGCAATTATGTGAACTGGTACCAGCAGCATGAGGGAAGATCT

CCCACCACTATTATTTATAGGGATGATAAGAGACCAGATGGAGTTTCTG

ACAGGTTCTCTGGGTCCATTGACAGATCTTCCAAGTCAGCCCTCCTGAC

AATCAATAATGTGCAGACTGAAGATGAAGCTGACTACTTCTGTCAGTCT

TACAGTAGTGGTTTTATTTTCGGCGGTGGAACCAAGCTCACTGTCCTAG

GCGCGTCTGCGGCCGCAGGATCCGGTGGTGATTACAAAGATGATGACGA

TAAAGGTGCAGCGGCGCATCACCATCATCACCAC

Signal Sequence (1-57), Rat C3E-1 (58-867), FLAG-His Tag (784-867)

Expression and purification of rat anti-CD3 scFv (rat C3E-1). Expi293F cells (Thermo Fisher Scientific Inc., Waltham MA) were subcultured and cultured according to the manufacturer's manual. The scFv expression vector was transfected to the Expi293F cells in the logarithmic growth phase. The scFv was transiently expressed, filtered, and then used in purification. The purification was performed by two steps involving Ni affinity chromatography using His Trap Excel (GE Healthcare Bio-Sciences Corp., Little Chalfont U.K.) and gel filtration using Superdex 200 increase (GE Healthcare Bio-Sciences Corp., Little Chalfont U.K.). A peak corresponding to the molecular weight of the scFv monomer was recovered and used as a purified protein sample. For the purification, AKTA chromatography system was used, and all steps were performed at 4° C. HBSor (25 mM histidine/5% sorbitol, pH 5.0) was used as a buffer for the purified protein. The purified protein sample was applied to SEC for analysis to determine its purity and concentration. Then, the sample was used in various assays. The amino acid sequence in rat C3E-1 is described below:

Amino acid sequence in rat C3E-1
(SEQ ID NO: 218)
EVQLVESGGGLVQPGRALKLSCVVSGVTFNYYGMSWIRQAPGKGLEWVA

SITNSGGRIYYPDSVKGRFTISRENTQKTLYLQMNSLRSEDTATYYCTL

DGRDGWVAYWGQGTLVTVSSGGGGSGGGGSGGGGSQFVLTQPNSVSTNL

```
GTTVELSCKRNTGNIGSNYVNWYQQHEGRSPTTIIYRDDKRPDGVSDRF

SGSIDRSSKSALLTINNVQTEDEADYFCQSYSSGFIFGGGTKLTVLGAS

AAAGSGGDYKDDDDKGAAAHHHHHH
```

Rat C3E-1 (1-270), FLAG-His Tag (243-270); $V_H$ and $V_L$ CDR Sequences are Underlined Humanization design of rat anti-CD3 antibody. The molecular modeling of the variable regions of the rat antibody was performed according to a method known in the art as homology modeling (*Methods in Enzymology,* 203: 121-153, (1991)) using a commercially available protein three-dimensional structure analysis program Discovery Studio 3.5 (Dassault Systemes S.A., San Diego, CA). The humanization was performed by CDR grafting (*Proc. Natl. Acad. Sci. USA* 86, 10029-10033 (1989)). An acceptor antibody was selected from human subgroup consensus sequences specified by KABAT et al., Sequences of Proteins of Immunological Interest, 5th Ed. Public Health Service National Institutes of Health, Bethesda, MD. (1991)) or the germline sequences on the basis of amino acid identity within framework regions, expected immunogenicity prediction scores or physical properties, etc. Also, back mutation was selected with reference to criteria, etc., provided by Queen et al. (*PNAS* 86, 10029-10033 (1989)) through the use of the three-dimensional structure model constructed by the approach described above.

Design of humanized amino acid sequence rat C3E-1. The amino acid sequence of hC3E-1 serving as a humanized form of rat C3E-1 was designed with human subgroup consensus sequences γ3 and λ6 as acceptors. The amino acid sequence of hC3E-1 $V_H$ designed from the amino acid sequence of rat C3-147 $V_H$ (see above) by the replacement of arginine at amino acid position 16 with glycine, alanine at amino acid position 17 with serine, lysine at amino acid position 19 with arginine, valine at amino acid position 23 with alanine, valine at amino acid position 24 with alanine, serine at amino acid position 88 with alanine, and threonine at amino acid position 93 with valine is shown below:

```
Amino acid sequence of the heavy chain variable
region of hC3E-1
                                    (SEQ ID NO: 43)
EVQLVESGGGLVQPGGSLRLSCAASGVTFNYYGMSWIRQAPGKGLEWVA

SITNSGGRIYYPDSVKGRFTISRENTQKTLYLQMNSLRAEDTAVYYCTL

DGRDGWVAYWGQGTLVTVSS
```

CDR Sequences are Underlined

The amino acid sequence of hC3E-1 $V_L$ designed from the amino sequence of rat C3-147 $V_L$ (see above) by the replacement of glutamine at amino acid position 1 with asparagine, valine at amino acid position 3 with methionine, asparagine at amino acid position 8 with histidine, threonine at amino acid position 12 with glutamic acid, asparagine at amino acid position 13 with serine, leucine at amino acid position 14 with proline, threonine at amino acid position 16 with lysine, glutamic acid at amino acid position 19 with threonine, leucine at amino acid position 20 with isoleucine, arginine at amino acid position 43 with serine, leucine at amino acid position 75 with serine, asparagine at amino acid position 79 with serine, valine at amino acid position 81 with leucine, and glutamine at amino acid position 82 with lysine is shown below:

```
Amino acid sequence of the light chain variable
region of hC3E-1
                                    (SEQ ID NO: 48)
NFMLTQPHSVSESPGKTVTISCKRNTGNIGSNYVNWYQQHEGSSPTTII

YRDDKRPDGVSDRFSGSIDRSSKSASLTISNLKTEDEADYFCQSYSSGF

IFGGGTKLTVL
```

CDR Sequences are Underlined

Modification of humanized anti-CD3 scFv hC3E-1. In order to prepare variants having distinctive binding activity and cytotoxic activity while maintaining cross-reactivity with monkey CD3ε, variants were designed by the replacement of amino acids in the framework regions of $V_L$ of hC3E-1 with the corresponding ones in $V_L$ of scFv (sequence containing the four mutations A2S, S8P, V13A, and F80L in IGLV1-40*01).

Construction of humanized anti-CD3 scFv (hC3E-1) expression vector phC3E-1. A DNA fragment comprising a DNA sequence of scFv containing a hC3E-1 light chain (see above) connected to the carboxyl terminus of the hC3E-1 heavy chain (see above) via a 15-amino acid flexible linker was synthesized with 15-base additional sequences attached upstream and downstream (GeneArt Gene Synthesis Service/Thermo Fisher Scientific Inc., Waltham MA). A region containing the hC3E-1 DNA and additional sequences upstream and downstream was amplified by PCR using this DNA fragment as a template to obtain an insert DNA fragment. A vector region except for the scFv region was amplified by PCR using the expression vector pRat C3E-1 as a template to obtain a vector fragment. These DNA fragments were annealed using In-Fusion HD cloning kit (Clontech Laboratories, Inc., Mountain View, CA) to prepare a humanized anti-CD3 scFv expression vector phC3E-1 containing the following nucleotide sequence in ORF.

```
Nucleotide sequence encoding hC3E-1
                                    (SEQ ID NO: 219)
ATGAAACACCTGTGGTTCTTCCTCCTGCTGGTGGCAGCTCCCAGATGGG

TGCTGAGCGGAGAAGTGCAGCTGGTGGAATCCGGGGGGGGCCTGGTGCA

GCCTGGGGGGAGCCTGAGACTGAGTIGTGCCGCCTCTGGGGTGACATTT

AACTACTATGGCATGTCTTGGATCCGCCAGGCACCTGGAAAGGGCCTGG

AGTGGGTGGCCAGCATCACTAATTCCGGCGGGCGAATCTACTATCCCGA

CAGCGTCAAGGGCAGGTTCACAATTTCCCGCGAGAACACACAGAAAACT

CTGTACCTGCAGATGAATAGCCTGAGAGCCGAAGATACAGCTGTGTACT

ATTGCACTCTGGACGGCAGGGATGGGTGGGTCGCCTATTGGGGGCAGGG

AACCCTGGTGACAGTCAGCTCCGGAGGAGGAGGATCTGGCGGAGGAGGC

AGTGGGGGAGGCGGGTCAAACTTTATGCTGACCCAGCCCCACAGTGTGT

CAGAGAGCCCTGGCAAGACTGTCACCATCTCTTGTAAAAGGAACACCGG

AAATATTGGCAGTAACTACGTGAATTGGTATCAGCAGCATGAAGGGTCT

AGTCCAACCACAATCATCTACCGGGACGATAAGAGACCCGACGGGGTGT

CCGATCGATTCTCCGGATCTATCGACCGGTCAAGCAAGAGTGCTTCACT

GACCATTAGCAATCTGAAAACAGAGGACGAAGCAGATTACTTTTGCCAG

TCCTATTCCTCTGGCTTCATCTTTGGAGGCGGGACTAAACTGACCGTGC
```

-continued

TGGGCGCGGCCGCAGGTGCAGGTGGTGATTACAAAGATGATGACGATAA

AGGTGCAGCGGCGCATCACCATCATCACCAC

Signal Sequence (1-57), hC3E-1 (58-864), FLAG-His Tag (787-864)

hC3E-1 protein was purified as described herein.

In Vitro Activity of Humanized Anti-CD3 scFv

Study of binding activity of humanized anti-CD3 scFv (hC3E-1) to human CD3 by flow cytometry. Commercially available human PBMC (Cellular Technology Ltd. (CTL), Shaker Heights, OH) was adjusted to an appropriate concentration with PBS containing 5% FBS. LIVE/DEAD Fixable Near-IR Dead Cell Stain Kit (Thermo Fisher Scientific Inc., Waltham MA) and an anti-CD19 antibody (Beckman Coulter Inc., Carlsbad CA) were added to the cells, which were then left standing at 4° C. for 30 minutes. The cells were washed twice with PBS containing 5% FBS, then adjusted to a concentration of 1×10$^6$ cells/mL with PBS containing 5% FBS, added at a concentration of 100 µL/well to a 96-well U-bottomed microplate, and centrifuged to remove a supernatant. Humanized anti-CD3 scFv (hC3E-1) diluted with PBS containing 5% FBS was added at a concentration of 100 µL/well, and the plate was left standing at 4° C. for 60 minutes. The cells were washed twice with PBS containing 5% FBS. Then, Penta-His Alexa Fluor 488 (Qiagen N.V., Hilden Germany) diluted with PBS containing 5% FBS was added at a concentration of 30 µL/well, and the plate was left standing at 4° C. for 30 minutes. The cells were washed twice with PBS containing 5% FBS and then resuspended in PBS containing 5% FBS, followed by detection using a flow cytometer (FACSCanto™ II; Becton, Dickinson and Company, Franklin Lakes, NJ). The data was analyzed using Flowjo (Tree Star Inc.). The mean fluorescence intensity (MFI) of Alexa Fluor 488 in a fraction free of dead cells and CD19-positive cells was calculated. The MFI value of the scFv-unsupplemented sample was subtracted from the MFI value of the scFv-supplemented sample to calculate a relative value of MFI (rMFI). The tested humanized anti-CD3 scFv was found to bind to human CD3.

Study of binding activity of humanized anti-CD3 scFvs (hC3E-1) to human CD3 by SPR. The affinity of each humanized anti-CD3 scFv (hC3E-1) for CD3 was determined by the surface plasmon resonance method using BIAcore T-200 (GE Healthcare Bio-Sciences Corp., Little Chalfont U.K.). Five different concentrations of the scFv were injected into CD3 immobilized on a sensor chip. Rmax was estimated from the resulting response, and the antibody concentration that reached ½ thereof was defined as the dissociation constant of the scFv for CD3. As a result, the dissociation constant of the scFv (hC3E-1) for CD3 was 4.5 nM.

Preparation of cynomolgus monkey PBMC. PBMC was collected from the blood of a cynomolgus monkey according to the standard method using SepMate (StemCell Technologies Inc., Vancouver, Canada) and Lymphocyte Separation Solution (Nacalai Tesque Inc., Kyoto, Japan).

Study of binding activity of humanized anti-CD3 scFvs (hC3E-1) to cynomolgus monkey CD3 by flow cytometry. The cynomolgus monkey PBMC was adjusted to an appropriate concentration with PBS containing 5% FBS, and stained and analyzed according to the procedures described herein. The humanized anti-CD3 scFv (hC3E-1) was found to bind to cynomolgus monkey CD3 (at a 20 to 50 fold difference compared to binding with human CD3epsilon).

Example 2: Design, Expression and Purification of the Anti-CD3 Immunoglobulin-Related Compositions of the Present Technology Humanization and VL framework engineering of rat C3E-1. All constructs were monovalent scFv-heterodimer Fc molecules containing the heterodimeric Fc with an anti-CD3 scFv on one chain of the Fc. See FIG. 1. The heterodimeric Fc was constructed using known mutations in the CH3 domain (Von Kreudenstein et al., *MAbs.* 5(5):646-54 (2013)).

Figure 2A:
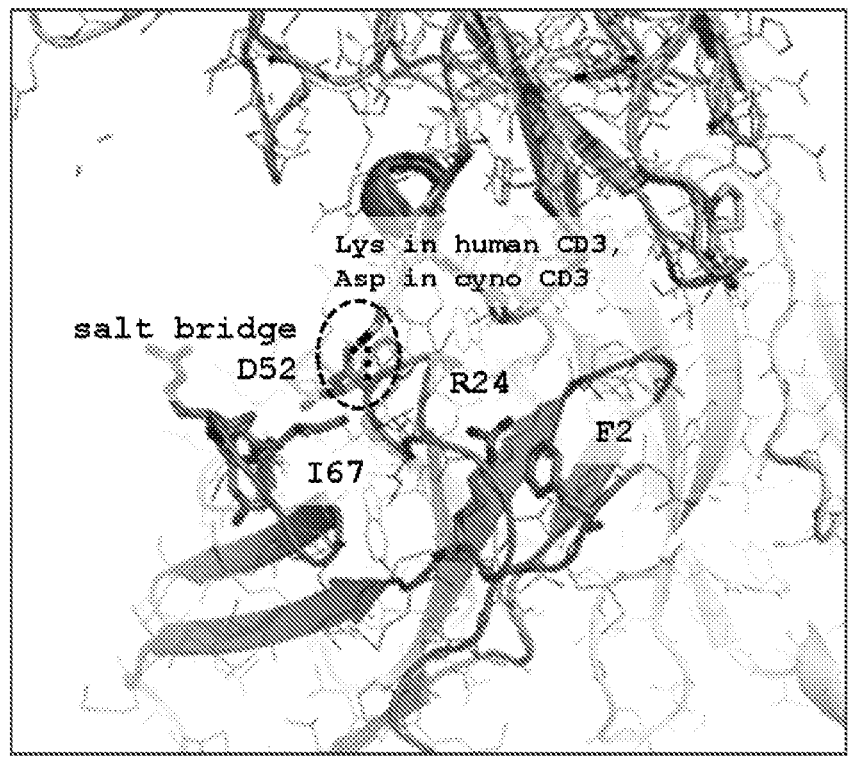
FIGS. 2a-2b illustrate the $V_L$ framework engineering strategy used to reduce binding of the anti-CD3 antibody hC3E-1 variant 18346 to human CD3, while retaining binding to cynomolgus monkey CD3.

Previous analysis of parental rat-C3E-1 and humanized C3E-1 binding to human CD3 epsilon and cynomolgus monkey CD3 epsilon showed a 20 to 50 fold difference in binding to human and cynomolgus CD3epsilon (see Example 1). In order to develop therapeutic antibodies and evaluate their activities in cynomolgus for toxicology studies, equivalent binding to the human and cynomolgus antigen can be desirable. To achieve equivalence in binding to human and cynomolgus CD3, a structure guided engineering and humanization approach was deployed (FIG. 2).

Structural analysis of the binding of rat C3E-1 to human CD3epsilon compared to the binding of rat C3E-1 to cynomolgus CD3epsilon revealed an important salt bridge between D52 in the light chain of C3E-1 and a Lysine residue in CD3epsilon (FIG. 2A) that is present in the human CD3 complex, but likely not the cynomolgus CD3 complex. Homology modelling and sequence comparison of human and cynomolgus CD3 epsilon showed that this Lysine in human CD3 is replaced by an Aspartic acid at the corresponding position in cynomolgus CD3epsilon. Thus, the stabilizing salt bridge will likely only be present in the complex of C3E-1 with human CD3epsilon, but not with cynomolgus CD3epsilon. While not wishing to be bound by theory, it is believed that the difference in binding affinity of C3E-1 to human and cynomolgus CD3epsilon may be attributed in part to the salt bridge between D52 in the light chain of C3E-1 and human CD3epsilon.

Figure 2B:
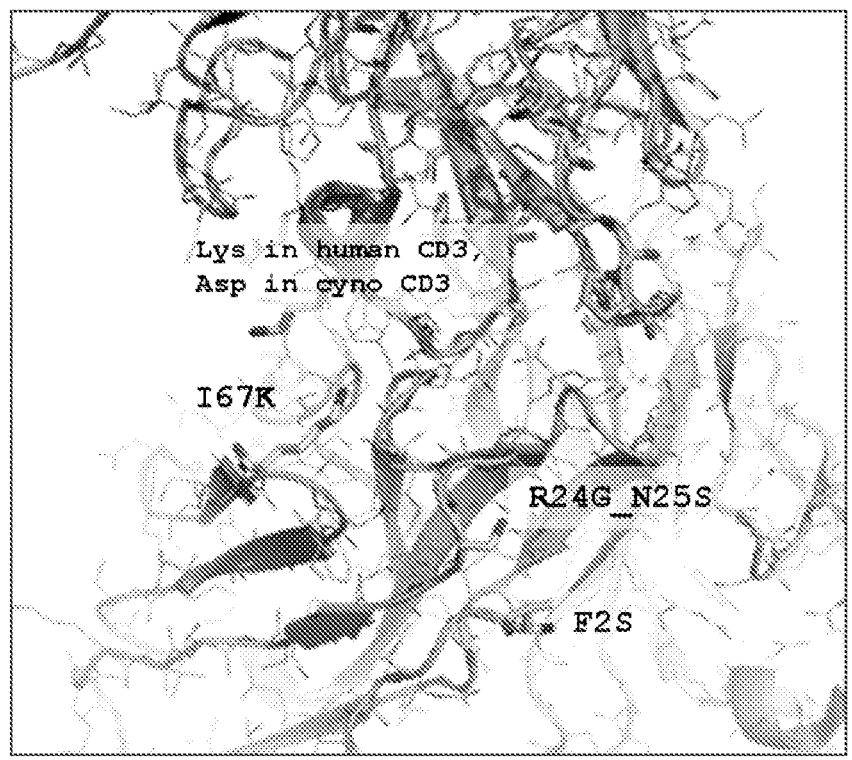
Figure 3A:
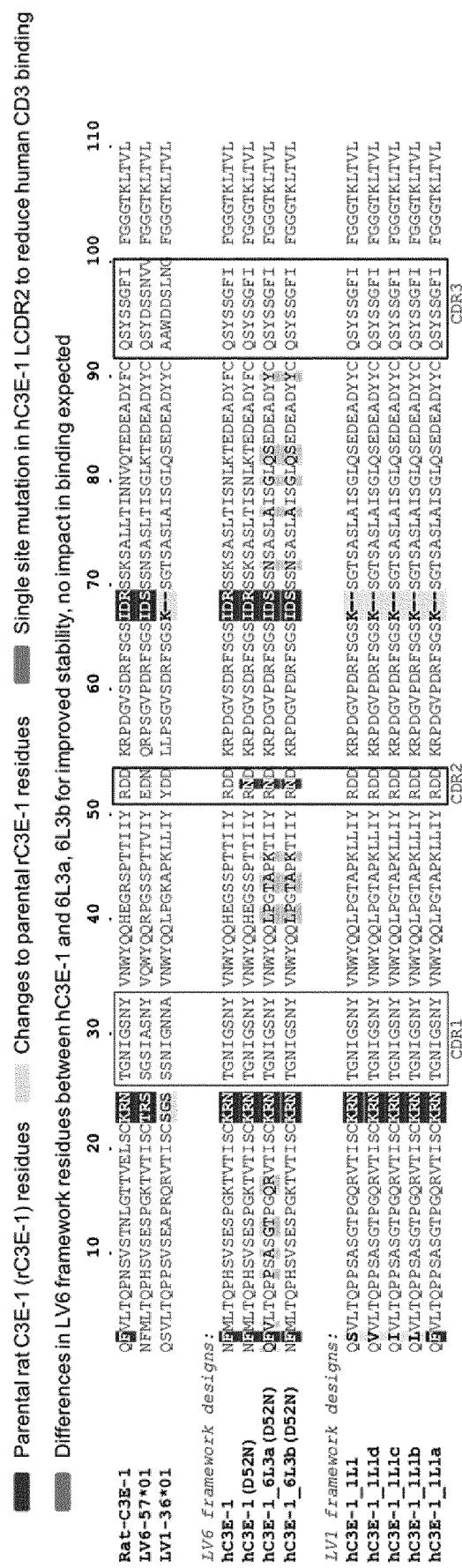
FIG. 3a depicts the amino acid residues targeted for substitution in hC3E-1 variable light chain ($V_L$) region.

To achieve equivalence in binding to human and cynomolgus CD3epsilon, attempts were made to knock out the D52 salt bridge because disrupting the D52 salt bridge may result in reduced binding of C3E-1 to human CD3epsilon, while having no impact on C3E-1 binding to cynomolgus CD3 epsilon (FIG. 2). Two different approaches were pursued to knock out the D52 salt bridge. The first approach entailed direct targeting of D52 by site-directed mutagenesis (D52N), while retaining the closest human framework V6. Additional mutations in the framework region were introduced to optimize stability of the humanized V6 designs (Table 1) and were not expected to impact binding (FIG. 2). The second approach entailed indirectly targeting the salt bridge by using a different $V_L$ framework that lacked D52 for humanization. As noted above, D52 is conserved in the human light chain V6 framework, but is absent in other human light chain frameworks. When using the next closest human light chain framework V1 for humanization, structural analysis as illustrated in FIG. 2, revealed three additional light chain positions that would influence the D52 salt bridge, but likely also influence the overall conformation of the CDRs and impact binding to both human and cynomolgus CD3 binding (FIG. 2 and FIG. 3a). To target the D52 salt bridge by humanization to framework V1 without impacting overall binding, three identified positions were modified:

amino acid position 2, amino acid position 24 and amino acid position 67, as illustrated in FIG. 2 and FIG. 3a.

Engineering of CDRs for reduced CD3 binding affinity. When developing bispecific CD3 targeting (T cell engaging) antibodies, it has been proposed that medium to low affinity for CD3 is important for functional activity (Bortoletto et al., *Eur. J. Immunol.* 32: 3102-3107 (2002); Zhong et al., *PNAS* 110 (17) 6973-6978 (2013); Leong et al., *Blood* 129(5): 609-618(2017)). hC3E-1 variants with a variety of binding affinities were generated so that they could be tested in functional assays to select the best affinity variant for a specific T cell engager. Mutations that lower the affinity of these constructs to human CD3 were introduced to reduce the binding of CD3 engagers to peripheral T cells, thus decreasing systemic cytokine release and toxicity traditionally observed with high affinity CD3 engagers. These mutations were not expected to significantly affect binding to cynomolgus CD3 and therefore should result in equivalent affinities for cynomolgus and human CD3.

Figure 3B:
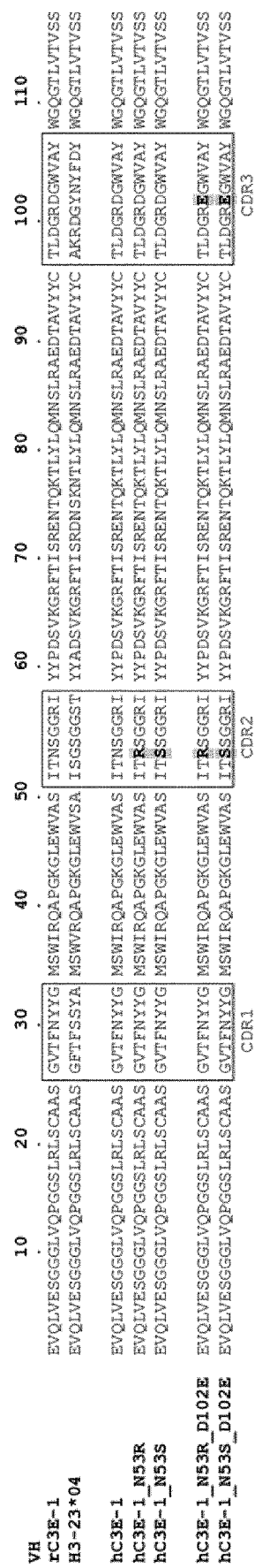
FIG. 3b depicts the amino acid residues targeted for substitution in hC3E-1 variable heavy chain ($V_H$) region.

Select CDR positions in the $V_H$ chain were targeted and analyzed for their impact on human and cynomolgus CD3 binding. One identified mutation in the $V_H$, D102E, is described in FIG. 3b. In addition, previously identified mutations to prevent de-amidation in the CDR2 of the heavy chain (N53R and N53S), were incorporated in the anti-CD3 constructs (see Example 1).

Example 3: Design, Expression and Purification of the Anti-CD3 Immunoglobulin-Related Compositions of the Present Technology The immunoglobulin-related compositions against CD3 were designed, expressed and characterized as described in WO2015/109131. Briefly, the genes encoding the antibody heavy chains were constructed via gene synthesis using codons optimized for human/mammalian expression. The scFv-Fc sequences were generated from the $V_H$ and $V_L$ sequences of hC3E-1 (See Example 1). The scFv variants made are described in Table 1. Additional variants are made as described in Table 1A.

TABLE 1

| Variant Number | VL Name | VL Mutations | VH Name | VH Mutations |
|---|---|---|---|---|
| 18346* | hC3E-1 | Wildtype | hC3E-1 | Wildtype |
| 18596 | hC3E-1 | Wildtype | hC3E-1a | D102E |
| 19363 | hC3E-1_6L3a (D52N) | N1Q_M3V_H8P_V10A_E12G_S13T_K16Q_T17R_H40L_E41P_S43T_S44A_T46K_D52N_S60P_R69S_K72N_T77A_N80G_K82Q_T83S_F90Y | hC3E-1 | — |
| 19362 | hC3E-1_6L3b (D52N) | H40L_E41P_S43T_S44A_T46K_D52N_S60P_R69S_K72N_T77A_N80G_K82Q_T83S_F90Y | hC3E-1 | — |
| 21826 | hC3E-1(D52N) | D52N | hC3E-1(N53R_D102E) | N53R_D102E |
| 21828 | hC3E-1(D52N) | D52N | hC3E-1(N53S_D102E) | N53S_D102E |
| 18343 | hC3E-1_1L1 | framework change (LV6 to LV1), F2S_G24R_I67K | hC3E-1** | — |
| 19373 | hC3E-1_1L1a | S2F_G24R_I67K | hC3E-1 | — |
| 19372 | hC3E-1_1L1b | S2L_G24R_I67K | hC3E-1 | — |
| 19371 | hC3E-1_1L1c | S2I_G24R_I67K | hC3E-1 | — |
| 19370 | hC3E-1_1L1d | S2V_G24R_I67K | hC3E-1 | — |
| 21825 | hC3E-1_1L1d | S2V_G24R_I67K | hC3E-1(N53R_D102E) | N53R_D102E |
| 21827 | hC3E-1_1L1d | S2V_G24R_I67K | hC3E-1(N53S_D102E) | N53S_D102E |
| 21829 | hC3E-1_1L1d | S2V_G24R_I67K | hC3E-1(N53R) | N53R |
| 21831 | hC3E-1_1L1d | S2V_G24R_I67K | hC3E-1(N53S) | N53S |

*Boldface refers to the "parent" variants for each framework upon which additional mutations were introduced to modify binding affinity or stability
Parent variant: 18346
Mutants of 18346 variant: 18596, 19363, 19362, 21826, 21828

**Boldface refers to the "parent" variants for each framework upon which additional mutations were introduced to modify binding affinity or stability
Parent variant: 18343
Mutants of 18343 variant: 19370, 19371, 19372, 19373, 21825, 21827, 21829, 21831

TABLE 1A

| Variant Number | VL Name | VL Mutations | VH Name | VH Mutations |
|---|---|---|---|---|
| 18346 | hC3E-1 | Wildtype | hC3E-1 | Wildtype** |
| 23790 | hC3E-1_6L3b (D52N) | H40L_E41P_S43T_S44A_T46K_D52N_S60P_R69S_K72N_T77A_N80G_K82Q_T83S_F90Y | hC3E-1(N53S) | N53S |
| 23791 | hC3E-1_6L3b (D52N) | H40L_E41P_S43T_S44A_T46K_D52N_S60P_R69S_K72N_T77A_N80G_K82Q_T83S_F90Y | hC3E-1(N53R) | N53R |
| 23792 | hC3E-1_6L3a (D52N) | N1Q_M3V_H8P_V10A_E12G_S13T_K16Q_T17R_H40L_E41P_S43T_S44A_T46K_D52N_S60P_R69S_K72N_T77A_N80G_K82Q_T83S_F90Y | hC3E-1(N53S) | N53S |

TABLE 1A-continued

| Variant | VL | | VH | |
|---|---|---|---|---|
| Number | Name | Mutations | Name | Mutations |
| 23793 | hC3E-1_6L3a (D52N) | N1Q_M3V_H8P_V10A_E12G_S13T_K16Q_T17R_H40L_E41P_S43T_S44A_T46K_D52N_S60P_R69S_K72N_T77A_N80G_K82Q_T83S_F90Y | hC3E-1(N53R) | N53R |

***Boldface refers to the "parent" variants for each framework upon which additional mutations are introduced to modify binding affinity or stability.
Parent variant: 18346
Mutants of 18346 variant: 23790, 23791, 23792, 23793

All tested variants have the following CH3 region mutations on an IgG1 scaffold: Heavy chain A: T350V_L351Y_F405A_Y407V; Heavy chain B: T350V_T366L_K392L_T394W. The anti-CD3 scFv chain is located on Chain A, the Fc fragment is located on Chain B. In addition, all variants have the following CH2 mutations to abolish FcγR binding: Chain A: D265S_L234A_L235A; Chain B: D265S_L234A_L235A. The N- to C-terminal order of the variable regions of anti-CD3 scFv is $V_H/V_L$, wherein the $V_H/V_L$ are connected by a (GGGGS)$_3$ linker (SEQ ID NO: 224).

Fc numbering is according to EU index described in Kabat referring to the numbering of the EU antibody (Edelman et al., *PNAS* 63:78-85 (1969)); Fab or variable domain numbering is according to absolute amino acid position. The variants described in Table 1 include variants v18346 and v18343, which were used as starting points to generate antigen-binding constructs with modified binding affinity and improved biophysical properties.

The $V_H$ and $V_L$ sequences of v18346 are identical to the $V_H$ and $V_L$ sequences of the antibody prepared in Example 1, hC3E-1. The $V_H$ sequence of v18343 is identical to $V_H$ sequence of the antibody prepared in Example 1, hC3E-1, while the $V_L$ sequence of v18343 was designed on a λ1 framework by introducing the following mutations into the $V_L$ sequence of rat C3E-1: F2S, N8P, V10A, T12G, N13T, L14P, T16Q, T17R, E19T, L20I, H40L, E41P, R43T, S44A, T46K, T47L, I48L S60P, I67K, D68_, R69_, S71K, K72T, L75S, T77A, N79S, N80G, V81L, T83S, F90Y. Variants 18596, 19362, 19363, 19370-19373, 21825-21829, 21831, and 23790-23793 exemplify designs that include modifications intended to generate distinct binding activity and cytotoxic activity while maintaining cross-reactivity to cynomolgus monkey CD3. The modifications include mutations to the framework and addition of CDR point mutations in the $V_H$ and $V_L$ sequences of v18346 and v18343. All variants include a heterodimeric Fc (Het Fc) and can be expressed with or without mutations in the CH2 domain (FcγR KO) to abolish Fc effector activity. Variants including this modification to the Fc are referred to as having an Fc knockout or Fc KO.

The final gene products were sub-cloned into the mammalian expression vector pTT5 (NRC-BRI, Canada) and expressed in CHO cells (Durocher, Y., Perret, S. & Kamen, A., *Nucleic acids research* 30, E9 (2002)). The CHO cells were transfected in exponential growth phase (1.5 to 2 million cells/mL) with aqueous 1 mg/mL 25 kDa polyethylenimine (PEI, Polysciences) at a PEI:DNA ratio of 2.5:1 (Raymond C. et al., *Methods*. 55(1):44-51 (2011)). To determine the optimal concentration range for forming heterodimers, the DNA was transfected in optimal DNA ratios of the heavy chain A (HC-A), and heavy chain B (HC-B) that allow for heterodimer formation (e.g., HC-A/HC-B/ratios=50: 50%). Transfected cells were harvested after 5-6 days with the culture medium collected after centrifugation at 4000 rpm and clarified using a 0.45 μm filter. The clarified culture medium was loaded onto a MabSelect SuRe protein-A column (GE Healthcare, Chicago, IL) and washed with 10 column volumes of PBS buffer at pH 7.2. The antibody was eluted with 10 column volumes of citrate buffer at pH 3.6 with the pooled fractions containing the antibody neutralized with Tris at pH 11. The protein was desalted using an Econo-Pac 10DG column (Bio-Rad Laboratories, Hercules, CA). In some cases, the protein was further purified by gel filtration, 3.5 mg of the antibody mixture was concentrated to 1.5 mL and loaded onto a Superdex 200 HiLoad 16/600 200 pg column (GE Healthcare, Chicago, IL) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL and stored at −80° C. The purity and yield of the final product was estimated by LC/MS and UPLC-SEC as described in detail in PCT/US2015/011664. All variants were expressed and purified to >95% heterodimer purity without contaminating homodimers.

Figure 4A:
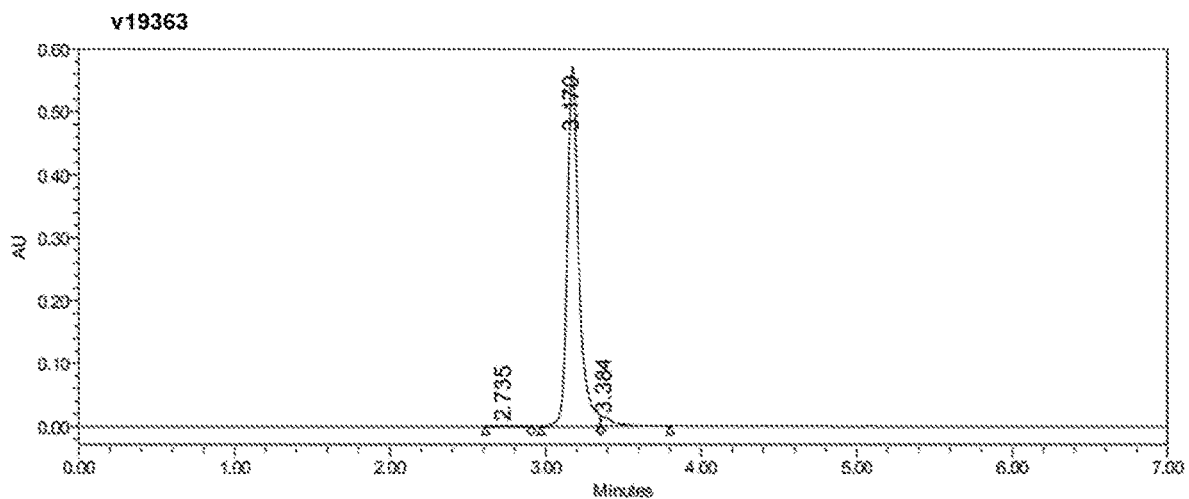
FIGS. 4a-4b depict the Size-Exclusion Ultra Performance Liquid Chromatography (UPLC-SEC) profiles of two exemplary monovalent anti-CD3 antibodies following Protein A affinity chromatography and gel filtration.
Figure 4B:
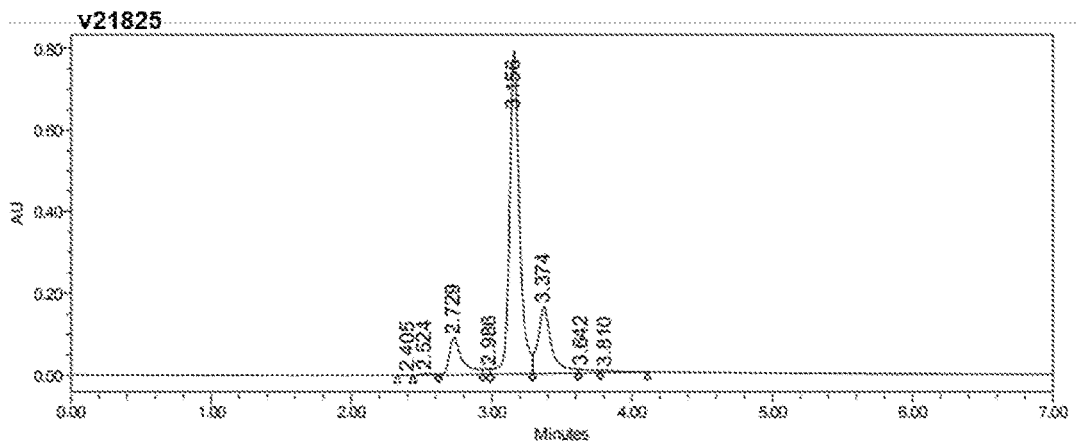
Figure 5A:
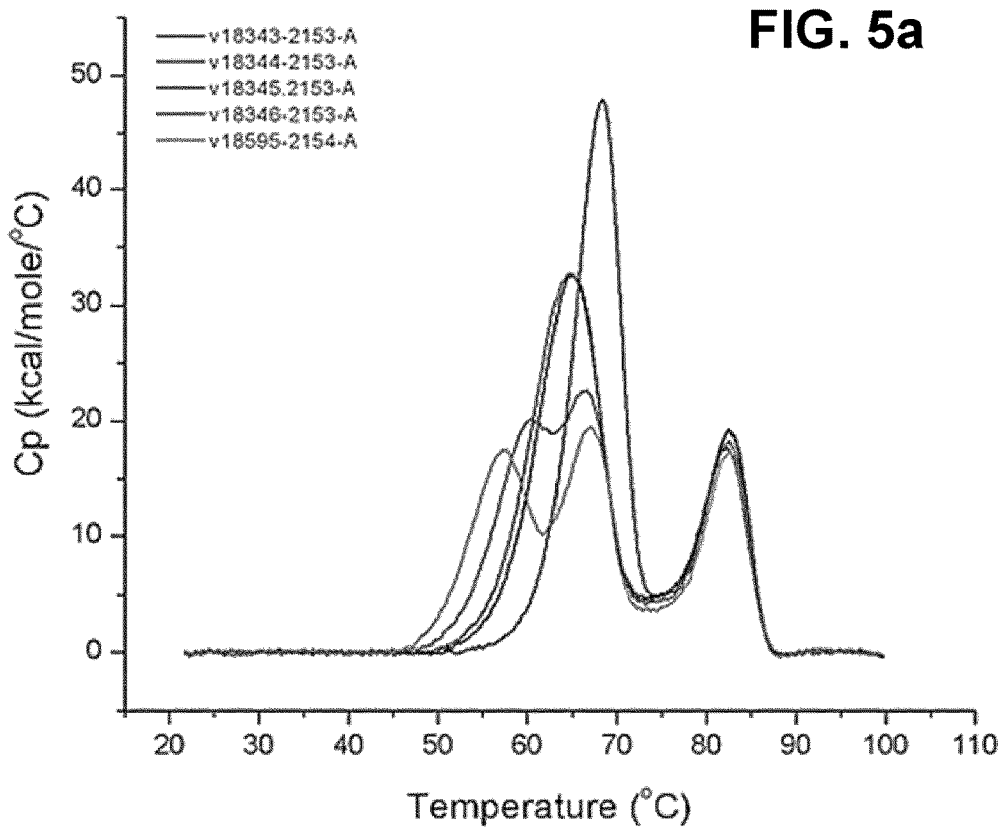
Figure 5B:
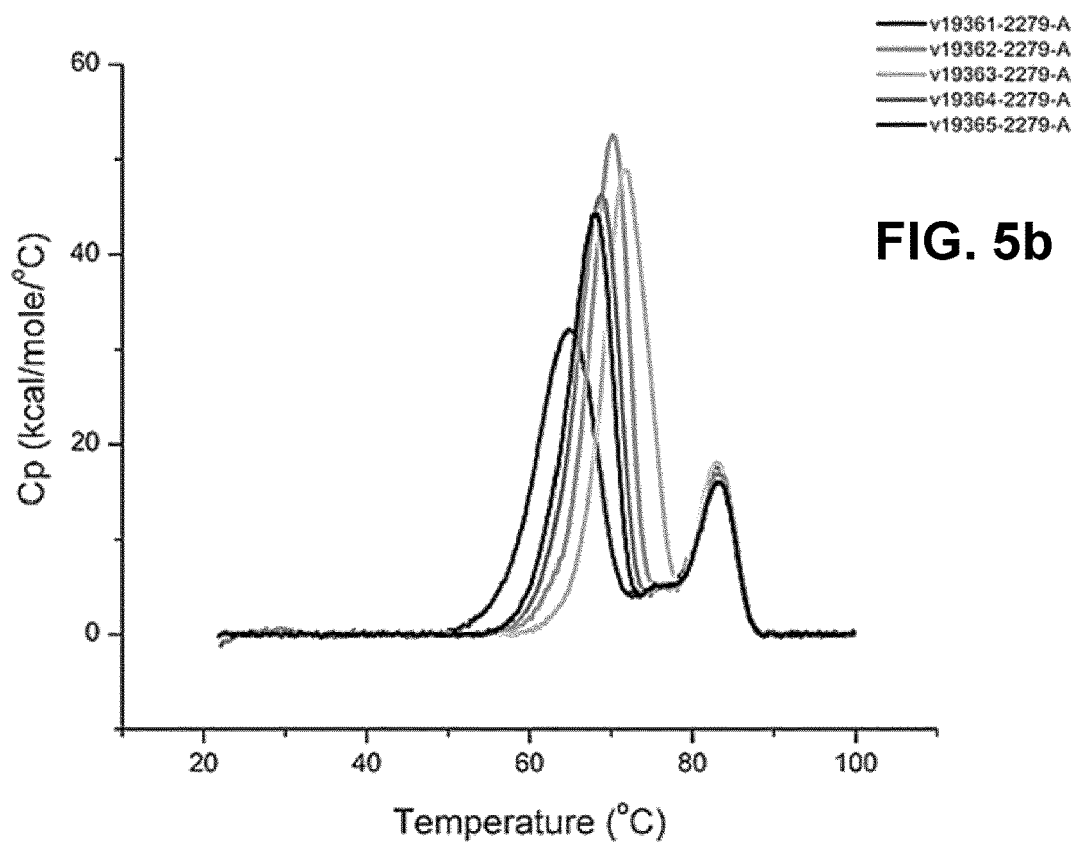
Figure 5C:
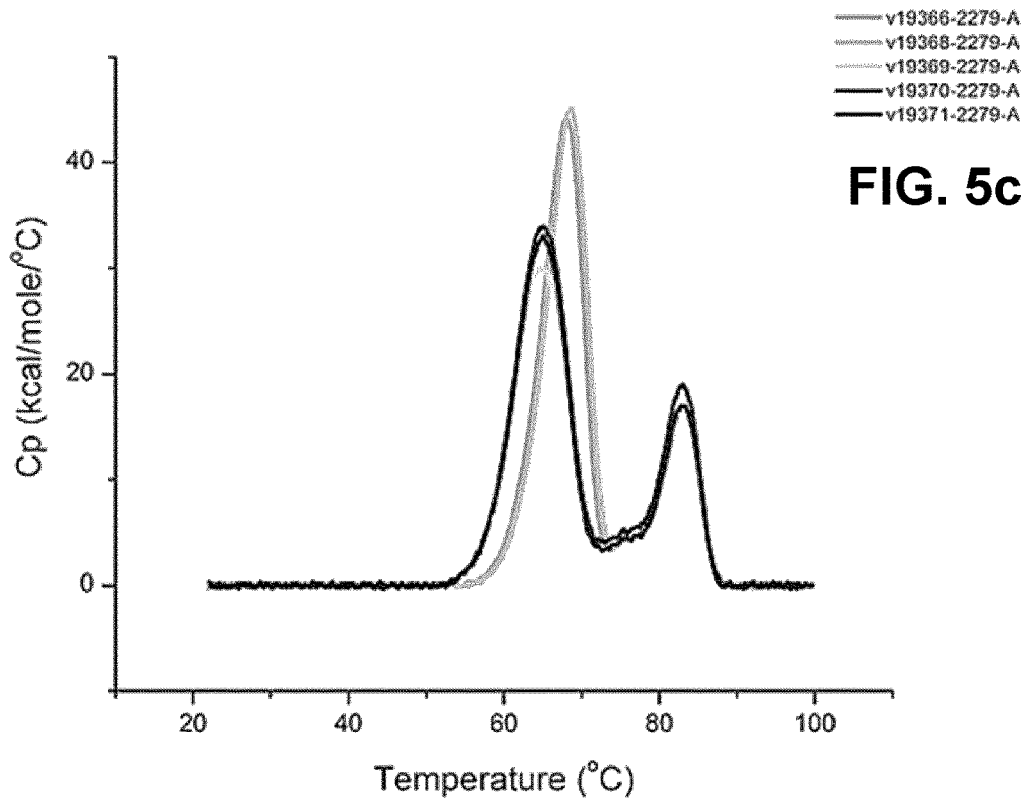
Figure 5D:
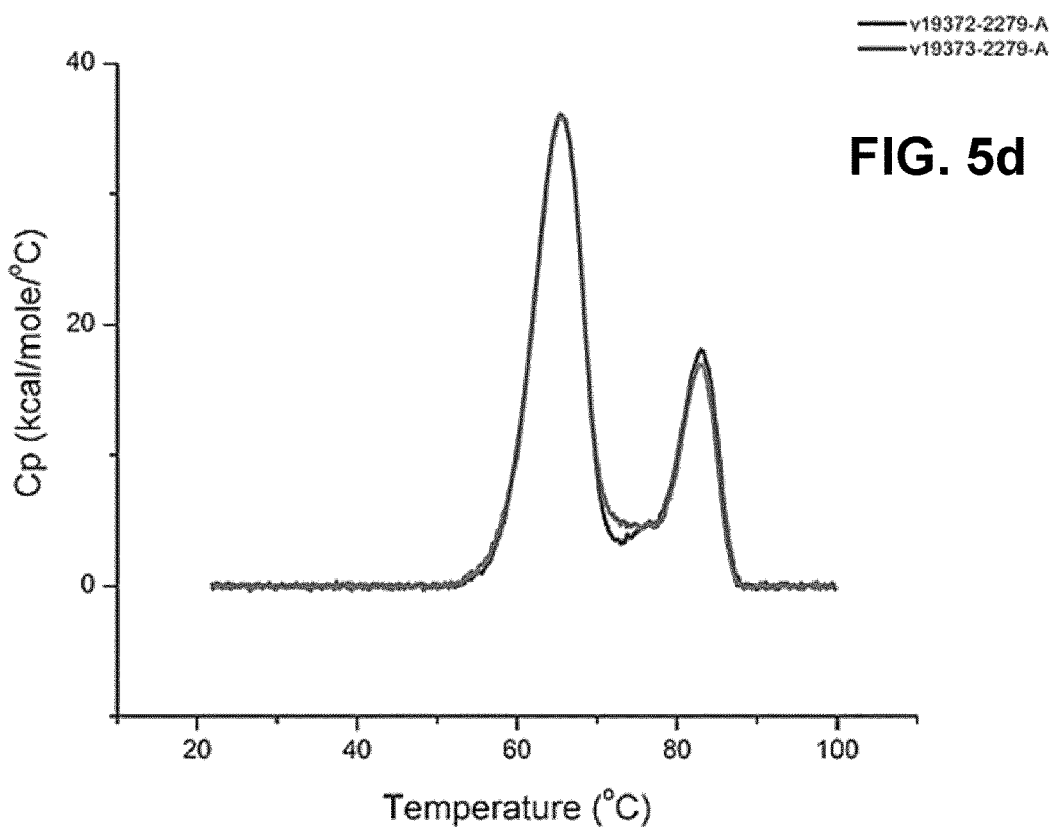
Figure 6A:
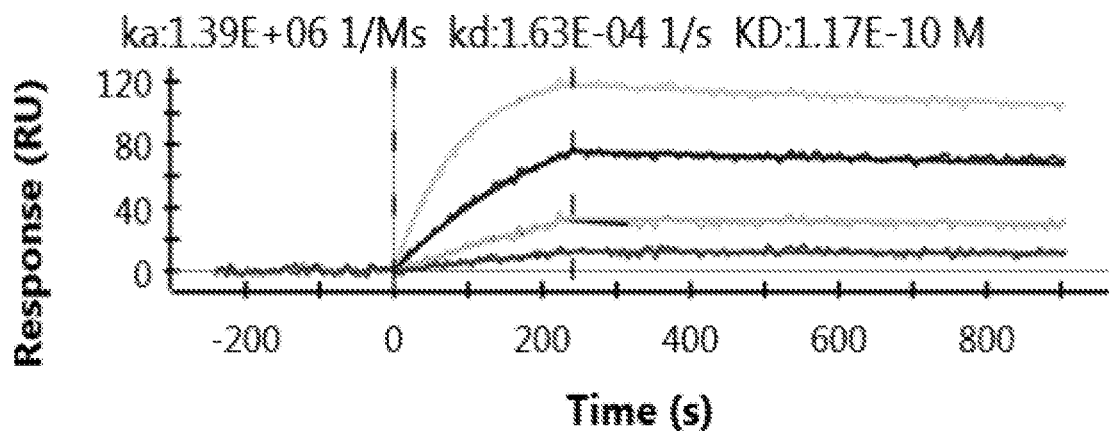
FIG. 6a depicts the binding isotherms for anti-CD3 parental variant 18346 in a surface plasmon resonance (SPR) binding assay.
Figure 6B:
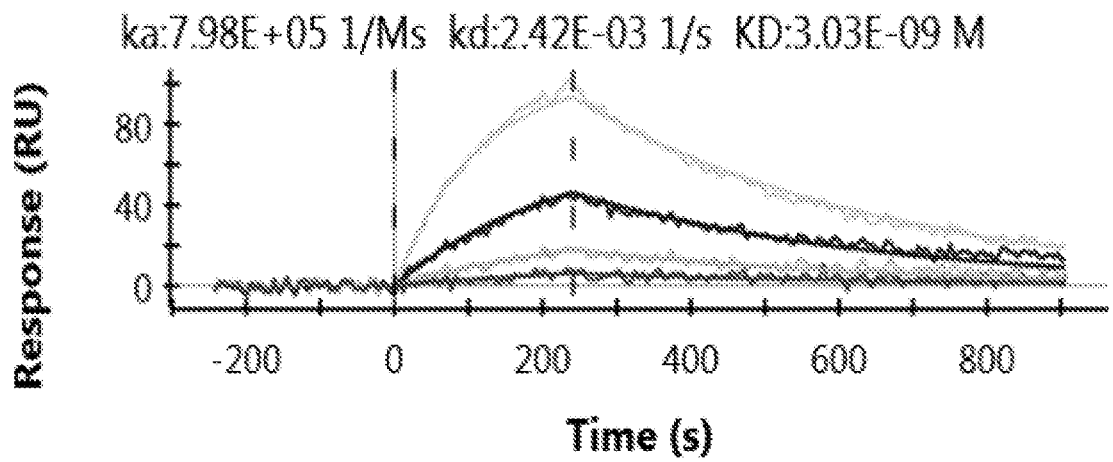
FIG. 6b depicts the binding isotherms for anti-CD3 variant 19362 in a surface plasmon resonance (SPR) binding assay.
Figure 6C:
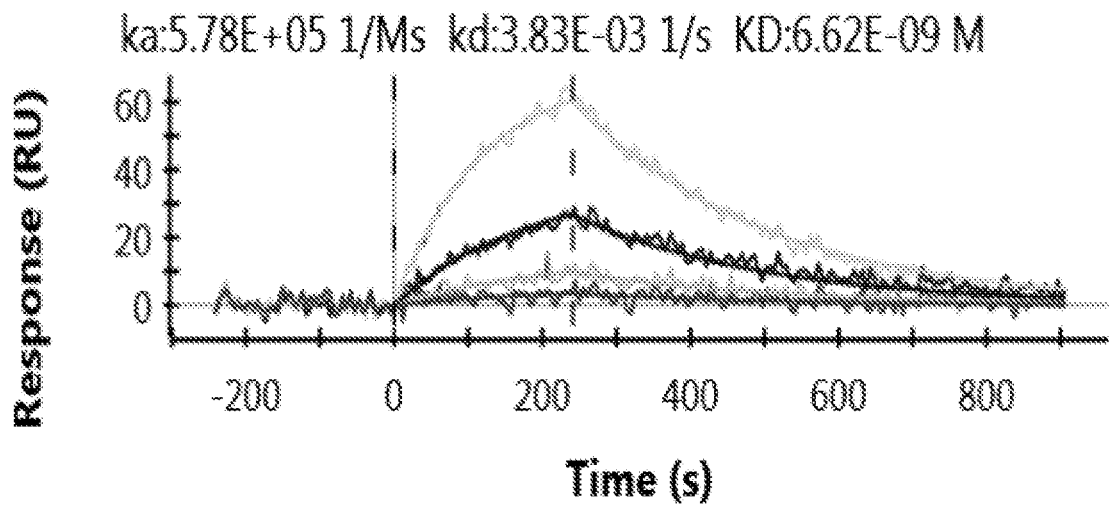
FIG. 6c depicts the binding isotherms for anti-CD3 variant 19363 in a surface plasmon resonance (SPR) binding assay.
Figure 6D:
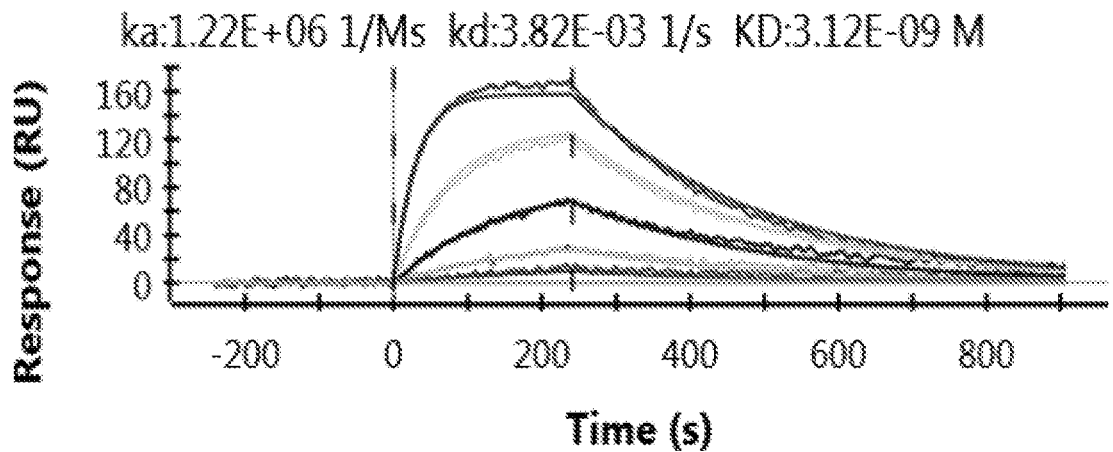
FIG. 6d depicts the binding isotherms for anti-CD3 variant 21829 in a surface plasmon resonance (SPR) binding assay.
Figure 6E:
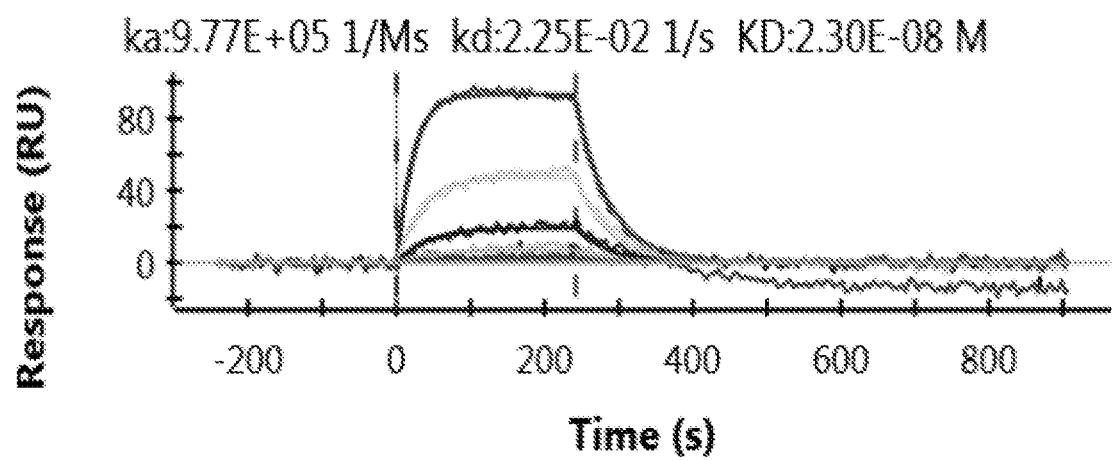
FIG. 6e depicts the binding isotherms for anti-CD3 variant 21831 in a surface plasmon resonance (SPR) binding assay.

The antibodies were purified by Protein A affinity chromatography and subsequent gel filtration, as described in Example 1. FIG. 4 shows two exemplary UPLC-SEC profiles of monovalent anti-CD3 antibodies following Protein A affinity chromatography and gel filtration. Table 4 shows the final post purification yield of the initial parental variants, v18346 and v18343, and the engineered variants.

TABLE 4

| Sample Name | Purification process | Post pA/SEC yield (mg/L) |
|---|---|---|
| 18346 | pA/SEC | 508 |
| 18596 | pA/SEC | 935 |
| 19363 | pA/SEC | 1260 |
| 19362 | pA/SEC | 1400 |
| 21826 | pA/SEC/SEC Arg 0.2M | 1280 |
| 21828 | pA/SEC/SEC Arg 0.2M | 940 |
| 18343 | pA/SEC | 1016 |
| 19373 | pA/SEC | 1010 |
| 19372 | pA/SEC | 990 |
| 19371 | pA/SEC | 930 |
| 19370 | pA/SEC | 1500 |
| 21825 | pA/SEC/SEC Arg 0.2M | 480 |
| 21827 | pA/SEC/SEC Arg 0.2M | 980 |
| 21829 | pA/SEC/SEC Arg 0.2M | 1210 |
| 21831 | pA/SEC/SEC Arg 0.2M | 910 |

The parental variants v18346 and v18343 showed approximately 30% and 10% high molecular aggregates after protein A purification, respectively but a good overall yield. The engineered variants, 18596, 19362, 19363, and 19370-19373 show a similar level of aggregation as the parental variants, whereas variants 21825-21829, and 21831 exhibited increased levels of high molecular weight aggregates compared to the parental controls. The majority of these aggregates are removed through an additional SEC purification step in buffer containing 0.2M Arg. The final post-purification yields for the engineered variants are 2-3-fold higher than the parental controls.

Example 4: Thermal Stability of Engineered Anti-CD3 Antigen-Binding Constructs The thermal stability of the engineered monovalent anti-CD3 constructs in comparison to the parental variants, v18346 and v18343 was assessed by differential scanning calorimetry (DSC). All DSC experiments were carried out using a GE VP-Capillary instrument. The proteins were buffer-exchanged into PBS (pH 7.4) and diluted to 0.3 to 0.7 mg/mL with 0.137 mL loaded into the sample cell and measured with a scan rate of 1° C./min from 20 to 100° C. Data was analyzed using the Origin software (GE Healthcare, Chicago, IL) with the PBS buffer background subtracted.

Table 5 shows a list of the estimated melting temperatures ($T_m$) for the individual anti-CD3 scFvs of the parental vs. the engineered humanized constructs.

TABLE 5

| Variant | Tm (DSC) |
|---|---|
| 18346 | 65.1 |
| 18596 | 63.1 |
| 19363 | 71.6 |
| 19362 | 70.3 |
| 21826 | 66.5 |
| 21828 | 66.8 |
| 18343 | 65.1 |
| 19373 | 65.5 |
| 19372 | 65.4 |
| 19371 | 65.1 |
| 19370 | 65.0 |
| 21825 | 63.0 |
| 21827 | 63.2 |
| 21829 | 63.3 |
| 21831 | 63.7 |

The anti-CD3 scFvs were constructed as described above (Example 1), expressed as monospecific Fc constructs and the purified constructs were measured by DSC as described herein. FIG. 5 illustrates representative DSC thermograms of selected engineered variants versus the parental controls.

The results in Table 5 and FIG. 5 show that most of the engineered constructs have comparable stability to the hC3E-1 parent. However, variants 19363 and 19362, which contain amino acid substitutions designed to increase stability, show approximately a 5 degree increase in $T_m$. Thus, the present disclosure provides hC3E-1 variants comprising $V_H$ and $V_L$ sequences with improved yield and improved stability. These engineered hC3E-1 variants had a yield and stability that was comparable to commercial IgG, thus allowing the development of therapeutic T-cell engaging bispecific antibodies.

Example 5: Antigen Binding of Engineered Monovalent Anti-CD3 Antigen-Binding Constructs To determine whether the engineered monovalent anti-CD3 constructs bind to CD3 antigens equivalent to the parental constructs v18343 or v18346, the binding affinity to CD3 was measured by surface plasmon resonance (SPR) and whole cell fluorescence-activated cell sorting (FACS) as described below.

All SPR binding experiments were carried out using a BioRad ProteOn XPR36 instrument (Bio-Rad Laboratories, Hercules, CA) at 25° C. with 10 mM HEPES, 150 mM NaCl, 3.4 mM EDTA, and 0.05% Tween 20 at pH 7.4. Recombinant CD3epsilon/delta Fc fusion protein (Sino Biological, Wayne, PA) was captured on anti-Fc capture sensorchips. Purified antibodies were indirectly captured on the sensorchip by binding the recombinant CD3 fusion protein when injected at 25 µL/min for 240 s (resulting in approx. 500 RUs) following a buffer injection to establish a stable baseline. Resultant $K_D$ values were determined from binding isotherms using the Equilibrium Fit model with reported values as the mean of three independent runs.

Table 6 and FIG. 6 summarize the results of the SPR binding of the engineered humanized anti-CD3 constructs. The D102E mutation had a strong effect on the affinity of the scFv-Fc constructs to human CD3 when combined with other affinity-modifying mutations, as binding was below the detection limit for all but one of the constructs containing the D102E mutation. All remaining engineered constructs bind to human CD3 antigen with lower affinity than the parental construct v18346, with KDs ranging from 3 to 30 nM.

TABLE 6

| Variant | capture (RU) | KD (nM) | Rmax (RU) |
|---|---|---|---|
| 18346 | 588.37 | 0.26 | 179.28 |
| 18343 | 395.0 | 30 | 94.45 |
| 18596 | 552.64 | 9.0 | 175.53 |
| 19363 | 684.66 | 6.6 | 124.38 |
| 19362 | 762.88 | 3.0 | 143.92 |
| 19370 | 500.6 | 6.8 | 87.52 |
| 19371 | 706.97 | 7.1 | 153.84 |
| 19372 | 747.45 | 3.1 | 99.03 |
| 19373 | 655.51 | 3.0 | 105.7 |
| 21825 | | <det. limit | |
| 21826 | | <det. limit | |
| 21827 | | <det. limit | |
| 21828 | | <det. limit | |
| 21829 | 823.01 | 3.055 | 180.825 |
| 21831 | 730.83 | 22.85 | 185.46 |

These results demonstrate that the immunoglobulin-related compositions of the present technology specifically bind to cells that express human or cynomolgus monkey CD3. Accordingly, the immunoglobulin-related compositions of the present technology are useful for treating cancer by recruiting T cells for TDCC against the cancer.

Figure 7A:
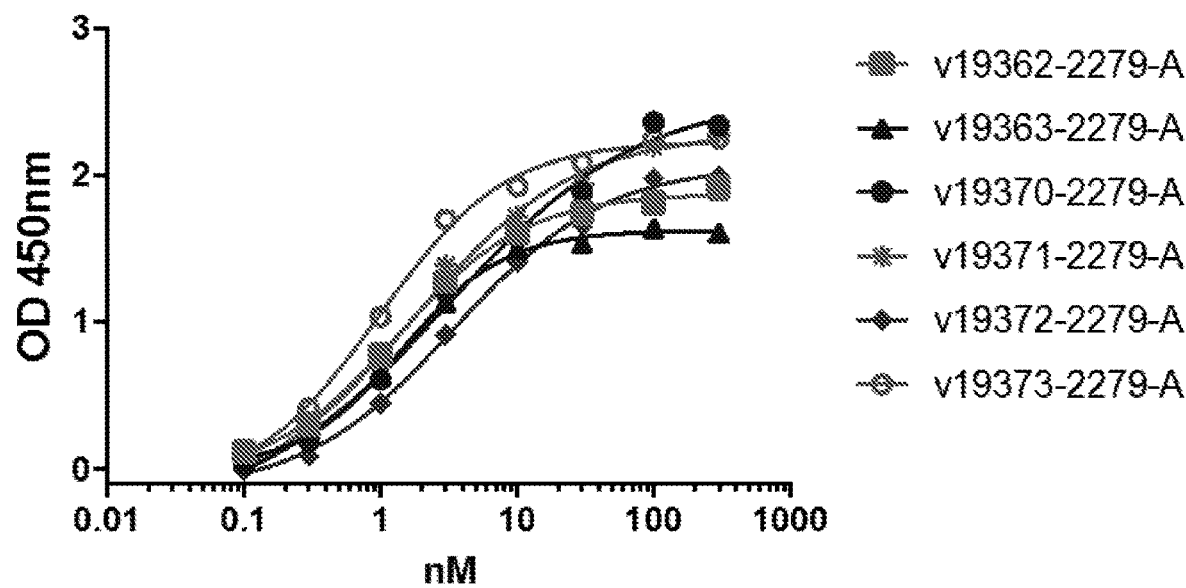
FIGS. 7a-b depict the binding of exemplary anti-CD3 variants to Jurkat cells as detected by a cell ELISA assay.
Figure 7B:
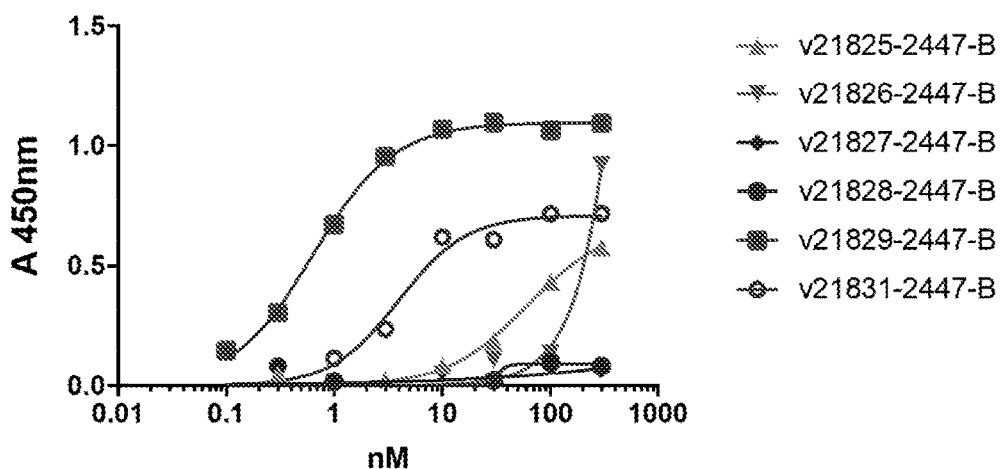

Example 6: Whole Cell Binding of Humanized Anti-CD3 ScFv-Fc Constructs to CD3+ Jurkat T Cells The ability of the humanized anti-CD3 scFv-Fc constructs to bind to CD3+ Jurkat cells (Weiss, *J Immunol.* 133(1): 123-8 (1984)) was assessed via Cell ELISA. Cells were centrifuged and seeded in a 96-well filter plate in 50% complete culture medium/50% Blocking buffer. Equal volumes of 2× anti-CD3 scFv-Fc constructs or controls were added to cells and incubated for 1 hour. The plate was washed 4 times using vacuum filtration. An HRP-conjugated anti-human IgG Fc gamma specific secondary antibody was added to the wells and further incubated for 1 hour. The plate is washed 7 times by vacuum filtration followed by the addition of TMB substrate at room temperature. The reaction was stopped by adding 1 M sulfuric acid and supernatant was transferred into a clear 96-well plate. Absorbance (450 nm) was read on a Spectramax 340PC plate reader with path-check correction. Binding of the different scFv-Fc constructs to Jurkat cells and the apparent binding affinities are shown in FIG. 7 and Table 7, respectively.

The humanized anti-CD3 scFv-Fc constructs bound to CD3+ Jurkat cells with apparent affinities in the low nanomolar range, with the exception of v21826-21828, which contain the D102E mutation. These results correlate with the data obtained by SPR, shown in the example above.

TABLE 7

| Variant | Apparent Affinity (EC50; nM) | | |
|---|---|---|---|
| | Jurkat | human T cells | cyno T cells |
| 18346 | 0.34 | ~0.3 | 1.4 |
| 18596 | 2.57 | 69.47 | 171.5 |
| 19363 | 1.45 | 0.7 | 7.1 |
| 19362 | 1.35 | ~0.6 | 1.9 |
| 19366 | | 1.0 | 12.1 |
| 19367 | | 0.4 | 1.7 |
| 19368 | | 0.8 | 16.8 |
| 21826 | ~36062 | 1.7 | 2.5 |
| 21828 | ~32.79 | 1.6 | 104.2 |
| 18343 | 2.61 | — | — |
| 19373 | 0.99 | — | — |
| 19372 | 3.47 | 0.9 | 9.3 |
| 19371 | 1.72 | 0.5 | 3.4 |
| 19370 | 3.09 | 0.7 | 2.4 |
| 21825 | 61.29 | ~1.2 | 7.0 |
| 21827 | ~394192310 | 1.9 | 16.3 |
| 21829 | 0.65 | 0.4 | 1.6 |
| 21831 | 3.96 | 1.0 | 40.7 |

These results demonstrate that the immunoglobulin-related compositions of the present technology specifically bind to cells that express human or cynomolgus monkey CD3. Accordingly, the immunoglobulin-related compositions of the present technology are useful for treating cancer by recruiting T cells for TDCC against the cancer.

Example 7: Whole Cell Binding of Humanized Anti-CD3 ScFv-Fc Constructs to Human and Cynomolgus Monkey PBMCs Frozen human pan T cells or PBMCs were thawed and incubated with either media or serial dilutions of the anti-CD3 scFv-Fc constructs for one hour at 4° C. Commercially available SP34-2 antibody was used as positive controls while untreated cultures were used as negative controls. Following incubation with the anti-CD3 scFv constructs, the cells were washed and stained with a panel of conjugated antibodies specific for CD4, CD8, and IgG-Fc. The samples were acquired on a flow cytometer and analyzed using FlowJo version 10.1 software.

Figure 8:
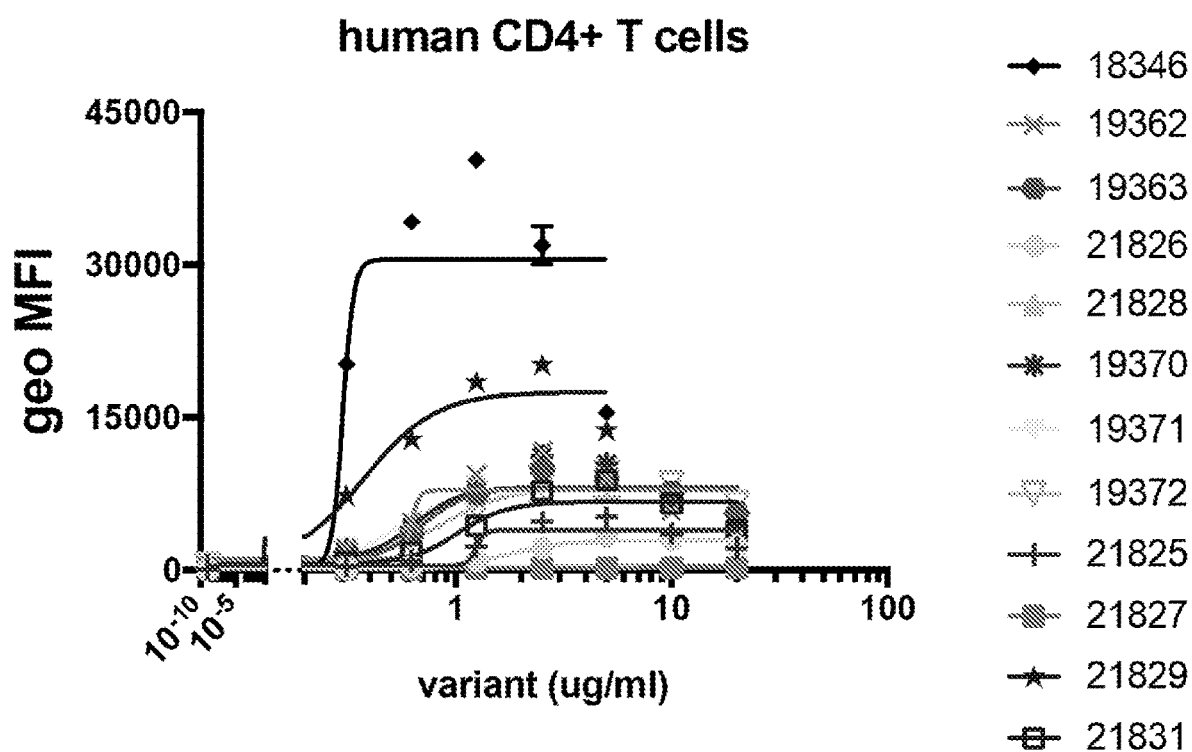
FIG. 8 depicts the binding of exemplary anti-CD3 variants to human CD4+ T cells as measured by flow cytometry.

As shown in FIG. 8 and Table 7, the engineered anti-CD3 scFv-Fc constructs bound to human CD3 expressed on CD4+ and CD8+ T cells with a range of relative binding affinities. Switching of the antibody framework from λ6 to λ1 (V6 to V1) did not alter binding to human CD3. Introduction of the D102E mutation into variants 21825-21828 caused a reduction in relative affinity to human CD3 compared to variants 21829 and 21831, which lack the D102E mutation and have similar relative affinity to CD3 as the parent variants.

Frozen Cynomolgus monkey PBMCs were thawed then washed with RPMI-1640 media. Pan T cells were then isolated from the PBMCs using a negative isolation kit (Miltenyi Biotec, San Diego, CA) as per the manufacturer's instructions. The pan T cells were incubated in media alone or media containing serial dilutions of the anti-CD3 scFv-Fc constructs for one hour at 4° C. Commercially available SP34-2 antibody was used as positive controls while untreated cultures were used as negative controls. Following incubation with the anti-CD3 scFv constructs, the cells were washed and stained with a panel of conjugated antibodies specific for CD4, CD8, and IgG-Fc. The samples were acquired on a flow cytometer and analyzed using FlowJo version 10.1 software.

Figure 9:
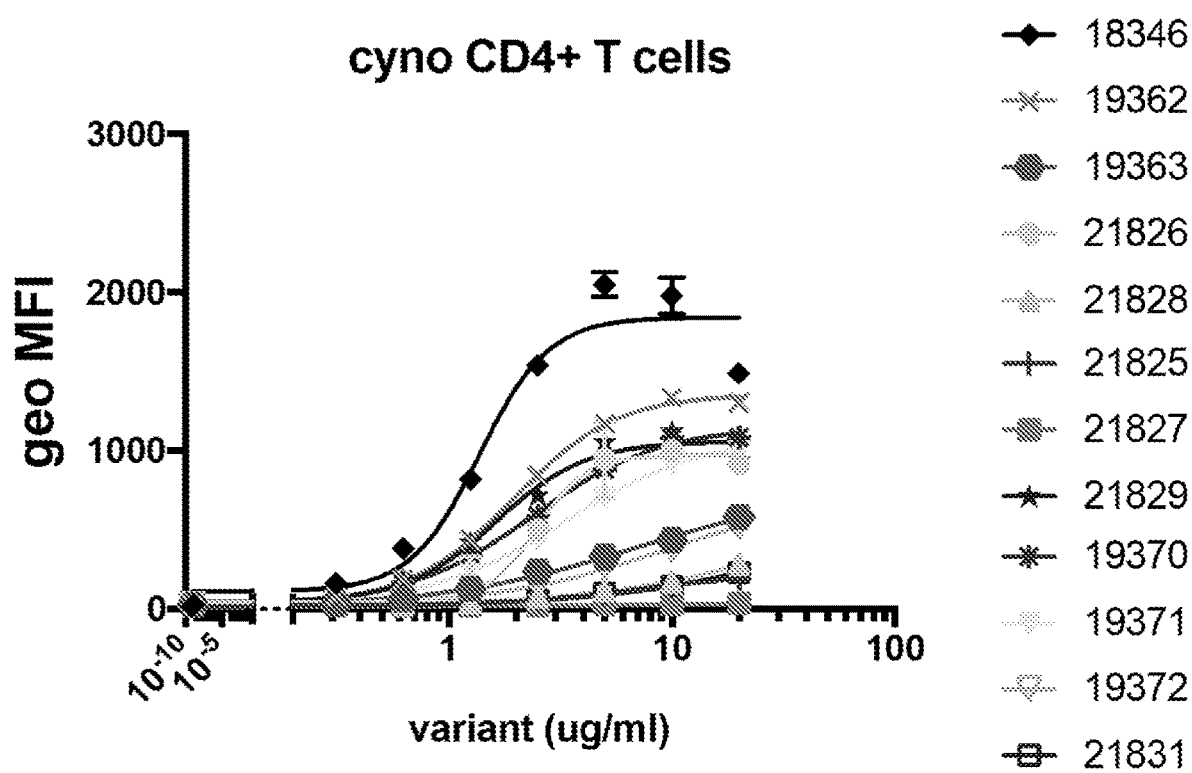
FIG. 9 depicts the binding of exemplary anti-CD3 variants to cynomolgus monkey CD4+ T cells as measured by flow cytometry.

As shown in FIG. 9 and Table 7, the engineered anti-CD3 scFv-Fc constructs bound to cyno CD3 expressed on CD4+ and CD8+ T cells with a range of relative binding affinities. Switching of the antibody framework from λ6 to λ1 (V6 to V1) did not alter binding to cyno CD3. Introduction of the D102E mutation into variants 21825-21828 caused a reduction in relative affinity to cyno CD3 compared to variants 21829 and 21831, which lack the mutation.

These results demonstrate that the immunoglobulin-related compositions of the present technology specifically bind to cells that express human or cynomolgus monkey CD3. Accordingly, the immunoglobulin-related compositions of the present technology are useful for treating cancer by recruiting T cells for TDCC against the cancer.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An antibody or antigen binding fragment thereof comprising a heavy chain immunoglobulin variable domain ($V_H$) and a light chain immunoglobulin variable domain ($V_L$), wherein:
   (a) the $V_H$ comprises a $V_H$-CDR1 sequence of GVTFNYYG (SEQ ID NO: 3), a $V_H$-CDR2 sequence selected from the group consisting of ITRSGGRI (SEQ ID NO: 5) and ITSSGGRI (SEQ ID NO: 14), and a $V_H$-CDR3 sequence of TLDGREGWVAY (SEQ ID NO: 156); and
   (b) the $V_L$ comprises a $V_L$-CDR1 sequence of: TGNIGSNY (SEQ ID NO: 7), a $V_L$-CDR2 sequence of RND (SEQ ID NO: 9), and a $V_L$-CDR3 sequence of: QSYSSGFI (SEQ ID NO: 8); wherein the $V_H$ and $V_L$ are connected via an amino acid linker comprising the sequence (GGGGS)$_3$ (SEQ ID NO: 224).

2. An antibody or antigen binding fragment thereof comprising a heavy chain immunoglobulin variable domain ($V_H$) and a light chain immunoglobulin variable domain ($V_L$), wherein the $V_H$ and $V_L$ are connected via an amino acid linker comprising the sequence (GGGGS)$_3$ (SEQ ID NO: 224) and wherein:
   (a) the $V_H$ comprises a $V_H$-CDR1 sequence, a $V_H$-CDR2 sequence, and a $V_H$-CDR3 sequence of SEQ ID NO: 155, SEQ ID NO: 157, and SEQ ID NO: 156 respectively, and the $V_L$ comprises a $V_L$-CDR1 sequence, a $V_L$-CDR2 sequence, and a $V_L$-CDR3 sequence of SEQ ID NO: 160, SEQ ID NO: 162, and SEQ ID NO: 161 respectively;
   (b) the $V_H$ comprises a $V_H$-CDR1 sequence, a $V_H$-CDR2 sequence, and a $V_H$-CDR3 sequence of SEQ ID NO: 135, SEQ ID NO: 137, and SEQ ID NO: 136 respectively, and the $V_L$ comprises a $V_L$-CDR1 sequence, a $V_L$-CDR2 sequence, and a $V_L$-CDR3 sequence of SEQ ID NO: 140, SEQ ID NO: 142, and SEQ ID NO: 141 respectively;
   (c) the $V_H$ comprises a $V_H$-CDR1 sequence, a $V_H$-CDR2 sequence, and a $V_H$-CDR3 sequence of SEQ ID NO: 175, SEQ ID NO: 177, and SEQ ID NO: 176 respectively, and the $V_L$ comprises a $V_L$-CDR1 sequence, a $V_L$-CDR2 sequence, and a $V_L$-CDR3 sequence of SEQ ID NO: 180, SEQ ID NO: 182, and SEQ ID NO: 181 respectively;
   (d) the $V_H$ comprises a $V_H$-CDR1 sequence, a $V_H$-CDR2 sequence, and a $V_H$-CDR3 sequence of SEQ ID NO: 145, SEQ ID NO: 147, and SEQ ID NO: 146 respectively, and the $V_L$ comprises a $V_L$-CDR1 sequence, a $V_L$-CDR2 sequence, and a $V_L$-CDR3 sequence of SEQ ID NO: 150, SEQ ID NO: 152, and SEQ ID NO: 151 respectively; or
   (e) the $V_H$ comprises a $V_H$-CDR1 sequence, a $V_H$-CDR sequence, and a $V_H$-CDR3 sequence of SEQ ID NO: 165, SEQ ID NO: 167, and SEQ ID NO: 166 respectively, and the $V_L$ comprises a $V_L$-CDR1 sequence, a $V_L$-CDR2 sequence, and a $V_L$-CDR3 sequence of SEQ ID NO: 170, SEQ ID NO: 172, and SEQ ID NO: 171 respectively.

3. An antibody or antigen binding fragment thereof comprising
   a heavy chain immunoglobulin variable domain ($V_H$) amino acid sequence comprising SEQ ID NO: 133, SEQ ID NO: 143, SEQ ID NO: 153, SEQ ID NO: 163, or SEQ ID NO: 173; and
   a light chain immunoglobulin variable domain ($V_L$) amino acid sequence comprising SEQ ID NO: 138, SEQ ID NO: 148, SEQ ID NO: 158, SEQ ID NO: 168, or SEQ ID NO: 178.

4. The antibody or antigen binding fragment of claim 3, comprising a $V_H$ amino acid sequence and a $V_L$ amino acid sequence selected from the group consisting of:
   (a) SEQ ID NO: 163 and SEQ ID NO: 168 (v18596);
   (b) SEQ ID NO: 153 and SEQ ID NO: 158 (v21826);
   (c) SEQ ID NO: 133 and SEQ ID NO: 138 (v21828);
   (d) SEQ ID NO: 173 and SEQ ID NO: 178 (v21825); and
   (e) SEQ ID NO: 143 and SEQ ID NO: 148 (v21827).

5. The antibody or antigen binding fragment of claim 1, wherein the antibody or antigen binding fragment binds to human CD3 and cynomolgus monkey CD3.

6. The antibody or antigen binding fragment of claim 1, wherein the antigen binding fragment is selected from the group consisting of Fab, F(ab')$_2$, Fab', scF$_v$, sdAb, and F$_v$.

7. The antibody or antigen binding fragment of claim 1, wherein the antibody or antigen binding fragment is monoclonal, chimeric, humanized, or bispecific.

8. The antibody or antigen binding fragment of claim 1, wherein the antibody or antigen binding fragment comprises an Fc domain.

9. The antibody or antigen binding fragment of claim 8, wherein the Fc domain has an isotype selected from the group consisting of IgG1, IgG2, IgG3, IgG4, IgA1, IgA2, IgM, IgD, and IgE.

10. The antibody or antigen binding fragment of claim 9, wherein the Fc domain is heterodimeric and comprises an IgG constant domain.

11. The antibody or antigen binding fragment of claim 10, wherein the heterodimeric Fc domain comprises a first CH2 region, a first CH3 region, a second CH2 region and a second CH3 region.

12. The antibody or antigen binding fragment of claim 11, wherein the IgG constant domain is human IgG1 constant domain.

13. The antibody or antigen binding fragment of claim 12, wherein the first CH3 region comprises one or more amino acid substitutions selected from the group consisting of T350V, L351Y, F405A, and Y407V.

14. The antibody or antigen binding fragment of claim 12, wherein the second CH3 region comprises one or more amino acid substitutions selected from the group consisting of T350V, T366L, K392L, and T394W.

15. The antibody or antigen binding fragment of claim 12, wherein the first CH2 region and/or the second CH2 region comprises one or more amino acid substitutions selected from the group consisting of D265S, L234A, and L235A.

16. The antibody or antigen binding fragment of claim 12, wherein the first CH2 region comprises the amino acid sequence of SEQ ID NO: 195 and the first CH3 domain comprises the amino acid sequence of SEQ ID NO: 197.

17. The antibody or antigen binding fragment of claim 12, wherein the second CH2 region comprises the amino acid sequence of SEQ ID NO: 201 and the second CH3 domain comprises the amino acid sequence of SEQ ID NO: 203.

18. A recombinant nucleic acid sequence encoding the antibody or antigen binding fragment of claim 1.

19. A host cell or vector comprising the recombinant nucleic acid sequence of claim 18.

20. A pharmaceutical composition comprising the antibody or antigen binding fragment of claim 1 and a pharmaceutically-acceptable carrier.

21. The pharmaceutical composition of claim 20, wherein the antibody or antigen binding fragment is optionally conjugated to an agent selected from the group consisting of isotopes, dyes, chromogens, contrast agents, drugs, toxins, cytokines, enzymes, enzyme inhibitors, hormones, hormone antagonists, growth factors, radionuclides, metals, liposomes, nanoparticles, RNA, DNA, antioxidants, proteins, carbohydrates, lipids, chelating agents, stabilizers, or any combination thereof.

22. The pharmaceutical composition of claim 20, wherein the antibody or antigen binding fragment is a bispecific antibody.

23. A method for treating cancer in a subject in need thereof, comprising administering to the subject an effective amount of the antibody or antigen binding fragment of the pharmaceutical composition of claim 22.

24. A kit comprising the antibody or antigen binding fragment of claim 1 and instructions for use.

25. The kit of claim 24, wherein the antibody or antigen binding fragment is coupled to at least one detectable label selected from the group consisting of a radioactive label, a fluorescent label, and a chromogenic label.

26. The kit of claim 24, further comprising a secondary antibody that specifically binds to the antibody or antigen binding fragment that binds to CD3.

* * * * *

UNITED STATES PATENT AND TRADEMARK OFFICE
CERTIFICATE OF CORRECTION

| | | |
|---|---|---|
| PATENT NO. | : 12,129,298 B2 | Page 1 of 1 |
| APPLICATION NO. | : 17/254105 | |
| DATED | : October 29, 2024 | |
| INVENTOR(S) | : Thomas Spreter Von Kreudenstein | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 800 days.

Signed and Sealed this
Twelfth Day of August, 2025

Coke Morgan Stewart
*Acting Director of the United States Patent and Trademark Office*